(12) United States Patent
Jansen et al.

(10) Patent No.: US 7,678,929 B2
(45) Date of Patent: Mar. 16, 2010

(54) FUROCHROMAN DERIVATIVES

(75) Inventors: Axel Jansen, Darmstadt (DE); Andreas Taugerbeck, Darmstadt (DE); Melanie Klasen-Memmer, Heuchelheim (DE); Georg Bernatz, Darmstadt (DE)

(73) Assignee: Merck Patent Gesellschaft mit Beschrankter Haftung, Darmstadt (DE)

( * ) Notice: Subject to any disclaimer, the term of this patent is extended or adjusted under 35 U.S.C. 154(b) by 91 days.

(21) Appl. No.: 11/949,145

(22) Filed: Dec. 3, 2007

(65) Prior Publication Data

US 2008/0177095 A1  Jul. 24, 2008

(30) Foreign Application Priority Data

Dec. 4, 2006  (EP) .................................. 06025029

(51) Int. Cl.
*C07D 493/04* (2006.01)
(52) U.S. Cl. .................................. 549/387; 252/299.61
(58) Field of Classification Search ................. 549/387; 252/299.61
See application file for complete search history.

(56) References Cited

U.S. PATENT DOCUMENTS

2005/0247910 A1  11/2005  Sugiura

FOREIGN PATENT DOCUMENTS

| DE | 199 00 517 A1 | 7/1999 |
| DE | 10 2005 016985 A1 | 11/2005 |
| DE | 10 2005 045848 A1 | 4/2006 |
| DE | 10 2005 045849 A1 | 4/2006 |
| EP | 1 491 612 A | 12/2004 |

*Primary Examiner*—Bernard Dentz
(74) *Attorney, Agent, or Firm*—Millen, White, Zelano & Branigan, P.C.

(57) ABSTRACT

Disclosed are furochroman compounds of formula I

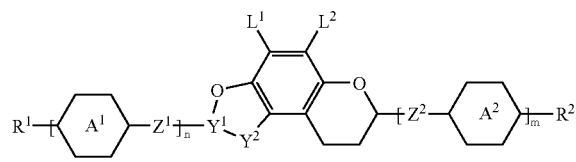

liquid-crystal media which contains the compounds of formula I, and the use of the media in electro-optical displays, in particular in VAN LCDs.

20 Claims, No Drawings

FUROCHROMAN DERIVATIVES

The present invention relates to furochroman derivatives, preferably mesogenic furochroman derivatives, in particular liquid-crystalline furochroman derivatives, and to liquid-crystalline media comprising these furochroman derivatives. The present invention furthermore relates to liquid-crystal displays, in particular active matrix addressed liquid-crystal displays (AMDs or AM LCDs) and very particularly so-called VAN ("vertically aligned nematic") liquid-crystal displays, an embodiment of ECB ("electrically controlled birefringence") liquid-crystal displays, in which nematic liquid crystals of negative dielectric anisotropy ($\Delta\epsilon$) are used.

In liquid-crystal displays of this type, the liquid crystals are used as dielectrics, whose optical properties change reversibly on application of an electric voltage. Electro-optical displays which use liquid crystals as media are known to the person skilled in the art. These liquid-crystal displays use various electro-optical effects. The commonest thereof are the TN ("twisted nematic") effect, with a homogeneous, virtually planar initial alignment of the liquid-crystal director and a nematic structure which is twisted by about 90°, the STN ("super-twisted nematic") effect and the SBE ("supertwisted birefringence effect") with a nematic structure which is twisted by 180° or more. In these and similar electro-optical effects, liquid-crystalline media of positive dielectric anisotropy ($\Delta\epsilon$) are used.

Besides the said electro-optical effects, which require liquid-crystal media of positive dielectric anisotropy, there are other electro-optical effects which use liquid-crystal media of negative dielectric anisotropy, such as, for example, the ECB effect and its sub-forms DAP ("deformation of aligned phases"), VAN and CSH ("colour super homeotropics").

An electro-optical effect having excellent, low viewing-angle dependence of the contrast uses axially symmetrical micropixels (ASMs). In this effect, the liquid crystal of each pixel is surrounded in a cylindrical manner by a polymer material. This mode is particularly suitable for combination with addressing through plasma channels. Thus, in particular, large-area PA ("plasma addressed") LCDs having good viewing-angle dependence of the contrast can be achieved.

The IPS ("in plane switching") effect employed to an increased extent recently can use both dielectrically positive and also dielectrically negative liquid-crystal media, in a similar manner to "guest/host" displays, which can employ dyes either in dielectrically positive or dielectrically negative media, depending on the display mode used.

Since the operating voltage in liquid-crystal displays in general, i.e. also in displays utilising these effects, should be as low as possible, use is made of liquid-crystal media having a large absolute value of the dielectric anisotropy which generally predominantly and in most cases even essentially consist of liquid-crystal compounds having a dielectric anisotropy having the corresponding sign, i.e. of compounds of positive dielectric anisotropy in the case of dielectrically positive media and of compounds of negative dielectric anisotropy in the case of dielectrically negative media. In the respective types of media (dielectrically positive or dielectrically negative), at most significant amounts of dielectrically neutral liquid-crystal compounds are typically employed. Liquid-crystal compounds having the opposite sign of the dielectric anisotropy to that of the dielectric anisotropy of the medium are generally employed extremely sparingly or not at all.

An exception is formed here by liquid-crystalline media for MIM ("metal-insulator-metal") displays (Simmons, J. G., Phys. Rev. 155, 3, 657-660 and Niwa, J. G. et al., SID 84 Digest, 304-307, June 1984), in which the liquid-crystal media are addressed by means of an active matrix of thin-film transistors. In this type of addressing, which utilises the nonlinear characteristic line of diode switching, a storage capacitor cannot be charged together with the electrodes of the liquid-crystal display elements (pixels), in contrast to TFT displays. In order to reduce the effect of the drop in voltage during the addressing cycle, the largest possible base value of the dielectric constant is thus necessary. In the case of dielectrically positive media, as employed, for example, in MIM-TN displays, the dielectric constant perpendicular to the molecular axis ($\epsilon_\perp$) must thus be as large as possible since it determines the basic capacitance of the pixel. To this end, as described, for example, in WO 93/01253, EP 0 663 502 and DE 195 21 483, compounds of negative dielectric anisotropy are simultaneously also employed besides dielectrically positive compounds in the dielectrically positive liquid-crystal media.

A further exception is formed by STN displays, in which, for example, dielectrically positive liquid-crystal media in accordance with DE 41 00 287 comprising dielectrically negative liquid-crystal compounds are employed in order to increase the steepness of the electro-optical characteristic line.

The pixels of the liquid-crystal displays can be addressed directly, time-sequentially, i.e. in time multiplex mode, or by means of a matrix of active elements having nonlinear electrical characteristic lines.

The commonest AMDs to date use discrete active electronic switching elements, such as, for example, three-pole switching elements, such as MOS ("metal oxide silicon") transistors or thin film transistors (TFTs) or varistors, or 2-pole switching elements, such as, for example, MIM ("metal-insulator-metal") diodes, ring diodes or "back-to-back" diodes. Various semiconductor materials, predominantly silicon, but also cadmium selenide, are used in the TFTs. In particular, amorphous silicon or polycrystalline silicon is used.

In accordance with the present application, preference is given to liquid-crystal displays having an electric field perpendicular to the liquid-crystal layer and liquid-crystal media of negative dielectric anisotropy ($\Delta\epsilon<0$). In these displays, the edge alignment of the liquid crystals is homeotropic. In the fully switched-through state, i.e. on application of an electric voltage of appropriate magnitude, the liquid-crystal director is aligned parallel to the layer plane.

Chroman derivatives and the use thereof as a component in liquid-crystal mixtures are described in the specification EP 1 491 612 A1.

The use of benzofurans or dihydrobenzofurans in liquid-crystal mixtures is described in the specification DE 199 00 517 A1.

Furthermore, it is pointed out in the literature [M. Bremer, L. Lietzau, New. J. Chem. 2005, 29, 72-74] that the introduction of an alkoxy side chain fixed to the aromatic ring into liquid crystals based on the 2,3-difluorophenyl unit, such as, for example, into benzofurans or dihydrobenzofurans, gives compounds having comparatively high polarity.

The development in the area of liquid-crystalline materials is still far from complete. In order to improve the properties of liquid-crystalline display elements, attempts are constantly being made to develop novel compounds which enable optimisation of displays of this type.

It is therefore an object of the present invention to provide compounds having advantageous properties for use in liquid-crystalline media. They should preferably have negative dielectric anisotropy ($\Delta\epsilon<0$), which makes them particularly suitable for use in liquid-crystalline media for VA displays. In order to guarantee satisfactory properties, in particular low characteristic voltages, in, for example, VA-TFT displays, substances having a large absolute value of the dielectric anisotropy (Δ∈), a value of the optical anisotropy (Δn) which corresponds to the particular application, and good stability to UV, heat and electric voltage are required.

This is achieved by the use of the compounds of the formula I according to the invention

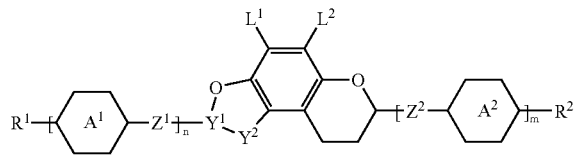

I in which

R$^1$ and R$^2$ each, independently of one another, denote H, halogen, —CN, —SCN, —SF$_5$, —CF$_3$, —CHF$_2$, —CH$_2$F, —OCF$_3$, —OCHF$_2$ or an alkyl group having 1 to 15 C atoms, which may optionally be monosubstituted by CN or CF$_3$ or at least monosubstituted by halogen and in which one or more CH$_2$ groups, in each case independently of one another, may in each case be replaced by —O—, —S—, —CH═CH—, —CF═CF—, —CF═CH—, —CH═CF—,

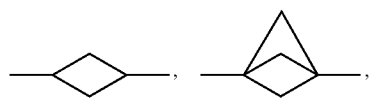

—CO—, —CO—O—, —O—CO— or —O—CO—O— in such a way that neither O nor S atoms are linked directly to one another, one of the radicals R$^1$ and R$^2$ preferably denotes alkyl or alkoxy having 1 to 12 C atoms, alkoxyalkyl, alkenyl or alkenyloxy having 2 to 12 C atoms, and the other, independently of the first, likewise denotes alkyl or alkoxy having 1 to 12 C atoms, alkoxyalkyl, alkenyl or alkenyloxy having 2 to 12 C atoms or alternatively F, Cl, Br, —CN, —SCN, —SF$_5$, —CF$_3$, —CHF$_2$, —CH$_2$F, —OCF$_3$ or —OCHF$_2$, >Y$^1$—Y$^2$— denotes >C═CH— or >CH—CH$_2$—, preferably >C═CH—, L$^1$ and L$^2$ each, independently of one another, denote H, halogen, —CN or —CF$_3$, preferably H, F or Cl, particularly preferably H or F and very particularly preferably F,

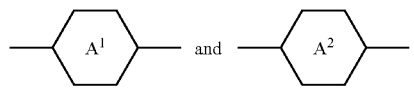

each, independently of one another, and, if present more than once, these also independently of one another, denote (a) a trans-1,4-cyclohexylene radical, in which, in addition, one or two non-adjacent CH$_2$ groups may be replaced by —O— and/or —S—, (b) a 1,4-cyclohexenylene radical, (c) a 1,4-phenylene radical, in which, in addition, one or two non-adjacent CH groups may be replaced by N, (d) a radical selected from the group naphthalene-2,6-diyl, decahydronaphthalene-2,6-diyl and 1,2,3,4-tetrahydronaphthalene-2,6-diyl, or (e) a radical selected from the group 1,4-bicyclo[2.2.2]octylene, 1,3-bicyclo[1.1.1]pentylene and spiro[3.3]heptane-2,6-diyl, where in (a) and (b), one or more —CH$_2$— groups, independently of one another, may each be replaced by a —CHF— or a —CF$_2$— group, and in (c) and (d), one or more —CH═ groups, independently of one another, may each be replaced by a group selected from the group —CF═, —CCl═, —CBr═, —C(CN)═, —C(CH$_3$)═, —C(CH$_2$F)═, —C(CHF$_2$)═, —C(OCH$_3$)═, —C(OCHF$_2$)═ and —C(OCF$_3$)═, preferably a —CF═ group, and preferably

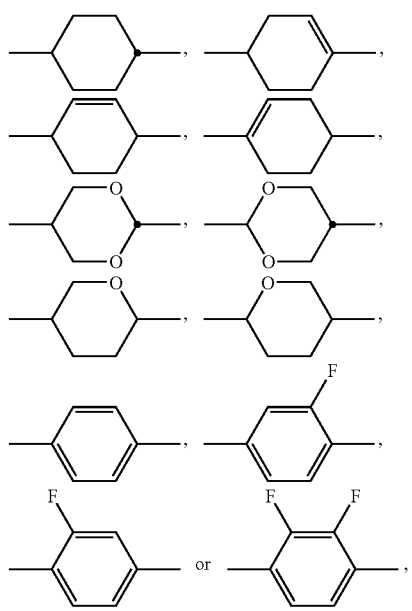

particularly preferably

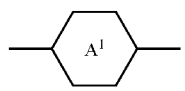

denotes

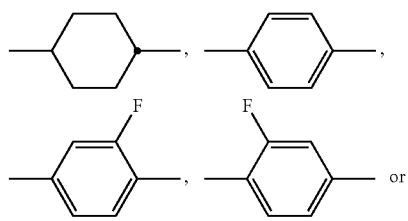

-continued

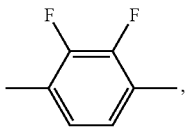

particularly preferably

denotes

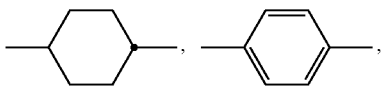

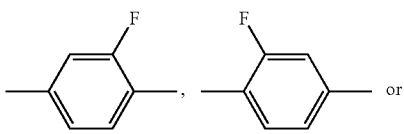

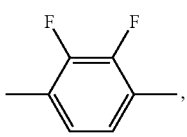

, $Z^1$ and $Z^2$ each, independently of one another, and, if present more than once, these also independently of one another, denote a single bond, —CH$_2$—CH$_2$—, —CF$_2$—CH$_2$—, —CH$_2$—CF$_2$—, —CF$_2$—CF$_2$—, —CH═CH—, —CF═CF—, —CF═CH—, —CH═CF—, —C≡C—, —COO—, —OCO—, —CH$_2$O—, —OCH$_2$—, —CF$_2$O—, —OCF$_2$—, or a combination of two of these groups, where no two O atoms are bonded to one another, preferably —(CH$_2$)$_4$—, —CH$_2$—CH$_2$—, —CF$_2$—CF$_2$—, —CH═CH—, —CF═CF—, —C≡C—, —CH$_2$O—, —CF$_2$O— or a single bond, particularly preferably —CH$_2$O—, —CH$_2$—CH$_2$—, —CF$_2$—CF$_2$—, —CF═CF—, —CF$_2$O— or a single bond, and n and m each denote 0, 1, 2 or 3, where (n+m) denotes 0, 1, 2 or 3, preferably 0, 1 or 2, particularly preferably 0 or 1.

The compounds of the formula I according to the invention are preferably mesogenic compounds and particularly preferably liquid-crystalline compounds.

Compounds of the formula I according to the invention are particularly preferably selected from the sub-formulae IA and IB (where IA: >Y$^1$—Y$^2$—═>C═CH— and IB: >Y$^1$—Y$^2$—═>CH—CH$_2$—):

IA

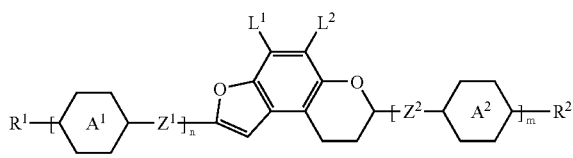

IB

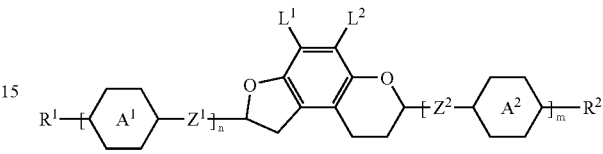

in which the parameters have the respective meanings given above under formula I.

Preference is given to compounds of the formula I which are preferably selected from the group of the compounds of the formulae IA and IB in which the sum n+m is 0, 1 or 2, particularly preferably 0 or 1.

A preferred embodiment is represented by the compounds of the formula I in which the sum n+m is 1, and preferably

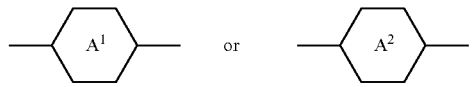

denotes

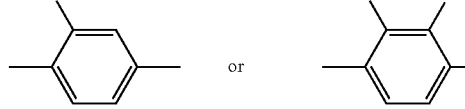

particularly preferably

denotes

, 

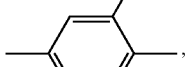 or

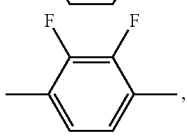, particularly preferably

denotes

, 

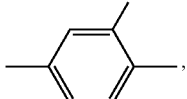 or

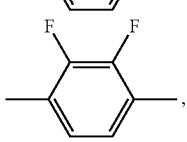, $Z^1$, $Z^2$ preferably denote —(CH$_2$)$_4$—, —CH$_2$—CH$_2$—, —CF$_2$—CF$_2$—, —CH=CH—, —CF=CF—, —C≡C—, —O—CH$_2$—, —O—CF$_2$— or a single bond, particularly preferably —O—CH$_2$—, —CH$_2$—CH$_2$—, —CF$_2$—CF$_2$—, —CF=CF—, —O—CF$_2$— or a single bond, and $L^1$, $L^2$, $R^1$ and $R^2$ have the meanings given above under formula I, and $L^1$ and $L^2$ preferably denote F.

Particular preference is given to compounds of the formula I which are preferably selected from the group of the compounds of the formulae IA and IB in which n and m both denote 0, and $L^1$, $L^2$, $R^1$ and $R^2$ have the meanings given above under the corresponding formula, and $L^1$ and $L^2$ preferably denote F.

Particular preference is given to compounds of the formula IA which are selected from the group of the compounds of the formulae IA-1 to IA-11, preferably of the formulae IA-1 to IA-6, particularly preferably of the formulae IA-1 to IA-3, IA-5 and IA-6, in which at least one of the groups $R^1$ and $R^2$ is linked directly to the skeleton:

IA-1

IA-2

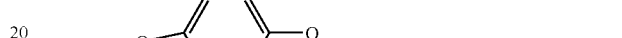

IA-3

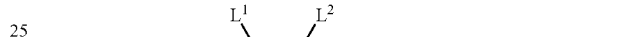

IA-4

IA-5

IA-6

IA-7

IA-8

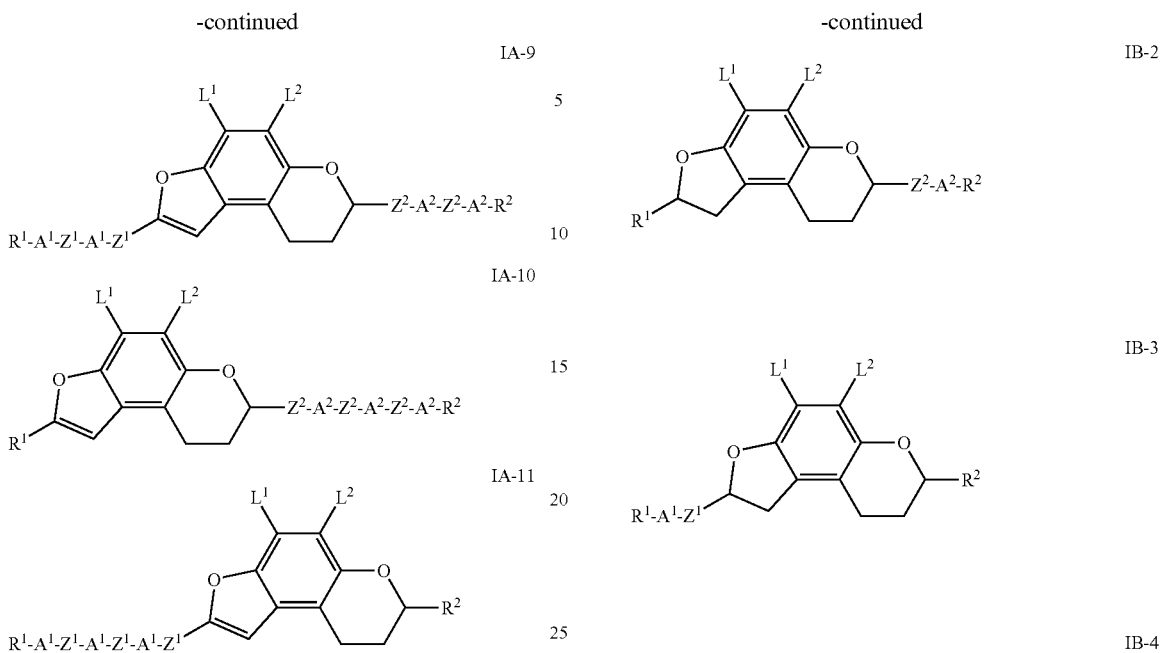

in which the parameters have the respective meanings given above.

Here, as throughout the present application, the group of the sub-formula I-1

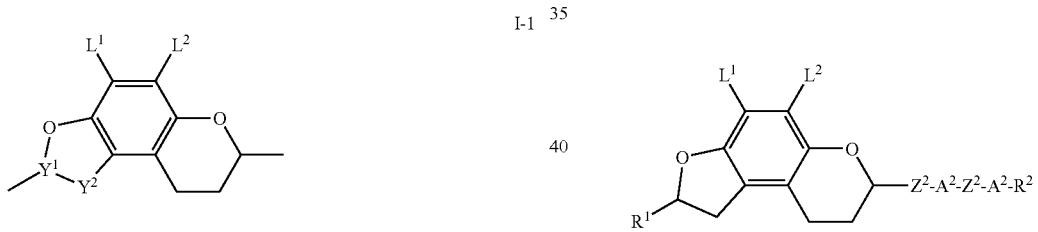

in which the parameters have the meanings given above, and preferably

>Y$^1$—Y$^2$ denotes >C=CH—, is referred to as the skeleton of the compounds of the formula I, or for short as the skeleton.

Particular preference is given to compounds of the formula IB which are selected from the group of the compounds of the formulae IB-1 to IB-11, preferably of the formulae IB-1 to IB-6, particularly preferably of the formulae IB-1 to IB-3, IB-5 and IB-6, in which at least one of the groups R$^1$ and R$^2$ is linked directly to the skeleton:

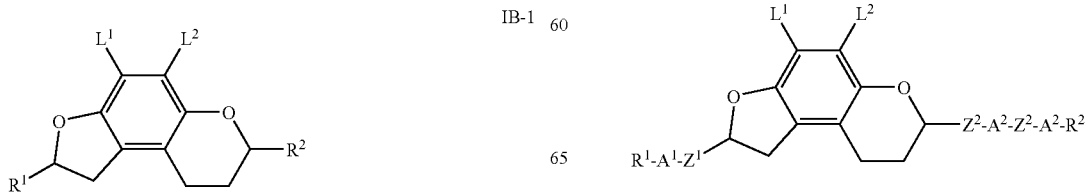

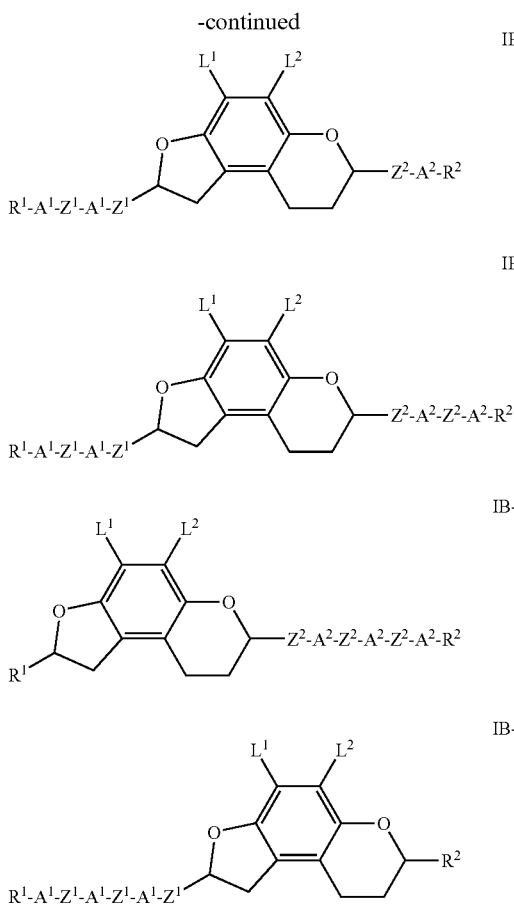

in which the parameters have the respective meanings given above.

Particular preference is given to compounds of the formula I which have one or more fluorine substituents, very particularly preferably two fluorine substituents, in the skeleton.

Compounds of the formula I containing branched wing groups $R^1$ and/or $R^2$ may occasionally be of importance owing to better solubility in the usual liquid-crystalline base materials, but in particular as chiral dopants if they are optically active. Smectic compounds of this type are suitable as components of ferroelectric materials. Compounds of the formula I having $S_A$ phases are suitable, for example, for thermally addressed displays.

If $R^1$ and/or $R^2$ denote an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl or alkoxyalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ and/or $R^2$ denote an alkyl radical in which one $CH_2$ group has been replaced by —CH=CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ and/or $R^2$ denote an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms.

Accordingly, they denote, in particular, acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ and/or $R^2$ denote an alkyl radical in which one $CH_2$ group has been replaced by unsubstituted or substituted —CH=CH— and an adjacent $CH_2$ group has been replaced by CO or CO—O or O—CO, this may be straight-chain or branched. It is preferably straight-chain and has 4 to 13 C atoms. Accordingly, it denotes, in particular, acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^1$ and/or $R^2$ denote an alkyl or alkenyl radical which is monosubstituted by CN or $CF_3$, this radical is preferably straight-chain. The substitution by CN or $CF_3$ is in any desired position.

If $R^1$ and/or $R^2$ denote an alkyl or alkenyl radical which is at least monosubstituted by halogen, this radical is preferably straight-chain, and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

Branched groups generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexyloxy, 1-methylhexyloxy and 1-methylheptyloxy.

If $R^1$ and/or $R^2$ represent an alkyl radical in which two or more $CH_2$ groups have been replaced by —O— and/or —CO—O—, this may be straight-chain or branched. It is preferably branched and has 3 to 12 C atoms. Accordingly, it denotes, in particular, biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl) heptyl, 8,8-bis(methoxycarbonyl)octyl, bis(ethoxycarbonyl) methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)pentyl.

Especial preference is given to compounds of the formula I in which one of the parameters m and n has the value 0 and the other has a value as defined above, preferably >0, and to media comprising these compounds. Particularly preferably, therefore, m=0 and n=0, 1 or 2 or n=0 and m=0, 1 or 2, where $R^1$ and/or $R^2$ preferably denote methyl, ethyl, propyl, butyl, pentyl, vinyl, 1E-propenyl, 1E-butenyl or 1E-pentenyl.

Especial preference is also given to compounds of the formula I which carry one or more alkenyl substituents.

Owing to asymmetrically substituted carbon atoms in the ring B, the compounds of the formula I can be in the form of stereoisomers. The invention relates to all isomers, both in pure form, as the racemate and also as a mixture of diastereomers or enantiomers. Optically active compounds of the formula I can also be used as dopants in liquid-crystal mixtures.

In the following schemes, the compounds of the formula IA are referred to for short as compounds 1 and those of the formula IB are referred to for short as compounds 2. For better legibility of the formulae, however, the square brackets and the parameters n and m are omitted. The rings $A^1$ and $A^2$ can thus also have the meaning of a single bond; and one of the groups $A^1$-$Z^1$ and $A^2$-$Z^2$ may also in each case occur twice, in which case the parameters which then occur twice may in each case, independently of one another, have one of the meanings indicated.

The compounds of the formula I are synthesised by two conceptually different routes. In the first route, route A (cf. scheme 1), the chroman structure is prespecified, and the furan moiety is built up starting from the former. For this purpose, suitable substituted 5-halochroman-6-ols 7 (X=Br, I) are used as synthetic building blocks. Sonogashira coupling to appropriately substituted terminal alkynes 8 generally proceeds with direct cyclisation and gives the compounds 1 of the formula I [DE 199 00 517 A1 and G. A. Gfesser, R. Faghih, Y. L. Bennani, M. P. Curtis, T. A. Esbenshade, A. A. Hancock, M. D. Cowart, *Biorg. Med. Chem. Lett.* 2005, 15, 2559-2563]. Depending on the nature of the alkyne 8, the conversion into the compounds 1 is advantageously carried out in two steps. Under the conditions of the Sonogashira coupling, the compounds 9 are firstly obtained as intermediates here. The cyclisation is then carried out on treatment with diethylzinc [M. Nakmura, L. Ilies, S. Otsubo, E. Nakamura, *Angew. Chem.* 2006, 118, 958-961; *Angew. Chem. Int Ed.* 2006, 45, 944-947].

Scheme I: Synthesis of the compounds 1 starting from chromans 7 (route A)

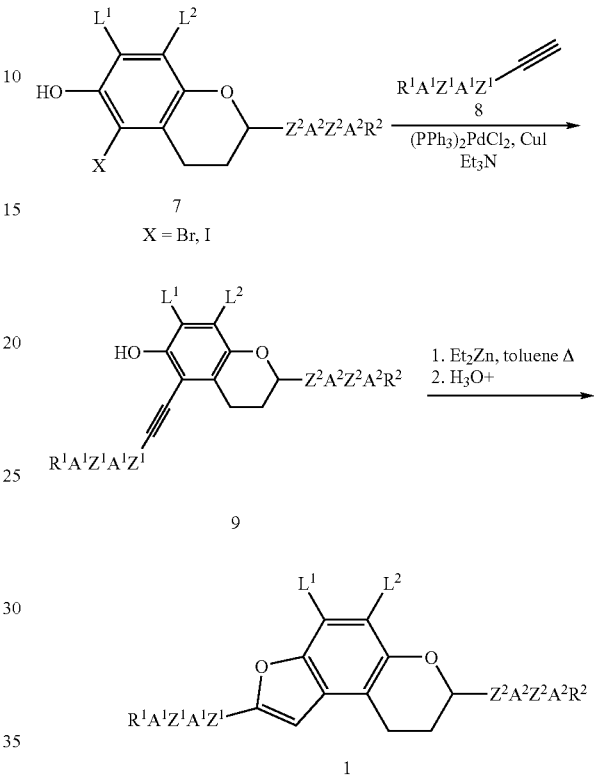

in which, as in the following schemes, unless explicitly indicated otherwise, the parameters have the respective meaning given above.

For the second route, route B (cf. scheme II), 2-substituted benzofuran-5-ols 10 are used as central intermediates. Compounds of type 1 are then obtained by anellation of a pyran ring. Starting from 10, this can either be carried out via a Claisen rearrangement [H. Ishii, T. Ishikawa, S. Takeda, S. Ueki, M. Suzuki, *Chem. Pharm. Bull.* 1992, 40, 1148-1153] or a reaction described by Wang and Finn [Q. Wang, M. G. Finn, *Org. Lett.* 2000, 2, 4063-4065].

The starting materials 14 for a Claisen rearrangement are obtained from 10 by Mitsunobu etherification [O. Mitsunobu, *Synthesis* 1981, 1] using propargyl alcohols 12, which are accessible, for example, by the addition reaction of lithium acetylide onto a corresponding aldehyde. On heating in N,N-diethylaniline, the aryl propargyl ethers 14 undergo a [3.3]-sigmatropic rearrangement to give the chromene derivatives 15. These can alternatively be synthesised from the salicylaldehyde derivatives 11. The compounds 11 are obtained by suitable formylation (cf. scheme II) of the benzofuran-5-ols 10. Conversion into the chroman 15 takes place via coupling to vinylboronic acids 13 [Q. Wang, M. G. Finn, *Org. Lett.* 2000, 2, 4063-4065]. Finally, the chromene double bond of the compounds 15 is selectively hydrogenated under mild conditions.

Scheme II: Synthesis of the compounds 1 starting from benzofuranols 10 (route B)

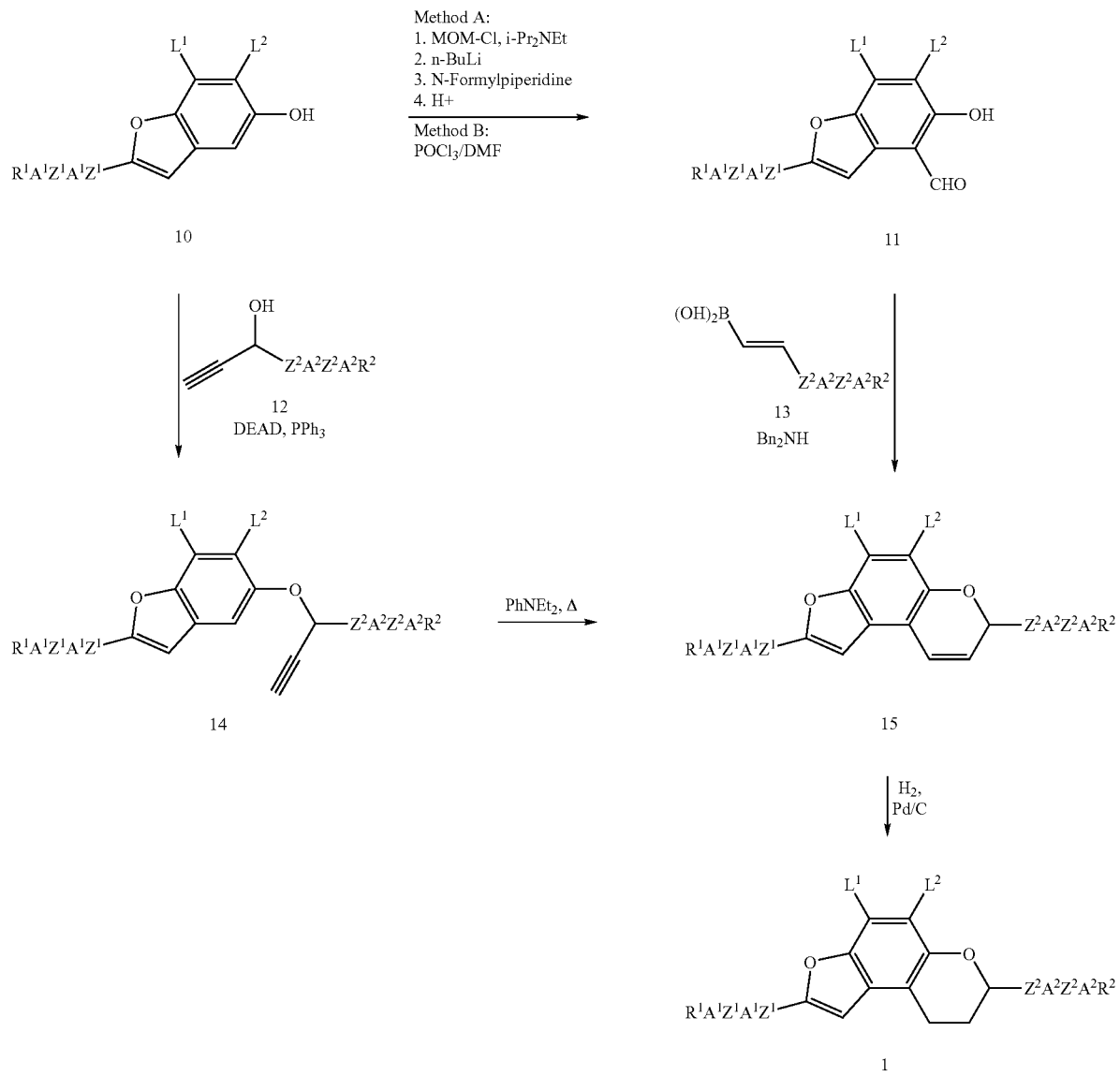

Compounds of type 2 are obtained directly from compounds of type 1 by hydrogenation of the 1,2-double bond (cf. scheme III).

Scheme III: Synthesis of the compounds 2 by hydrogenation of the compounds 1

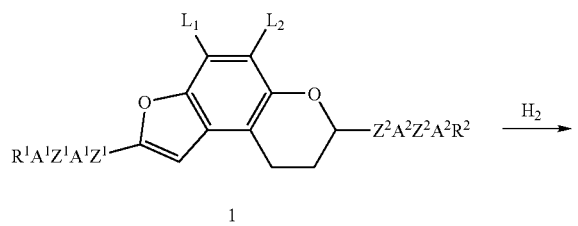

Alternatively, dihydrobenzofuranols 16 can also be utilised as starting materials for the synthesis of the compounds 2 (cf. scheme IV).

Scheme IV: Synthesis of the compounds 2 starting from dihydrobenzofuranols 16

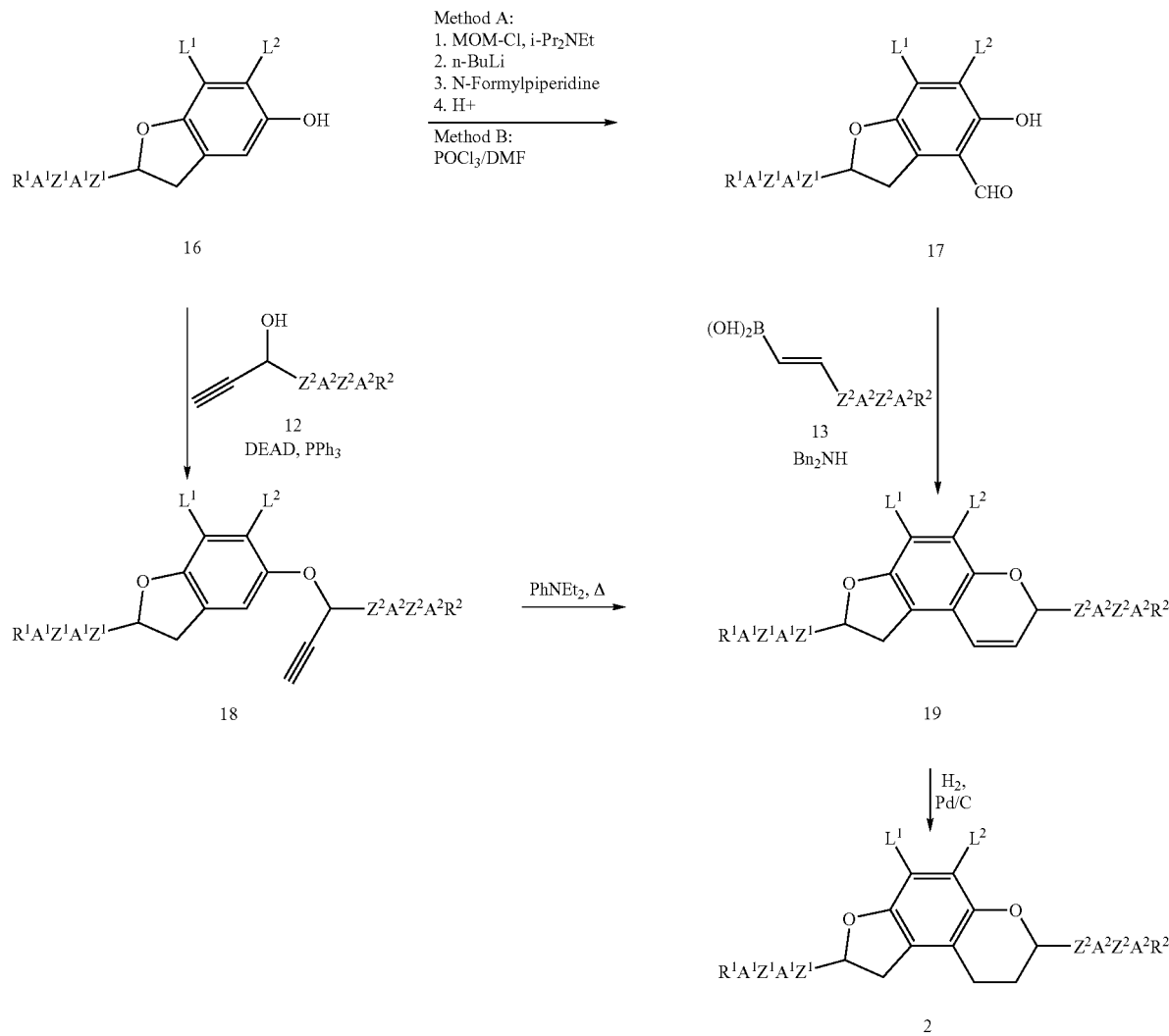

The synthesis can be adapted to the compounds of the formula I desired in each case through the choice of suitable starting materials 7 and 8 (route A, cf. scheme 1) or 10 and 12 or 13 (route B, cf. scheme II). The compounds of the formula II are then either obtained from the compounds 1 (cf. scheme III) or can be adapted to the compounds of the formula II desired in each case through the choice of suitable starting materials 16 and 12 or 13 (cf. scheme IV).

The starting materials 8 (route A, cf. scheme II), 12 and 13 (route B, cf. scheme II and scheme IV) are either commercially available or can be synthesised following processes that have already been published [for example *Methoden der organischen Chemie* [Methods of Organic Chemistry] (Houben-Weyl), Georg Thieme Verlag, Stuttgart, N.Y., 4th Edn. 1993].

The substitution pattern with respect to the radicals $L^1$ and $L^2$ in some cases makes particular requirements of the synthesis of the starting materials 7 (route A, cf. scheme 1), 10 (route B, cf. scheme II) and 16 (cf. scheme IV).

7,8-Difluoro-5-halochroman-6-ols 26 (X=Br, I, cf. scheme VI) are synthesised starting from 2,3-difluorophenol (20) or 3,4-difluoro-2-hydroxybenzaldehyde (23) [N. J. Lawrence, L. A. Hepworth, D. Rennison, A. T. McGown, J. A. Hadfield, *J. Fluorine Chem.* 2003, 123, 101-108 and E. Marzi, J. Gorecka, M. Schlosser, *Synthesis* 2004, 1609-1618] (cf. scheme V).

To this end, a propargyl aryl ether 21 is firstly formed from 2,3-difluorophenol (20) and a propargyl alcohol 12 by Mitsunobu etherification [O. Mitsunobu, *Synthesis* 1981, 1-28] and then undergoes a thermal [3.3]-sigmatropic rearrangement under suitable reaction conditions to give a 2H-chromene. These chromenes can easily be hydrogenated under gentle conditions to give the corresponding chromans 22.

Alternatively, these 7,8-difluorochromans 22 are obtained from 3,4-difluoro-2-hydroxybenzaldehyde (23) [N. J. Lawrence, L. A. Hepworth, D. Rennison, A. T. McGown, J. A. Hadfield, *J. Fluorine Chem.* 2003, 123, 101-108 and E. Marzi, J. Gorecka, M. Schlosser, *Synthesis* 2004, 1609-1618] via a reaction described by Wang and Finn [Q. Wang, M. G. Finn, *Org. Lett.* 2000, 2, 4063-4065]. 2H-chromenes, such as 24, are obtained in high yield here from salicylaldehydes and vinylboronic acids in the presence of dibenzylamine and can then in turn easily be hydrogenated to give the corresponding chromans 22 (see above).

Scheme V: Synthesis of substituted 7,8-difluorochromans 22

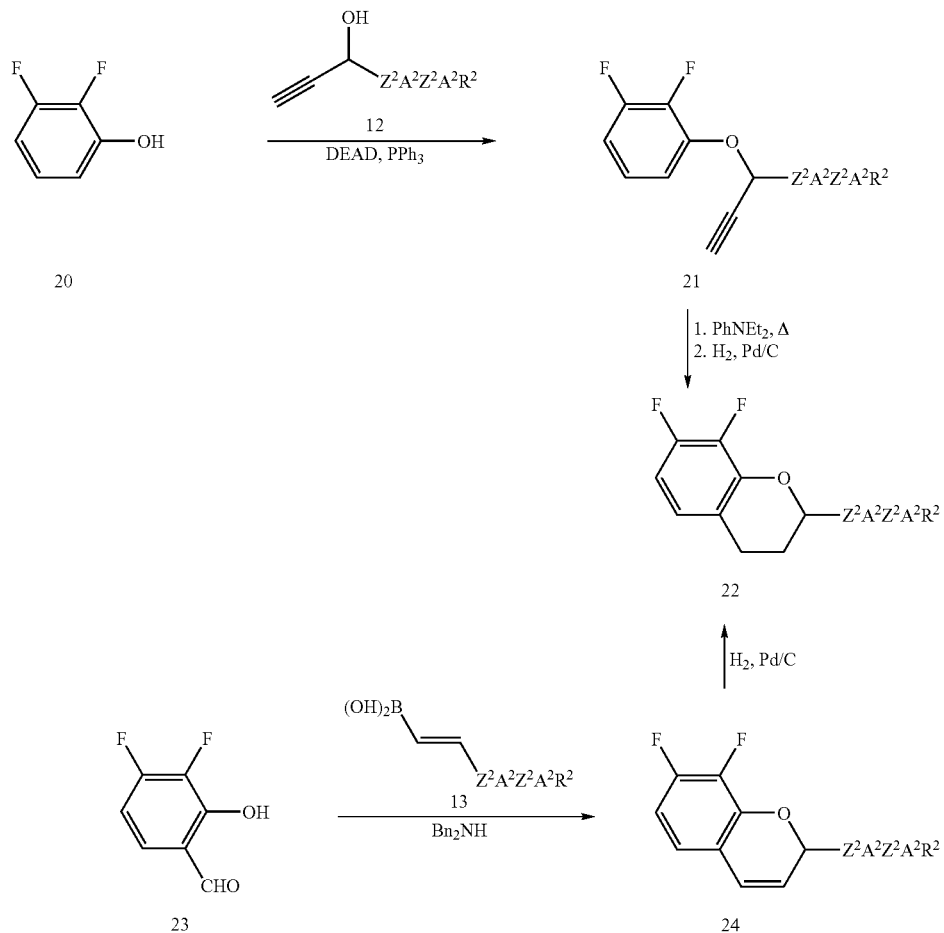

The intermediates 22 obtained in this way are functionalised by ortho-metallation and hydrolysis and oxidation of the boronic acid ester formed in situ to give chromanols 25 (cf. scheme VI). Final halogenation of the 5-position takes place via the reaction sequence depicted in scheme VI. The MOM ethers prepared from the compounds 25 are ortho-metallated using n-BuLi and quenched using iodine (or bromine for X=Br) [E. Marzi, J. Gorecka, M. Schlosser, *Synthesis* 2004, 1609-1618 and R. C. Ronald, M. R. Winkle, *Tetrahedron* 1983, 39, 2031-2042 and M. Lang, W. Steglich, *Synthesis* 2005, 1019-1027]. Removal of the MOM group gives the desired intermediates 26.

Scheme VI: Synthesis of 7,8-difluoro-5-halochroman-6-ols 26 (X = Br, I)

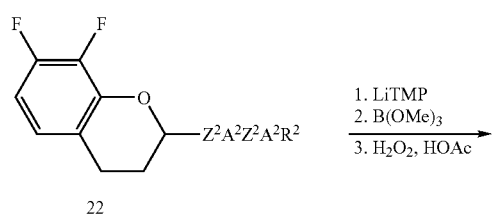

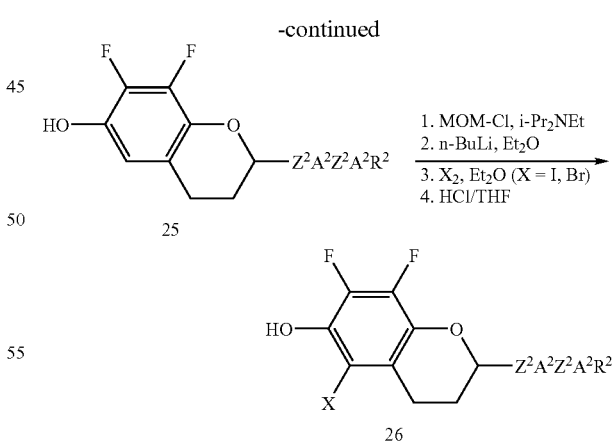

7-Fluoro-5-halochroman-6-ols 31 (X=Br, I) can be synthesised from 5-bromo-4-fluoro-2-hydroxybenzaldehyde (27) [J. B. Blair et al., *J. Med. Chem.* 2000, 43, 4701-4710 and W. A. Caroll et al., *J. Med. Chem.* 2004, 47, 3163-3179] (cf. scheme VII). This starting material 27 is accessible via processes known from the literature from 3-fluorophenol by ortho-selective formylation [J. B. Blair et al., *J. Med. Chem.*

2000, 43, 4701-4710] and subsequent bromination [W. A. Caroll et al., *J. Med. Chem.* 2004, 47, 3163-3179].

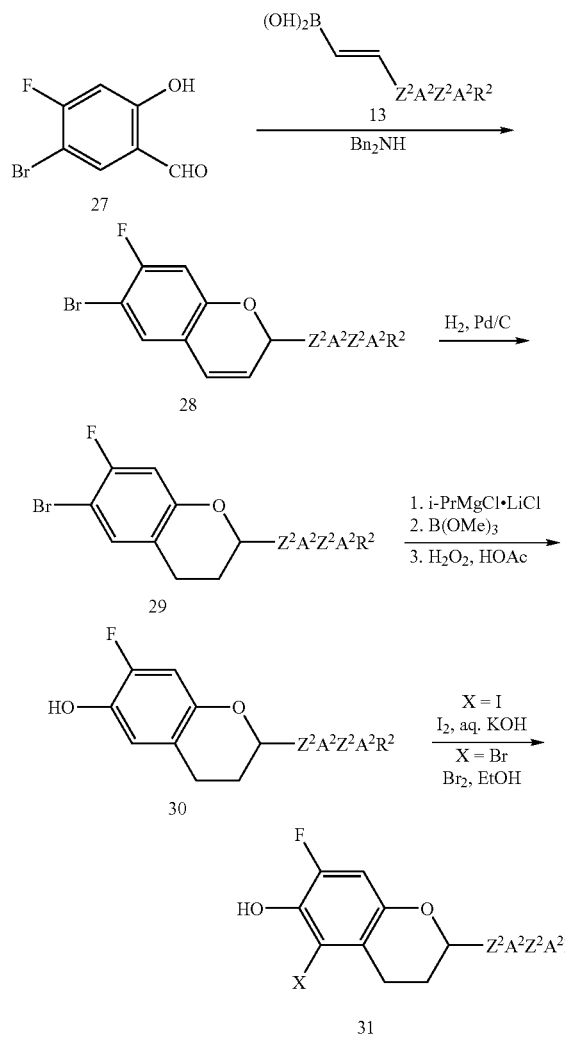

Starting from 5-bromo-4-fluoro-2-hydroxybenzaldehyde (27), the synthesis of the 7-fluorochromans 31 (cf. scheme VII) is in turn advantageously carried out by the coupling to vinylboronic acids already described [Q. Wang, M. G. Finn, *Org. Lett.* 2000, 2, 4063-4065] and subsequent hydrogenation. The functionalisation to give the chromanol 30 is carried out as described above, this time via the Grignard compound formed from 29. Final iodination (or bromination) can be carried out as above via the MOM ethers of the compounds 30, but is advantageously also carried out by direct iodination [G. A. Gfesser, R. Faghih, Y. L. Bennani, M. P. Curtis, T. A. Esbenshade, A. A. Hancock, M. D. Cowart, *Biorg. Med. Chem. Lett.* 2005, 15, 2559-2563, M. Lang, W. Steglich, *Synthesis* 2005, 1019-1027 and C. W. Holzapfel, D. B. G. Williams, *Tetrahedron* 1995, 51, 8555-8564, K. J. Edgar, S. N. Falling, *J. Org. Chem.* 1990, 55, 5287-5291 and R. Johnsson, A. Meijer, U. Ellervik, *Tetrahedron* 2005, 61, 11567-11663] (or bromination [B. F. Bonini, P. Carboni, G. Gottarelli, S. Masiero, G. P. Spada, *J. Org. Chem.* 1994, 59, 5930-5936]) of the chromanols 30.

8-Fluoro-5-halochroman-6-ols 36 (where X=Br, I) are obtained starting from 2-fluoro-4-bromophenol (32). Here, the O-heterocycle is preferably anellated by a Claisen rearrangement via the propargyl aryl ethers 33 (cf. scheme VIII). The functionalisation to give the chromanol 35 is carried out with the same reaction sequence as for the regioisomer 29. The halogenation of 35 gives principally the desired isomers 36 (X=Br, I), which can be separated off from undesired regioisomers via laboratory-typical purification methods.

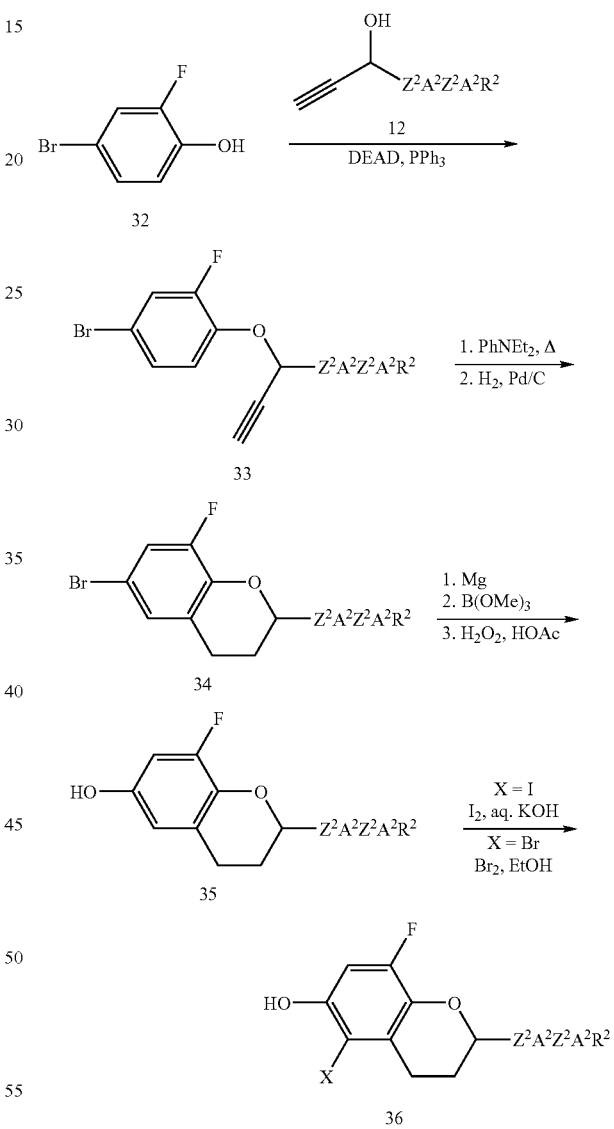

Alternatively, the intermediates 34 can also be synthesised starting from 2-fluoro-4-bromophenol (32) via the salicylaldehyde 37. The latter is accessible from 32 via a Duff reaction [M. L. Micklatcher, M. Cushman, *Synthesis* 1999, 1878-1880]. The subsequent synthesis of the chroman 34 can then be carried out via the procedure described by Wang and Finn [Q. Wang, M. G. Finn, *Org. Lett.* 2000, 2, 4063-4065] and subsequent hydrogenation (scheme IX).

Scheme IX: Synthesis of the intermediates 34

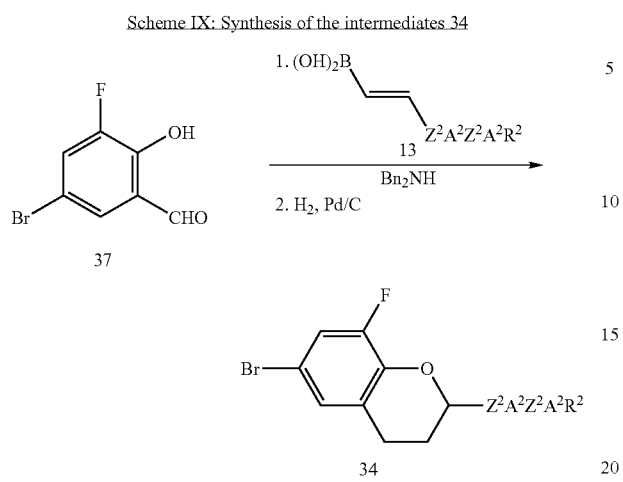

Non-fluorinated synthetic building blocks 41 can likewise be synthesised by the methods described above (Claisen rearrangement or coupling to vinylboronic acids). A particularly preferred process starts from 2,5-dihydroxybenzaldehyde (38), which is firstly brominated by methods known from the literature [Y. Hu, C. Li, B. A. Kulkarni, G. Strobel, E. Lokovsky, R. M. Torczynski, J. A. Porco, *Org. Lett.* 2001, 3, 1649-1652] and selectively protected (cf. scheme X). After two-step conversion into the chroman 40, removal of the TBS group gives the bromide 41 (X=Br), which serves as starting material for the subsequent Sonogashira couplings. In some cases, the Sonogashira coupling to corresponding aryl iodides 41 (X=I) is particularly advantageous. These compounds 41 (X=I) are likewise accessible from the bromochroman 40 via the reaction sequence depicted in scheme X comprising halogen-metal exchange, scavenging using iodine and removal of the protecting group using fluoride.

Scheme X: Synthesis of the intermediates 41

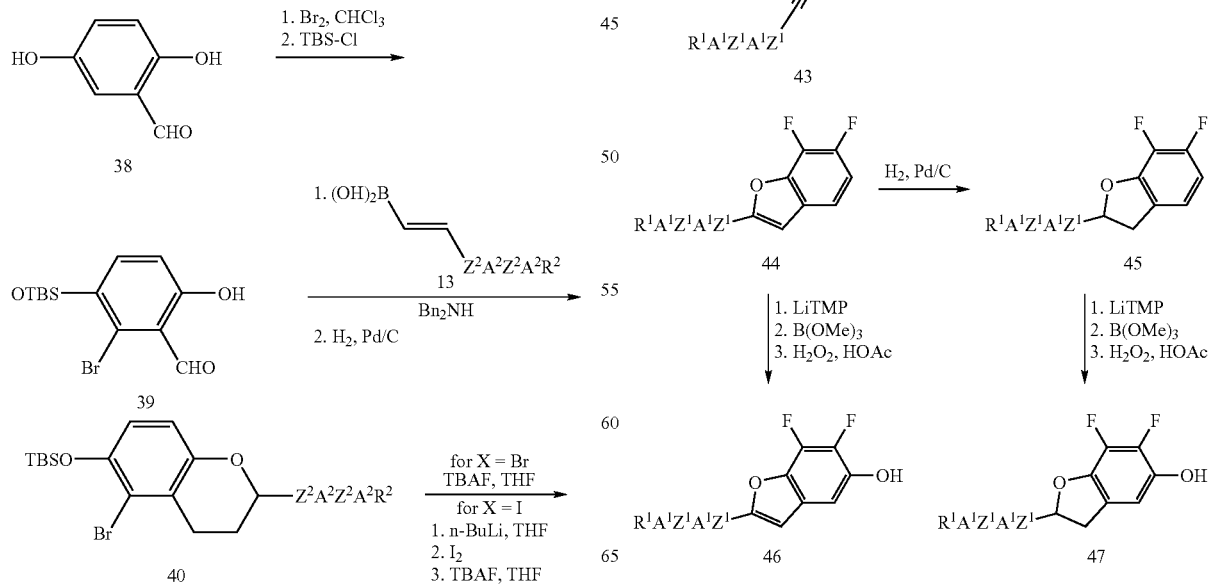

Suitable substituted 6,7-difluorobenzofuran-5-ols 46 and 6,7-difluoro-2,3-dihydrobenzofuran-5-ols 47 can be obtained as follows (scheme XI).

Scheme XI: 6,7-Difluorobenzofuran-5-ols 46 and 6,7-difluoro-2,3-dihydro-benzofuran-5-ols 47

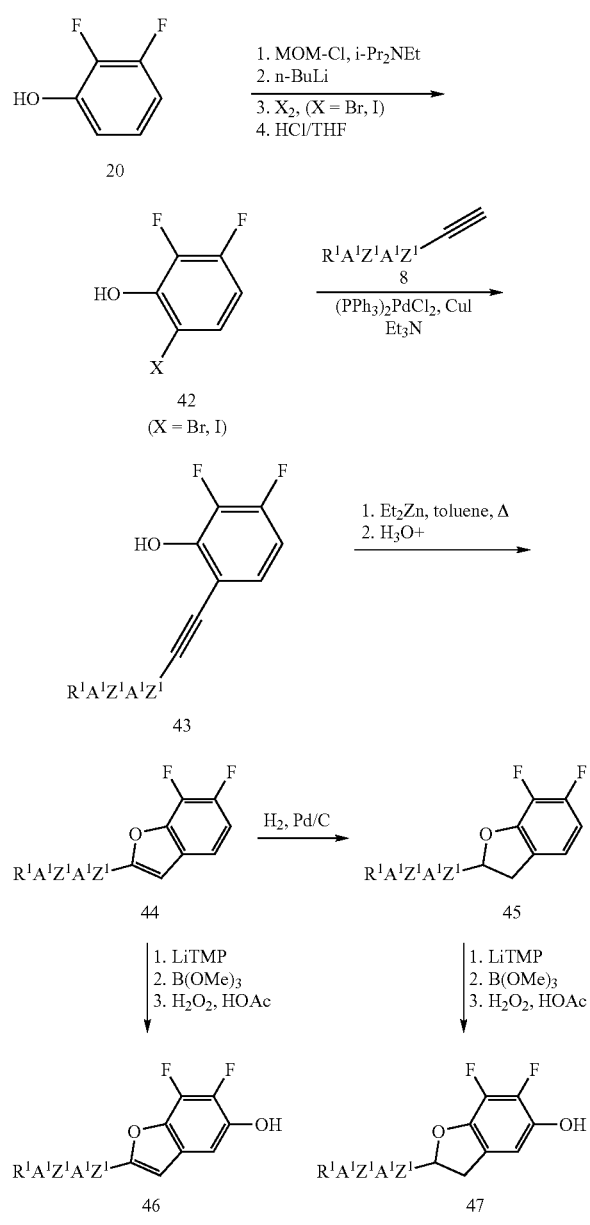

2,3-Difluoro-6-halophenols 42 are advantageously synthesised from 2,3-difluorophenol (20) via the reaction sequence already explained. The 2-substituted benzofurans 44 are either formed directly in a Sonogashira coupling to a suitable alkyne 8 or are obtained via the intermediate 43 and subsequent cyclisation using diethylzinc (cf. scheme 1). These be prepared by conceptually similar routes. In contrast to the above, corresponding 4-bromophenols 48 are selected as starting materials. The functionalisation to give the benzofuranols 53 and 54 is then not carried out by ortho-metallation, but instead via the Grignard reagents obtained from compounds 51 and 52 (cf. scheme XII).

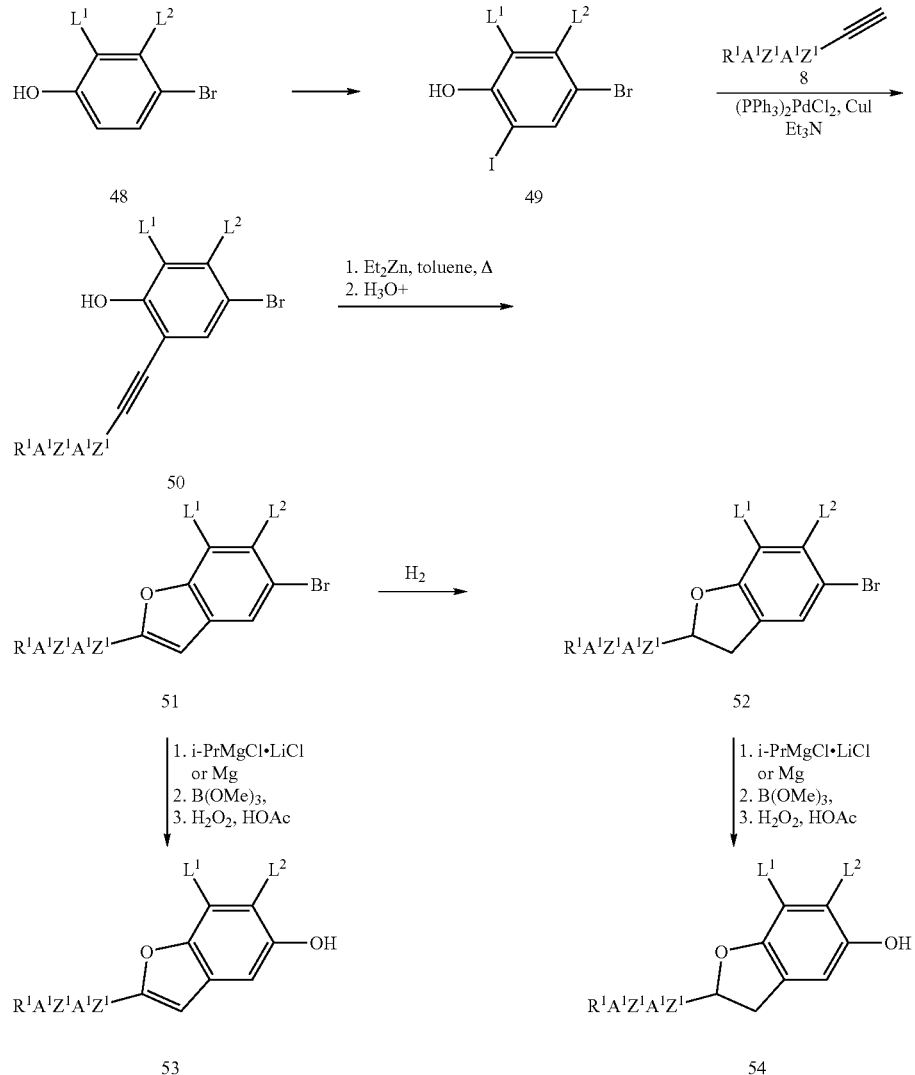

benzofurans 44 can readily be hydrogenated to the corresponding dihydrobenzofurans 45. The 6,7-difluorobenzofuran-5-ols 46 or 6,7-difluoro-2,3-dihydrobenzofuran-5-ols 47 necessary for the reaction sequences depicted in scheme II and scheme IV are obtained from 44 or 45 respectively by ortho-metallation, hydrolysis and oxidation of the boronic acid ester formed in situ.

6-Fluorobenzofuran-5-ols 53 (where $L^1$=H and $L^2$=F) or 6-fluoro-2,3-dihydrobenzofuran-5-ols 54 (where $L^1$=H and $L^2$=F), 7-fluorobenzofuran-5-ols 53 (where $L^1$=F and $L^2$=H) or 7-fluoro-2,3-dihydrobenzofuran-5-ols 54 (where $L^1$=F and $L^2$=H) and benzofuran-5-ols 53 (where $L^1$=H and $L^2$=H) or 2,3-dihydrobenzofuran-5-ols 54 (where $L^1$=H and $L^2$=H) can For the specific case where $R^1A^1Z^1A^1Z^1$ denotes methyl and $L^1$ and $L^2$ denote F, a suitably functionalised benzofuran 60 can be prepared particularly simply via a [3.3]-sigmatropic rearrangement starting from 56 (cf. scheme XIII). 56 is prepared from 5-bromo-2,3-difluorophenol (55) and propargyl bromide. Heating in N,N-diethylaniline in the presence of caesium fluoride [H. Ishii, T. Ishikawa, S. Takeda, S. Ueki, M. Suzuki, T. Harayama, *Chem. Pharm. Bull.* 1990, 38, 1775-1777 and A. Chilin, P. Rodighiero, A. Guiotto, *Synthesis* 1998, 309-312] gives the benzofuran 57. The functionalisation to give the salicylaldehyde 60 is then carried out via a combination of the standard methods already explained above. The sub-sequent procedure can then be carried out as depicted above in scheme II.

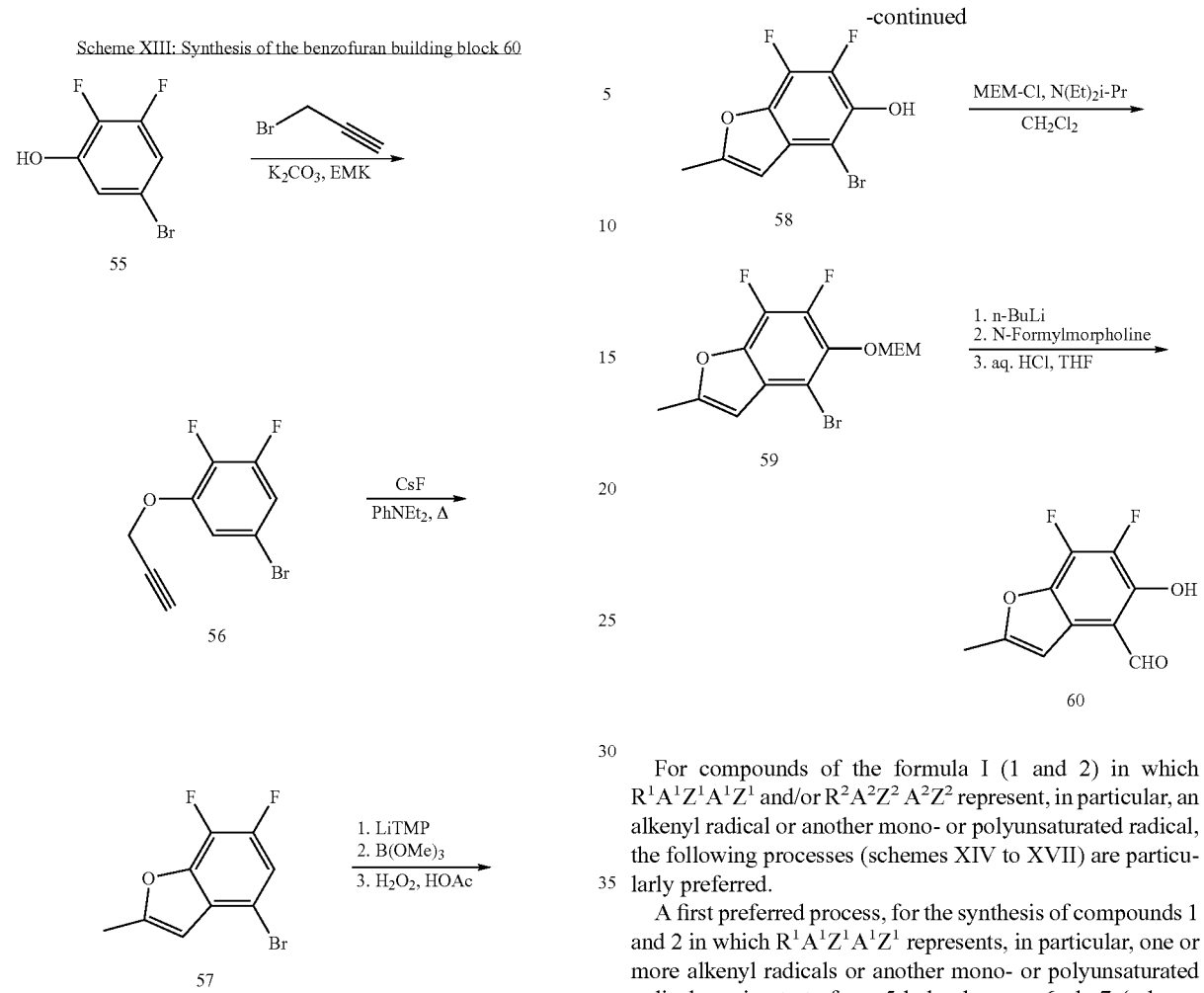

For compounds of the formula I (1 and 2) in which $R^1A^1Z^1A^1Z^1$ and/or $R^2A^2Z^2A^2Z^2$ represent, in particular, an alkenyl radical or another mono- or polyunsaturated radical, the following processes (schemes XIV to XVII) are particularly preferred.

A first preferred process, for the synthesis of compounds 1 and 2 in which $R^1A^1Z^1A^1Z^1$ represents, in particular, one or more alkenyl radicals or another mono- or polyunsaturated radical, again starts from 5-halo-chroman-6-ols 7 (scheme XIV).

Scheme XIV: Synthesis of functionalisable intermediates 64 and 65 starting from 5-halochroman-6-ols 7

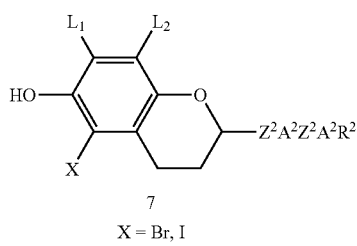

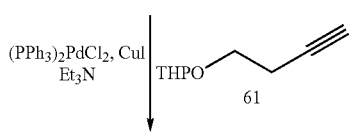

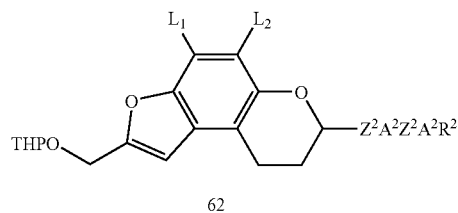

62

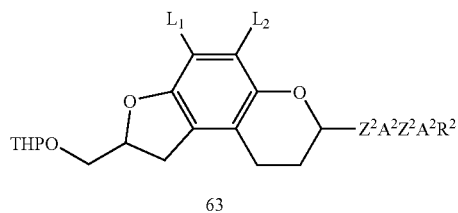

63

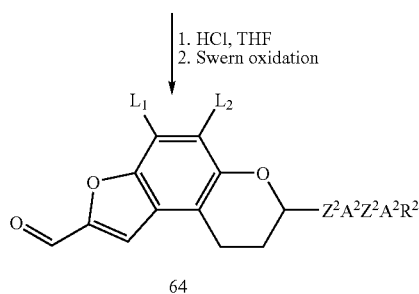

64

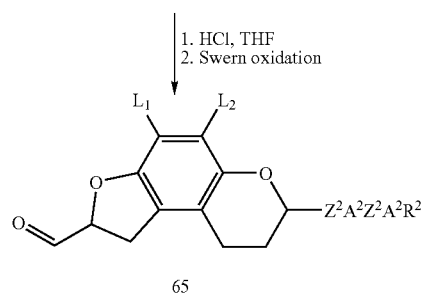

65

If the sequence comprising Sonogashira coupling and ring closure using THP-protected homopropargyl alcohol 61 [N. G. Kundu, M. Pal, J. S. Mahanty, M. De, *J. Chem. Soc. Perkin Trans* 1 1997, 19, 2815-2820] is carried out, the compounds 62 are obtained. Starting from the latter, cleavage of the THP ether and oxidation of the resultant primary alcohol [L. Capuano, S. Drescher, V. Hammerer, M. Hanisch, *Chem. Ber.* 1988, 121, 2259-2262] can give the functionalisable intermediate 64. Functionalisation thereof to give the compounds 1 can then be carried out, for example, by Wittig olefination (cf. scheme XV). A functionalisable intermediate 65 which results in the compounds 2 in this way (Wittig olefination, etc.) is obtained after hydrogenation of 62 to 63, subsequent THP cleavage and oxidation.

If it is intended to synthesise compounds of type 1 in which $R^1Z^1A^1Z^1A^1$ and $R^2A^2Z^2A^2Z^2$ contain unsaturated radicals, bridges or ring systems, correspondingly substituted 5-halochroman-6-ols 70 can be employed. The latter are accessible via the following process (cf. scheme XV) using the chroman-2-carbaldehydes 69 as central, functionalisable intermediates. Starting from salicylaldehydes 66 (Y=H, Br, cf. schemes V, VII and IX), the chromene 68 is built up with the boronic acid 67 [R. A. Batey, A. N. Avinash, A. J. Lough, *J. Am. Chem. Soc.* 1999, 121, 450-451]. Hydrogenation and oxidation gives the intermediate 69. Starting from the latter, the $R^2A^2Z^2A^2Z^2$ side chain can firstly then be built up; the subsequent functionalisation to give the 5-halochroman-6-ols 70, which can then be converted into the compounds 1 in accordance with scheme XIV, has already been described (cf. schemes V, VII and IX).

Scheme XV: Synthesis of specifically substituted 5-halochroman-6-ols 70

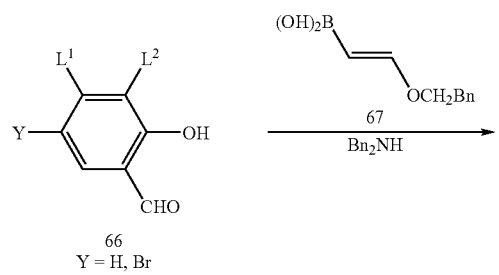

66
Y = H, Br

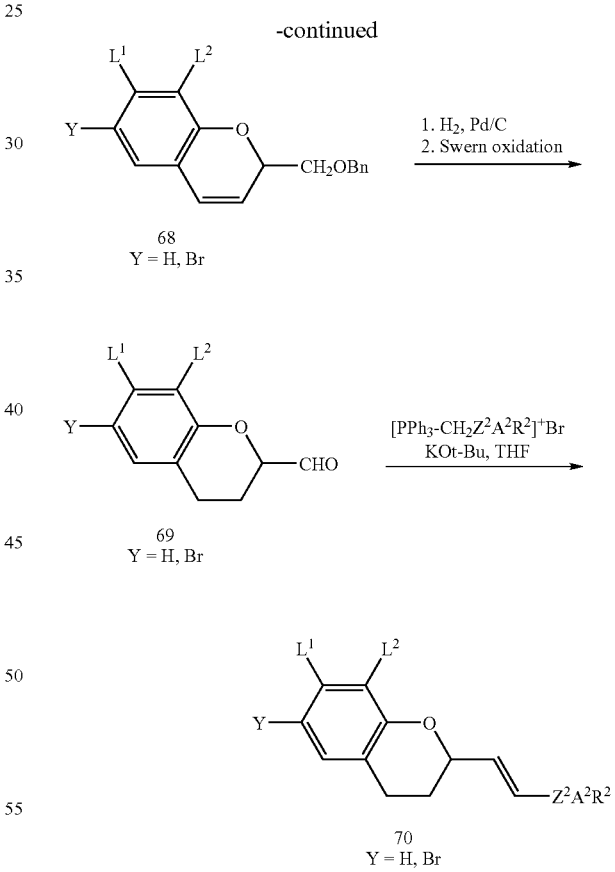

68
Y = H, Br

69
Y = H, Br

70
Y = H, Br

These substances are also suitable for the synthesis of compounds 2 in which $R^1Z^1A^1Z^1A^1$ and $R^2A^2Z^2A^2Z^2$ contain unsaturated radicals, bridges or ring systems. To this end, the following process is required in accordance with the literature procedure [J. C. González-Gómez, L. Santana, E. Uriarte, *Tetrahedron* 2005, 61, 4805-4810 and K. J. Hodgetts, *Tetrahedron* 2005, 61, 6860-6870] (cf. scheme XVI).

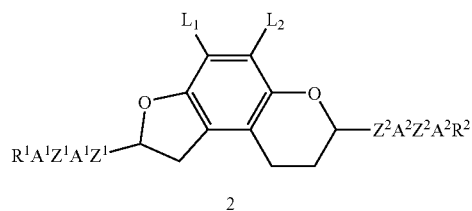
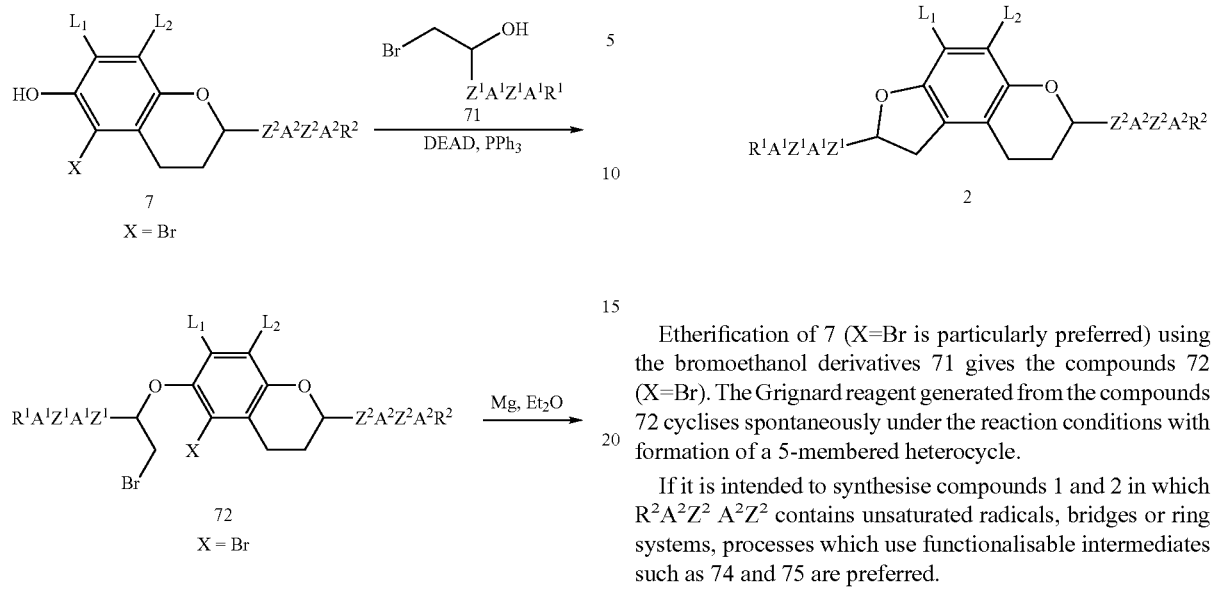

Etherification of 7 (X=Br is particularly preferred) using the bromoethanol derivatives 71 gives the compounds 72 (X=Br). The Grignard reagent generated from the compounds 72 cyclises spontaneously under the reaction conditions with formation of a 5-membered heterocycle.

If it is intended to synthesise compounds 1 and 2 in which $R^2A^2Z^2\ A^2Z^2$ contains unsaturated radicals, bridges or ring systems, processes which use functionalisable intermediates such as 74 and 75 are preferred.

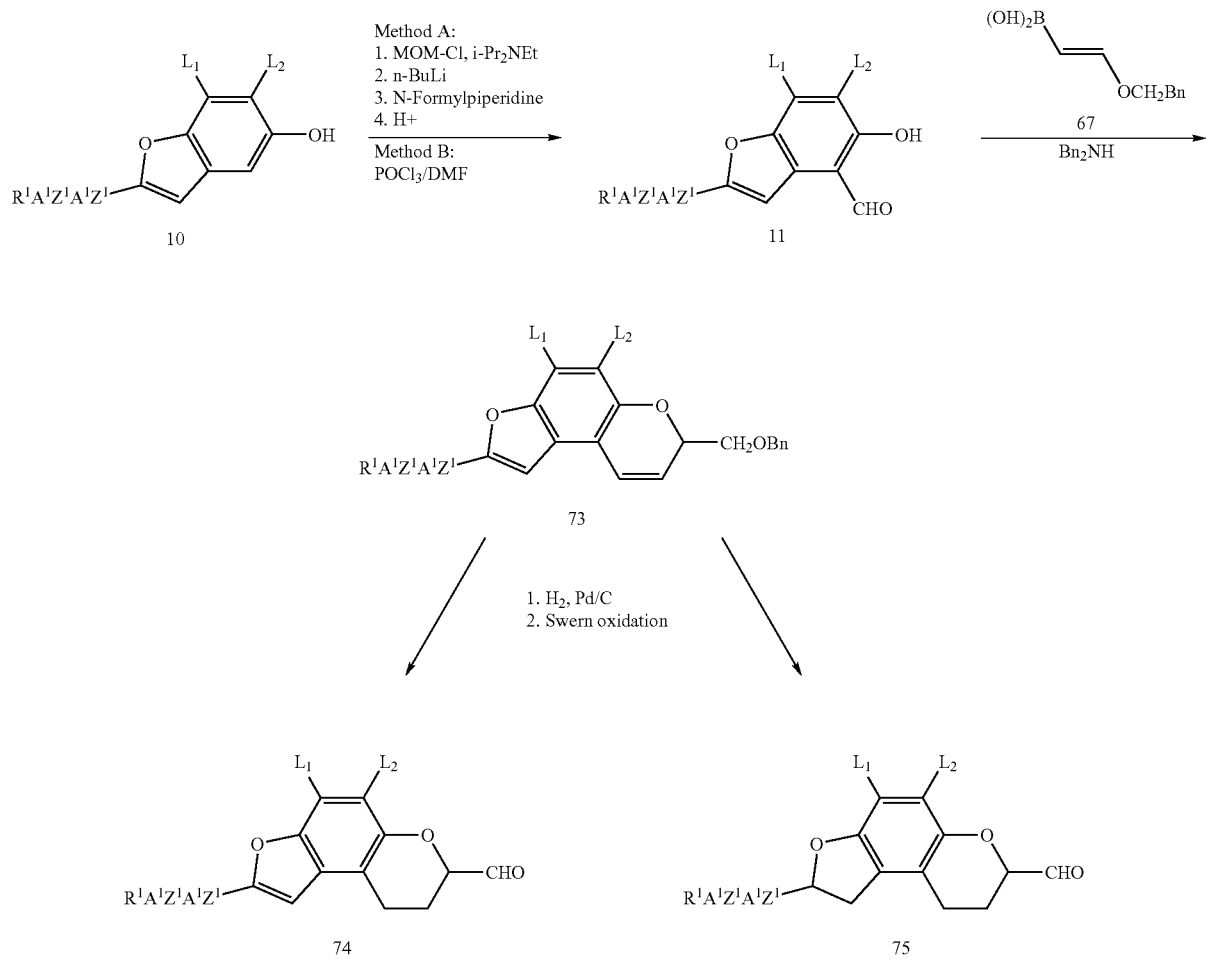

Starting from the salicylaldehyde derivatives 11 which have already been described above, the pyran moiety is built up using the boronic acid 67 [R. A. Batey, A. N. Avinash, A. J. Lough, *J. Am. Chem. Soc.* 1999, 121, 450-451] (cf. scheme XV). The chromene CC double bond is hydrogenated under mild conditions (1 atm of $H_2$, room temperature), and the benzyl ether is cleaved to give the corresponding alcohol. It is only at increased hydrogen pressure and elevated temperature that the hydrogenation of the 2,3-double bond also takes place. The alcohols formed are oxidised to the corresponding aldehydes, and the compounds 74 and 75 can then be functionalised to give compounds 1 and 2 as depicted, for example, in scheme XV.

Examples of structures of preferred compounds of the formula I are given below in sub-formula order, in which
$R^{11}$ and $R^{22}$ have the respective meaning given under formula I for $R^1$ and $R^2$ respectively,
p, and in the case where p occurs more than once, these independently of one another,
denotes 0, 1, 2, 3 or 4, preferably 0, 1 or 2, and preferably

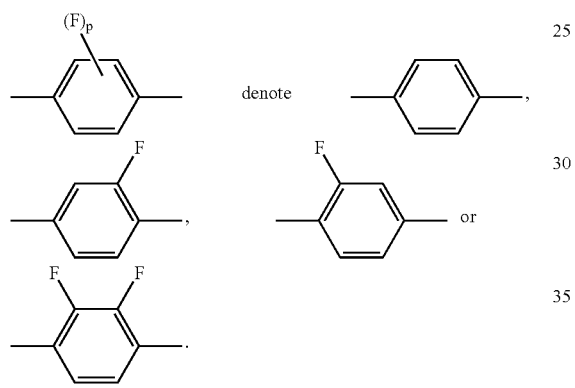

Of the compounds IA-1 to IA-11 and IB-1 to IB-11, particular preference is given to those having at least one fluorine substituent in the skeleton.

Very particular preference is given to compounds having two fluorine substituents in the skeleton.

Preferred compounds of the formulae IA-1 and IB-1 are:

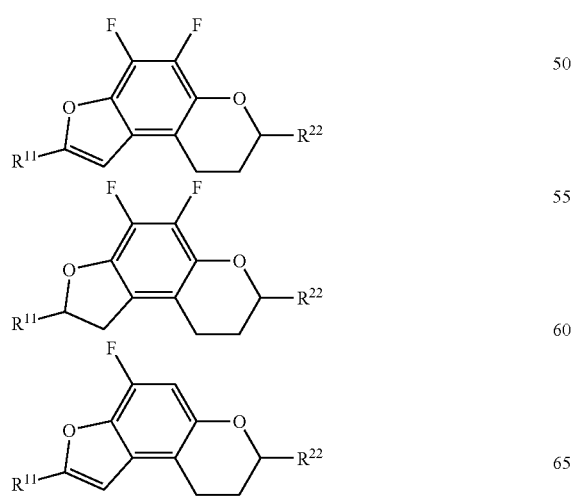

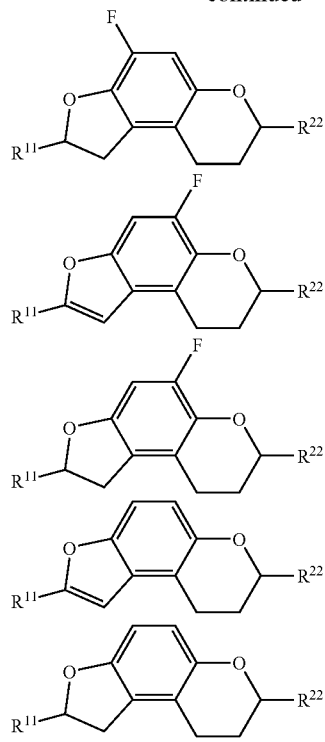

Preferred compounds of the formulae IA-2 and IB-2 are:

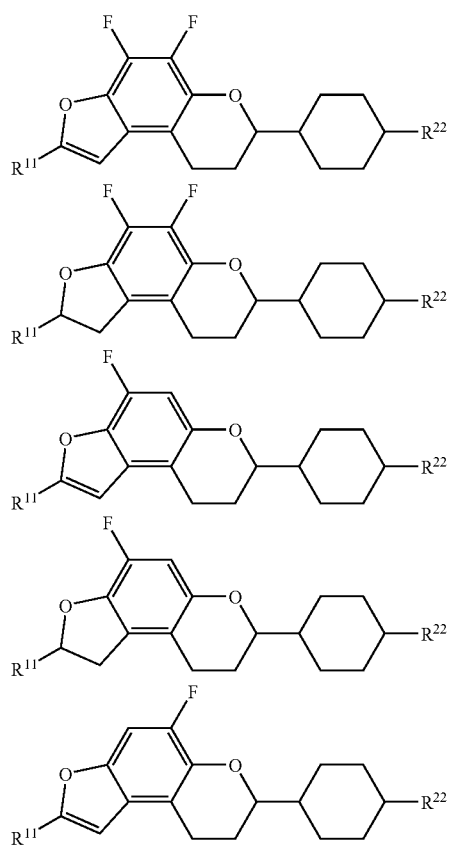

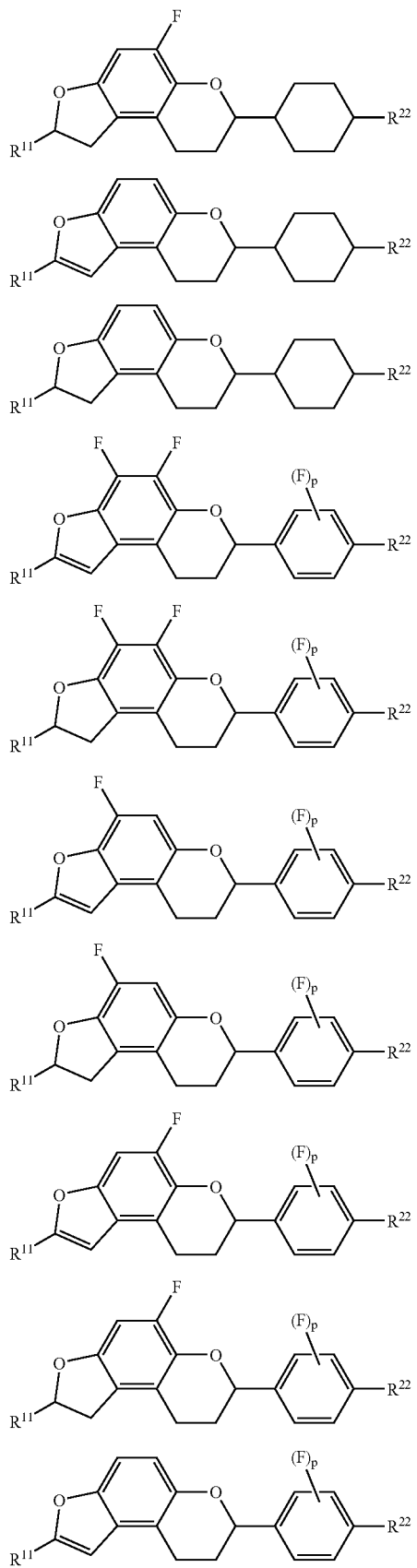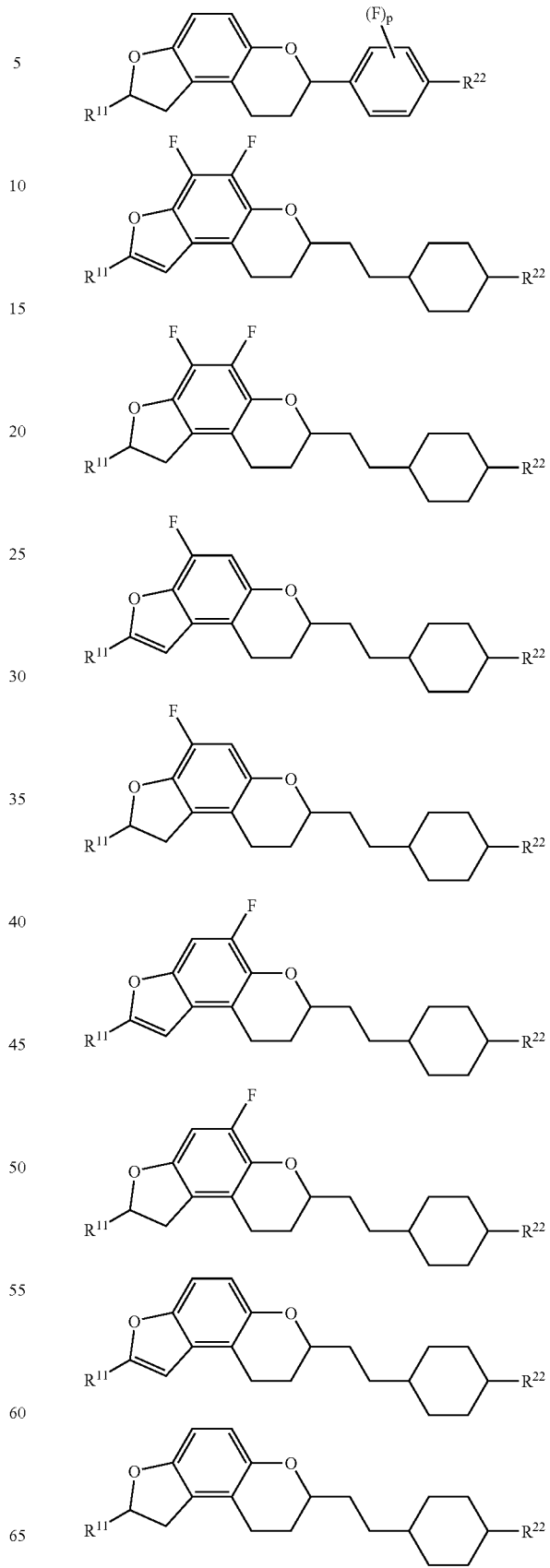

-continued
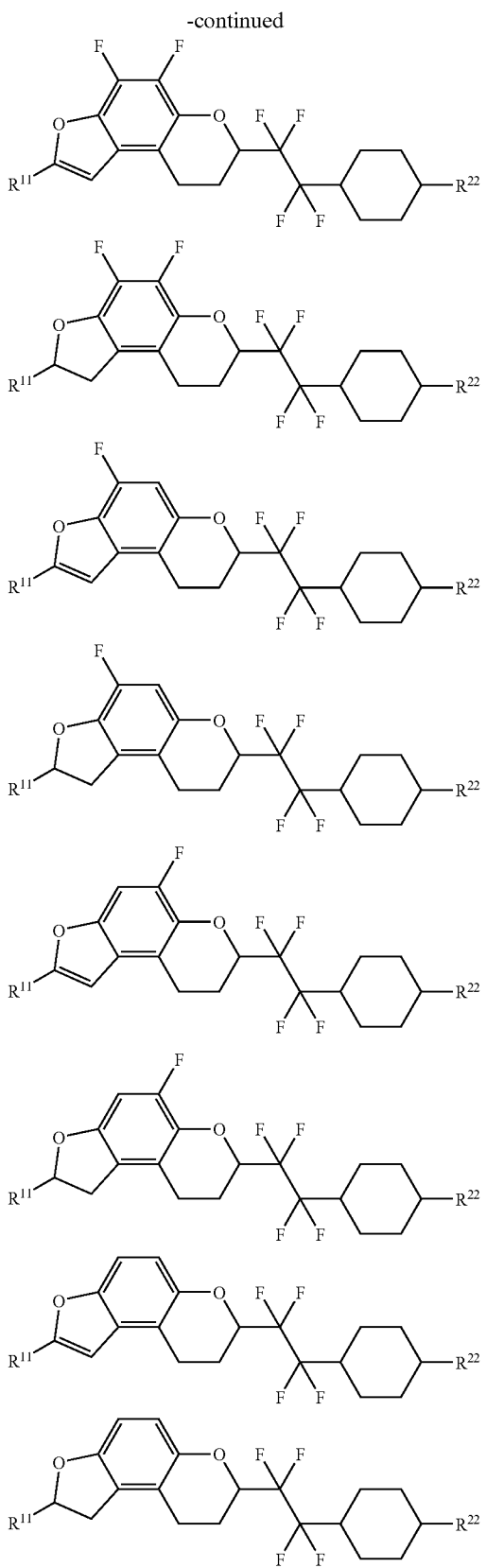
Of the compounds IA-2 and IB-2, particular preference is given to those containing a cyclohexyl ring.
Preferred compounds of the formulae IA-3 and IB-3 are:
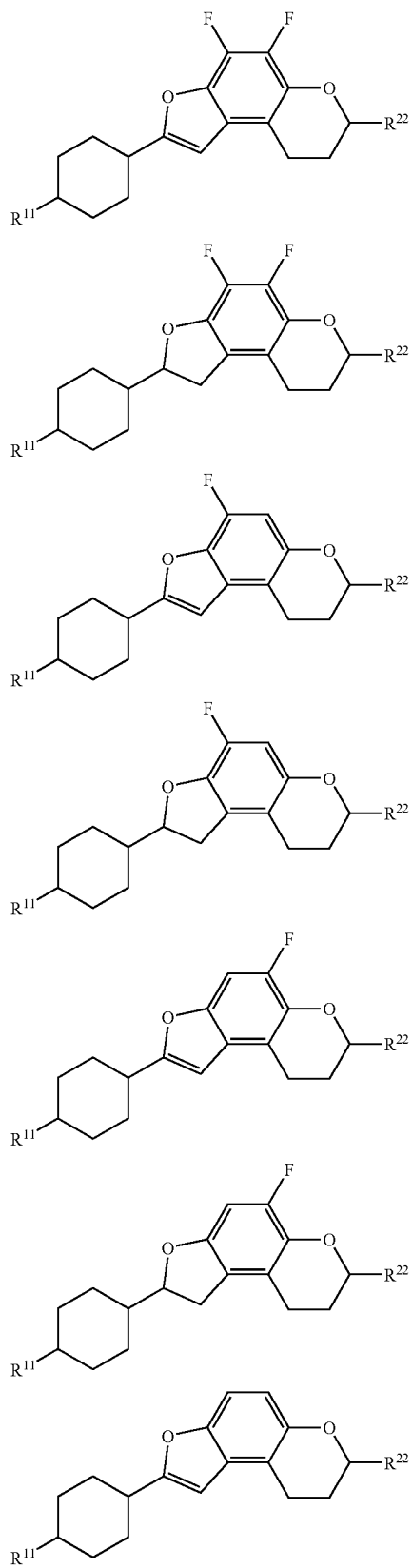

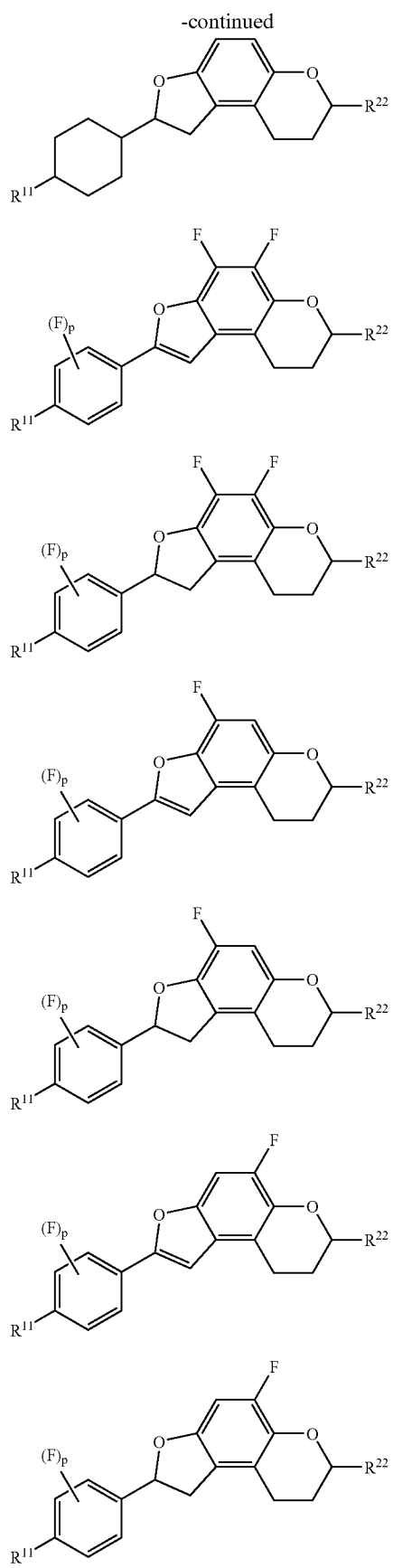
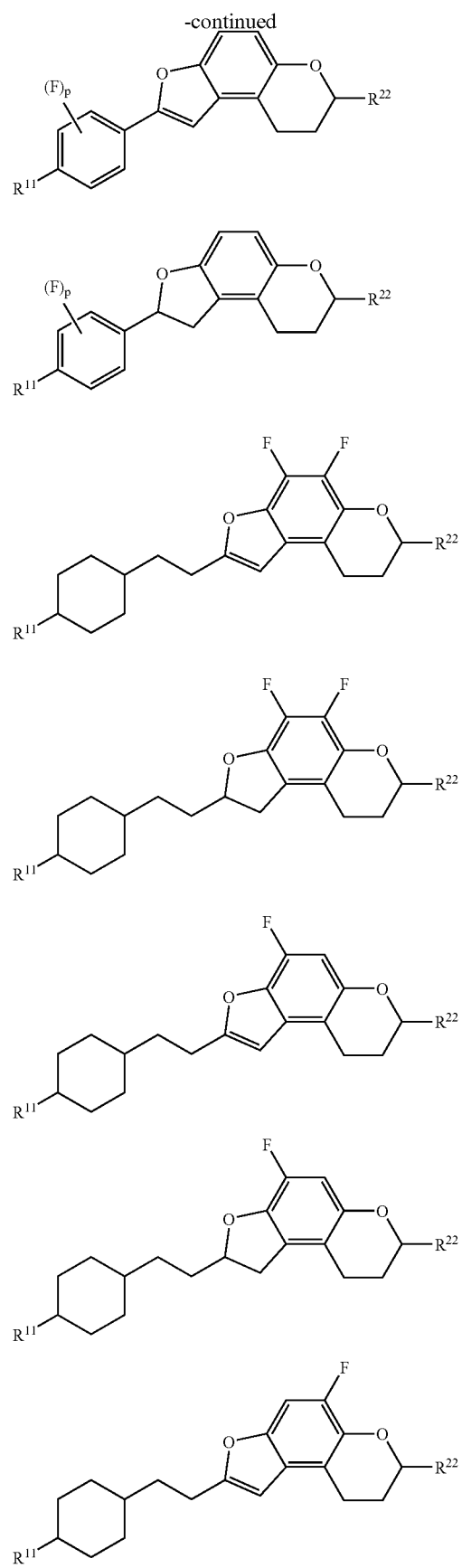

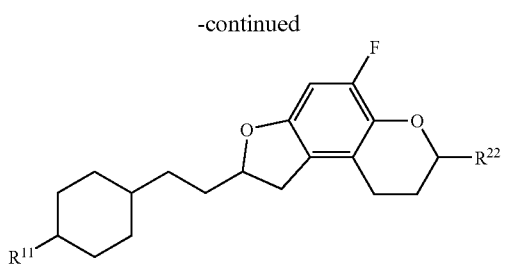
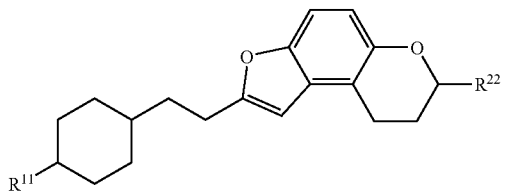
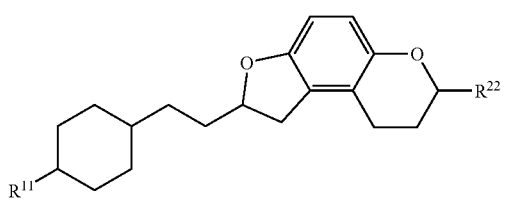
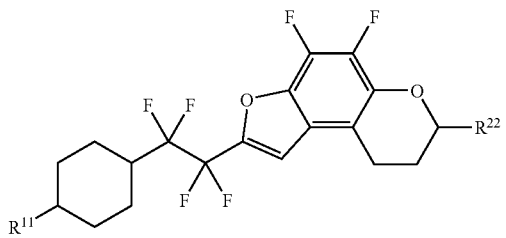
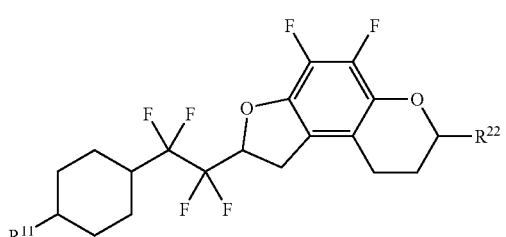
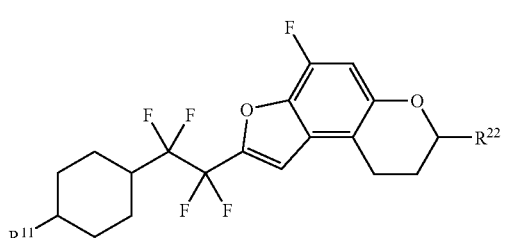
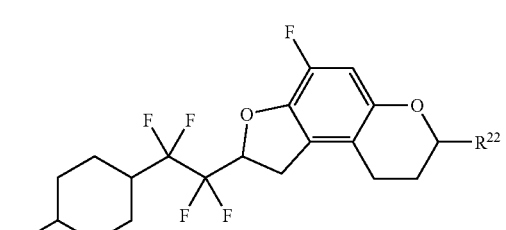
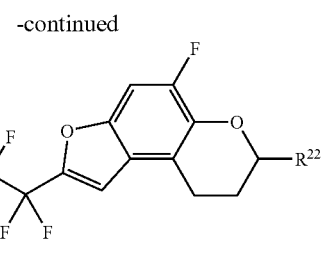
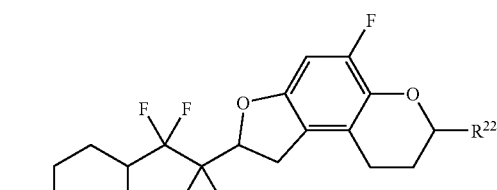
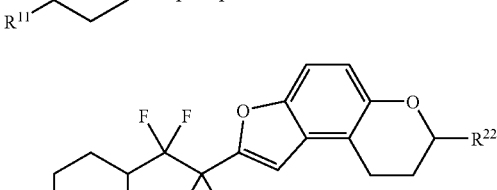
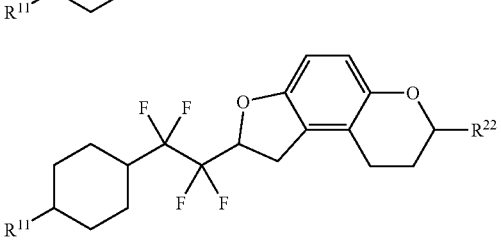
Of the compounds of the formula IA-3, compounds containing an unsubstituted or substituted 1,4-phenylene ring are preferred.
Of the compounds IB-3, particular preference is given to those containing a cyclohexyl ring.
Preferred compounds of the formulae IA-4 and IB-4 are:
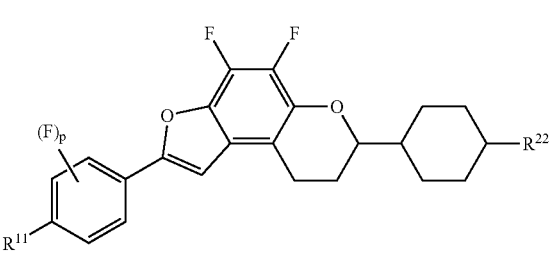
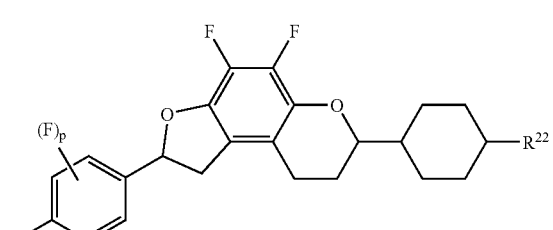

-continued
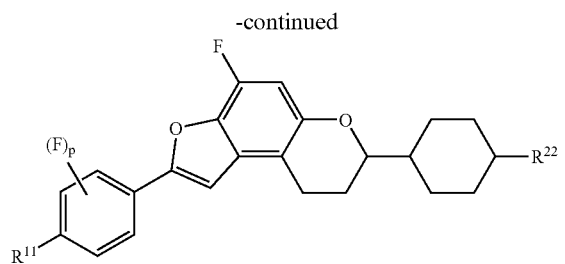
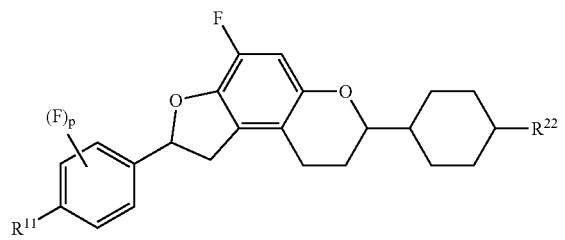
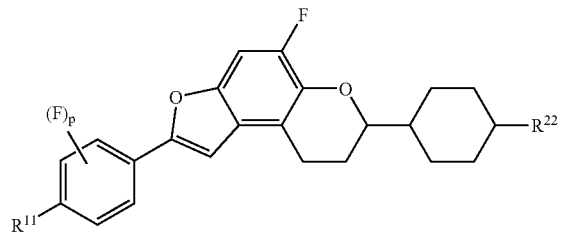
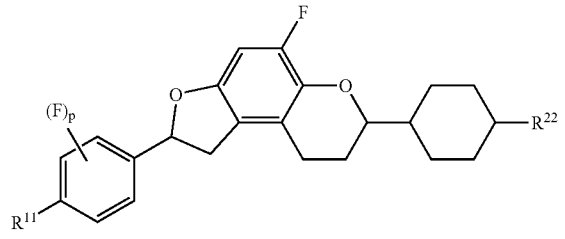
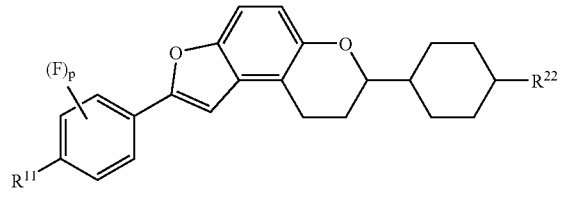
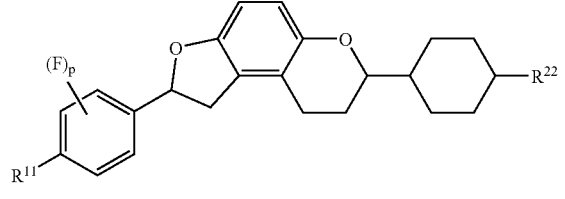
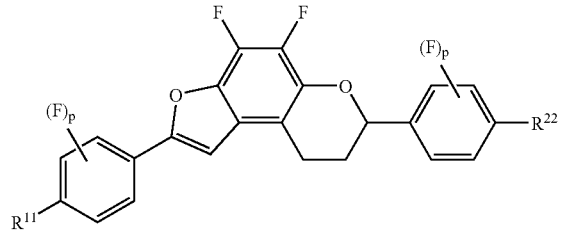
-continued
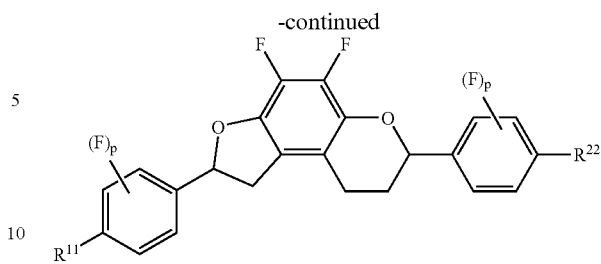
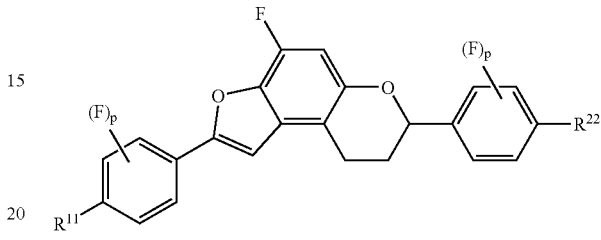
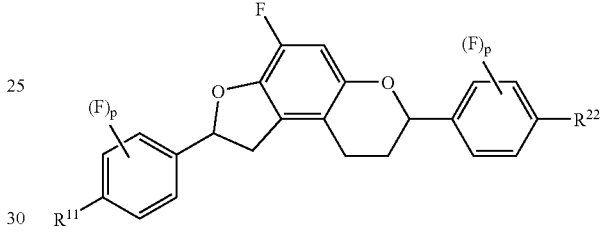
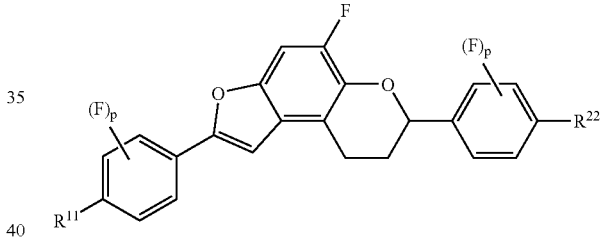
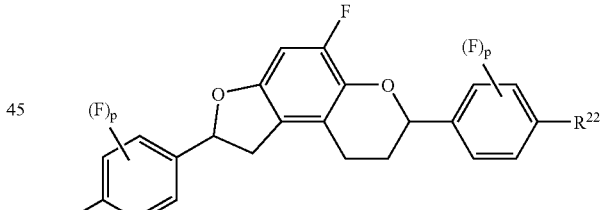
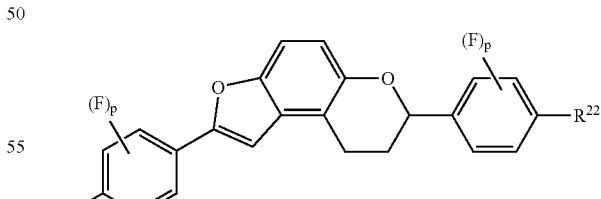
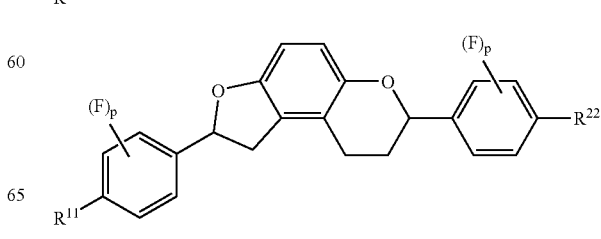

-continued
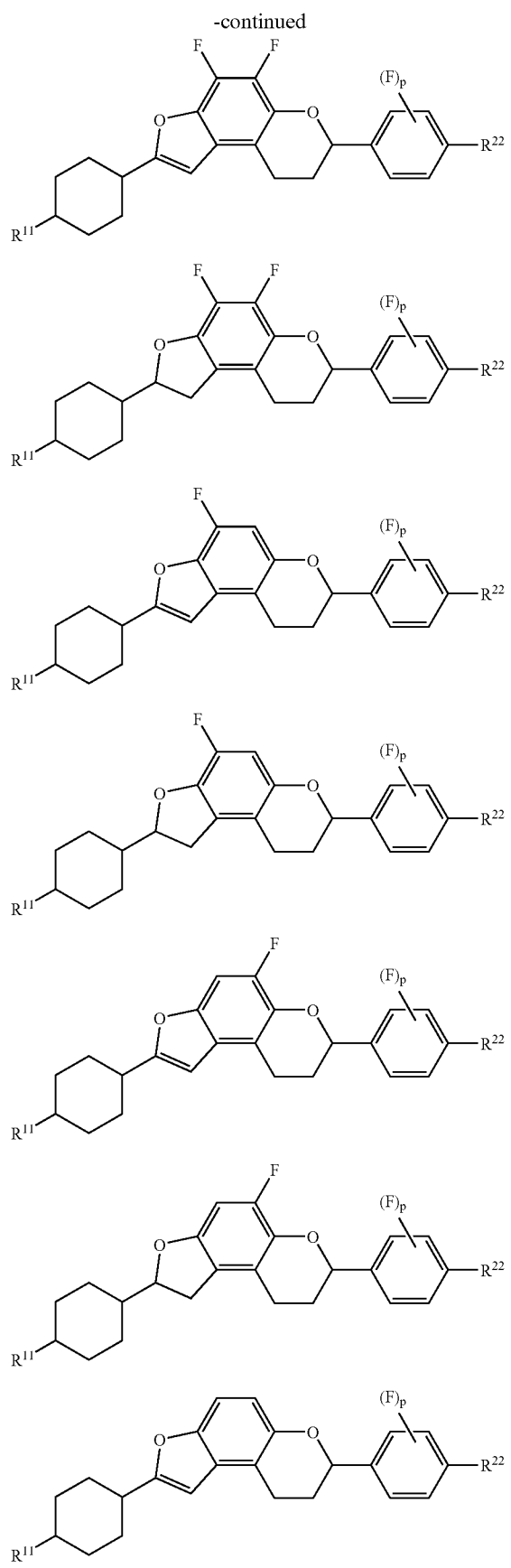
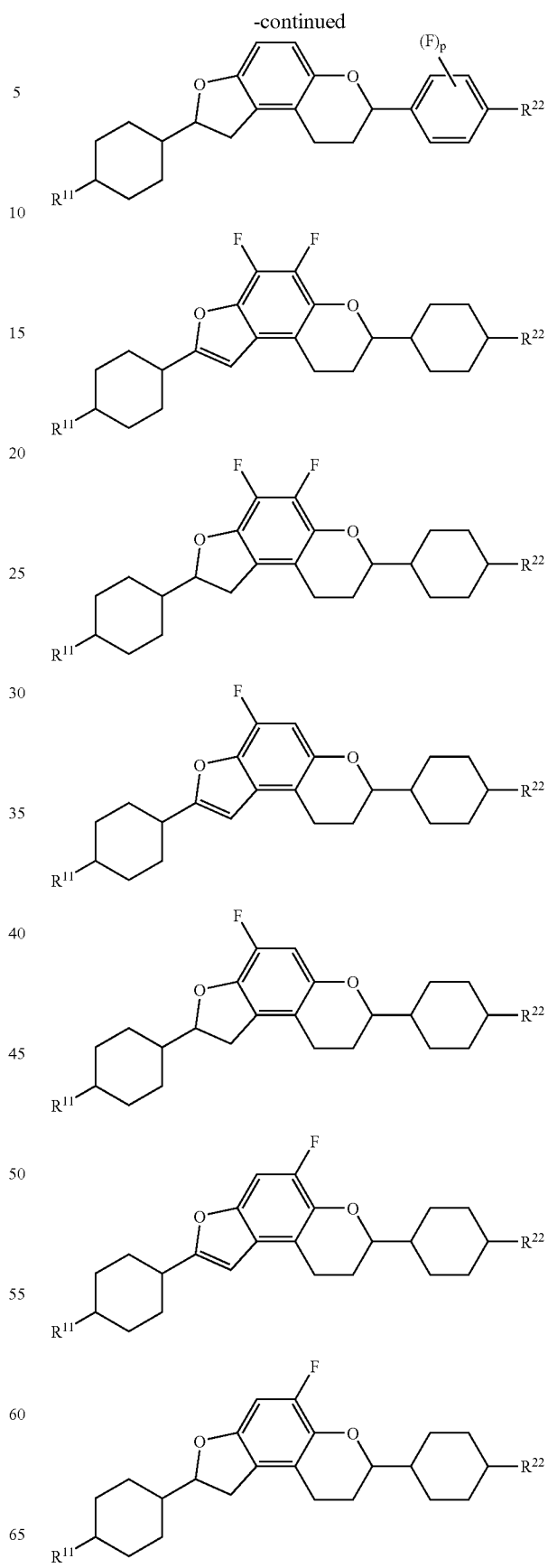

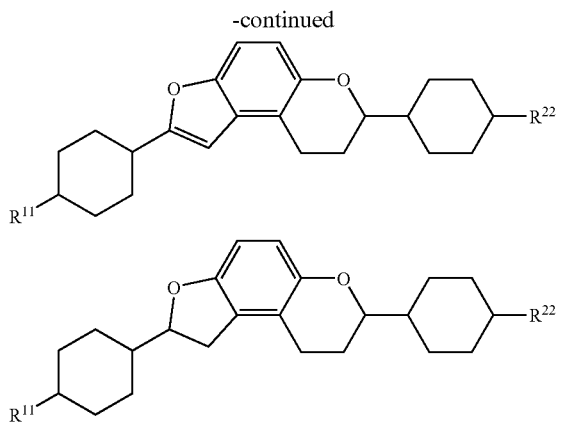

Of the compounds of the formula IA-4, particular preference is given to compounds of the formulae in which the skeleton is substituted on the left-hand side by a substituted or unsubstituted 1,4-phenylene ring and/or the skeleton is linked on the right-hand side to a cyclohexyl radical.

Of the compounds of the formula IB-4, preference is given to compounds of the formulae in which the skeleton is substituted on the left-hand side by a cyclohexyl radical and/or the skeleton is linked on the right-hand side to a cyclohexyl radical.

Preferred compounds of the formulae IA-5 and IB-5 are:

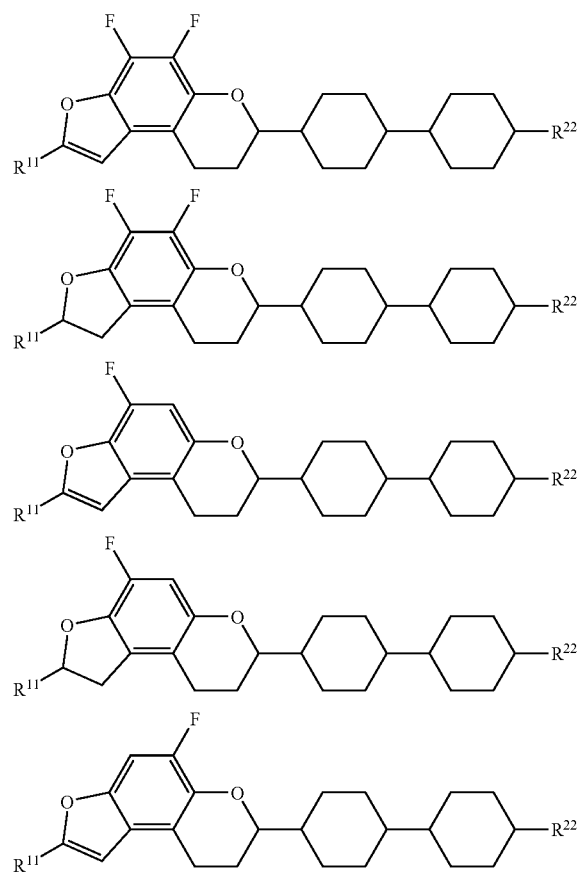

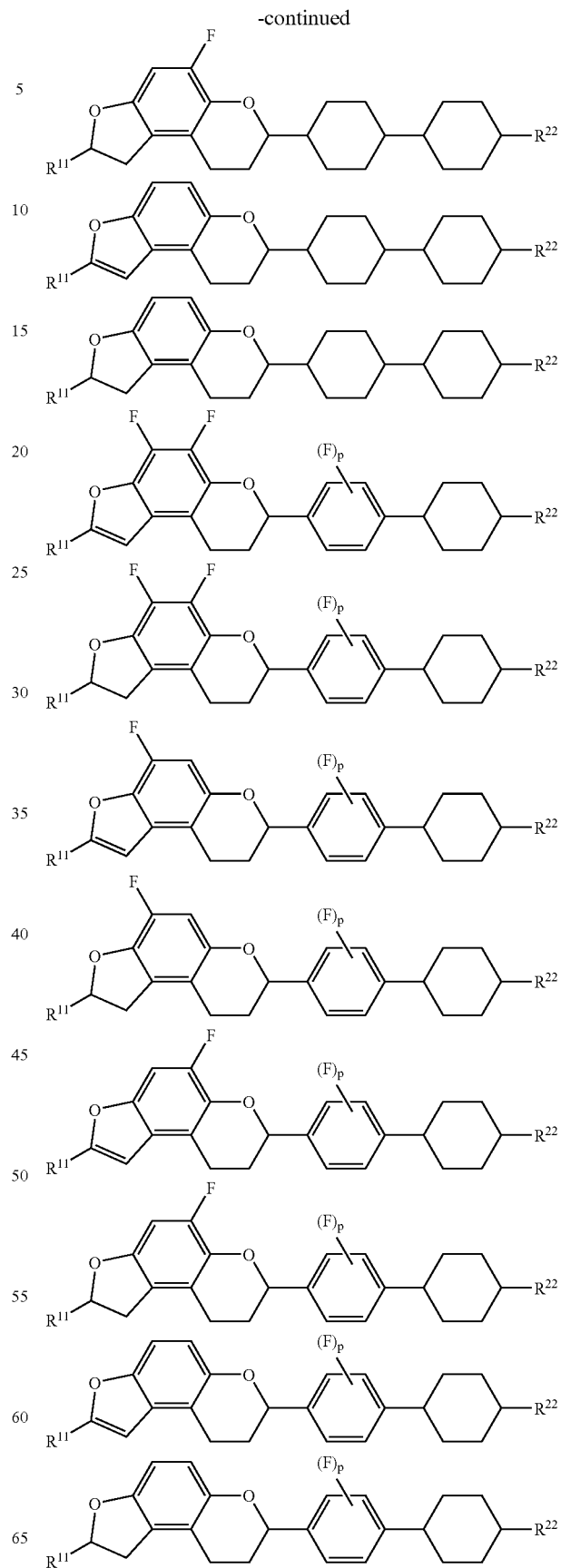

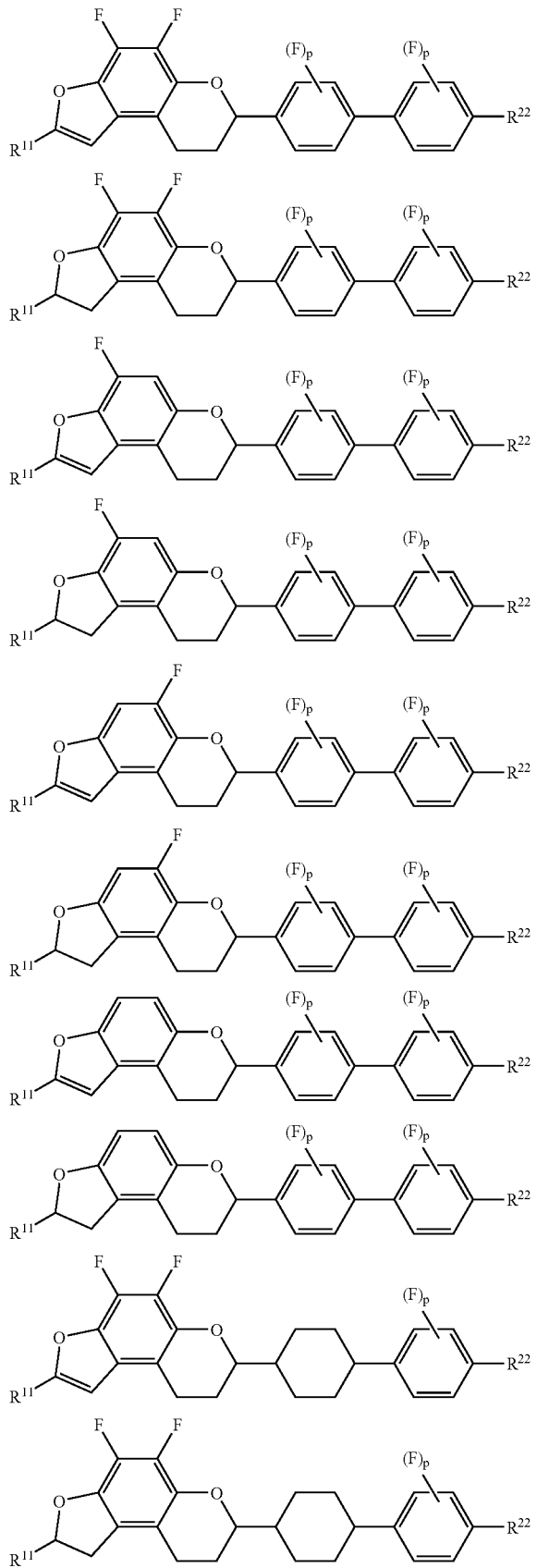
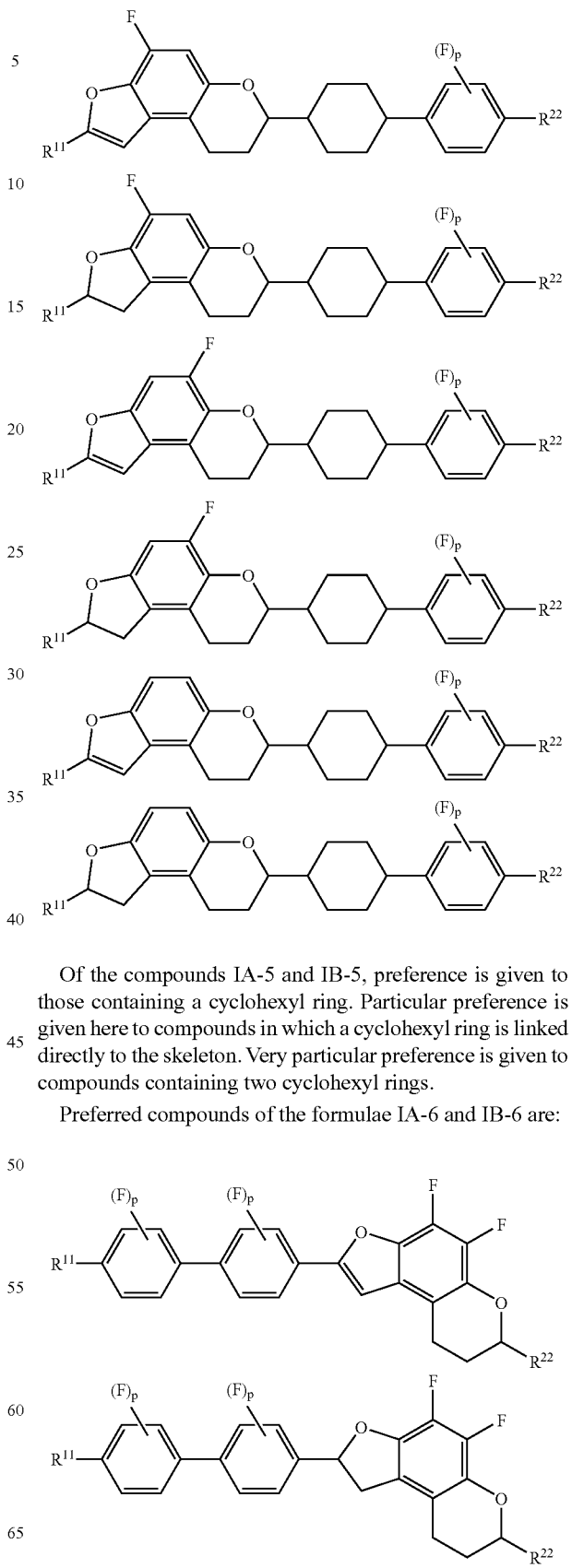
Of the compounds IA-5 and IB-5, preference is given to those containing a cyclohexyl ring. Particular preference is given here to compounds in which a cyclohexyl ring is linked directly to the skeleton. Very particular preference is given to compounds containing two cyclohexyl rings.
Preferred compounds of the formulae IA-6 and IB-6 are:

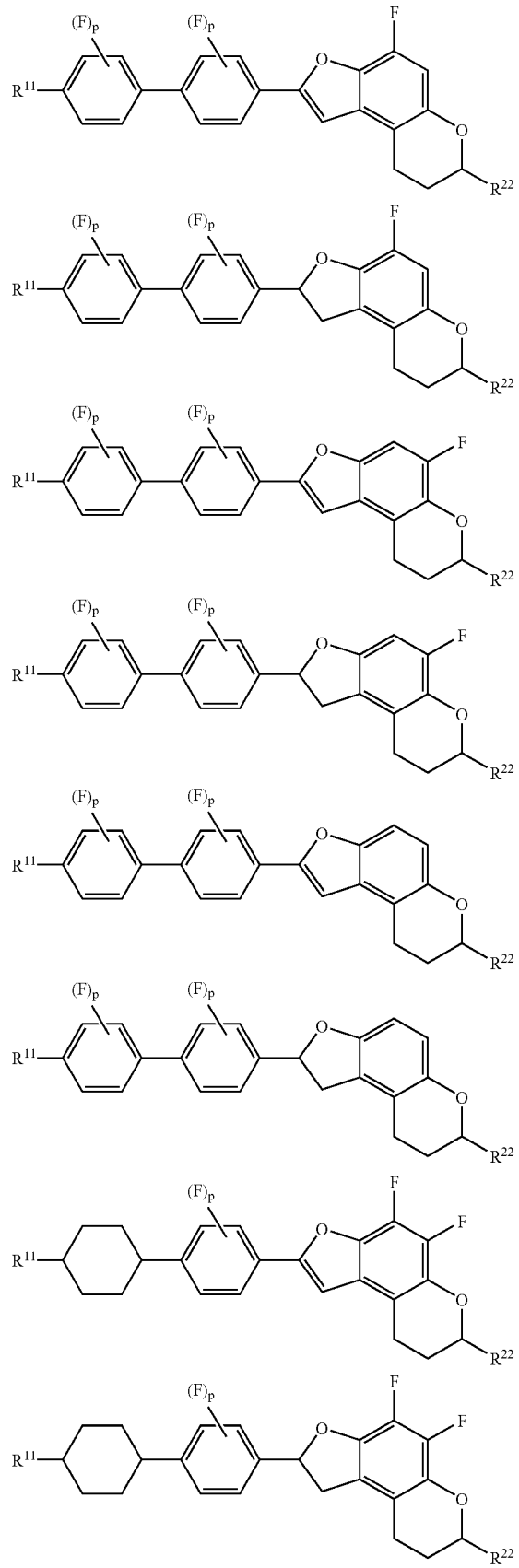
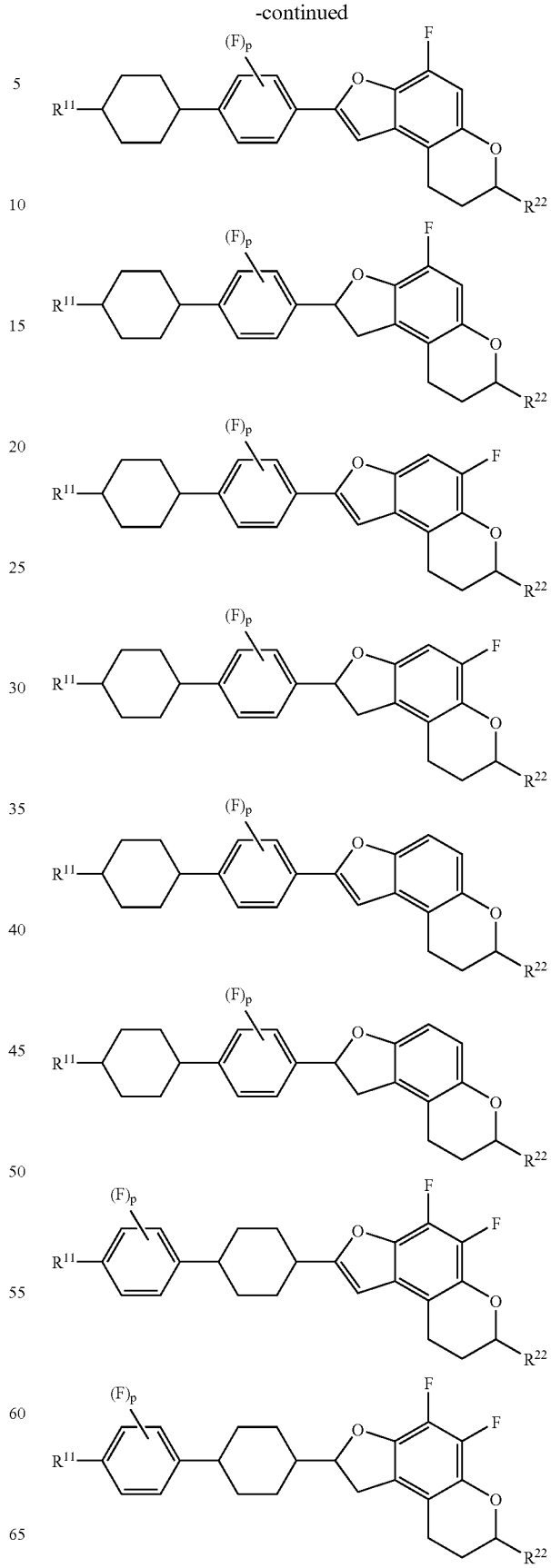

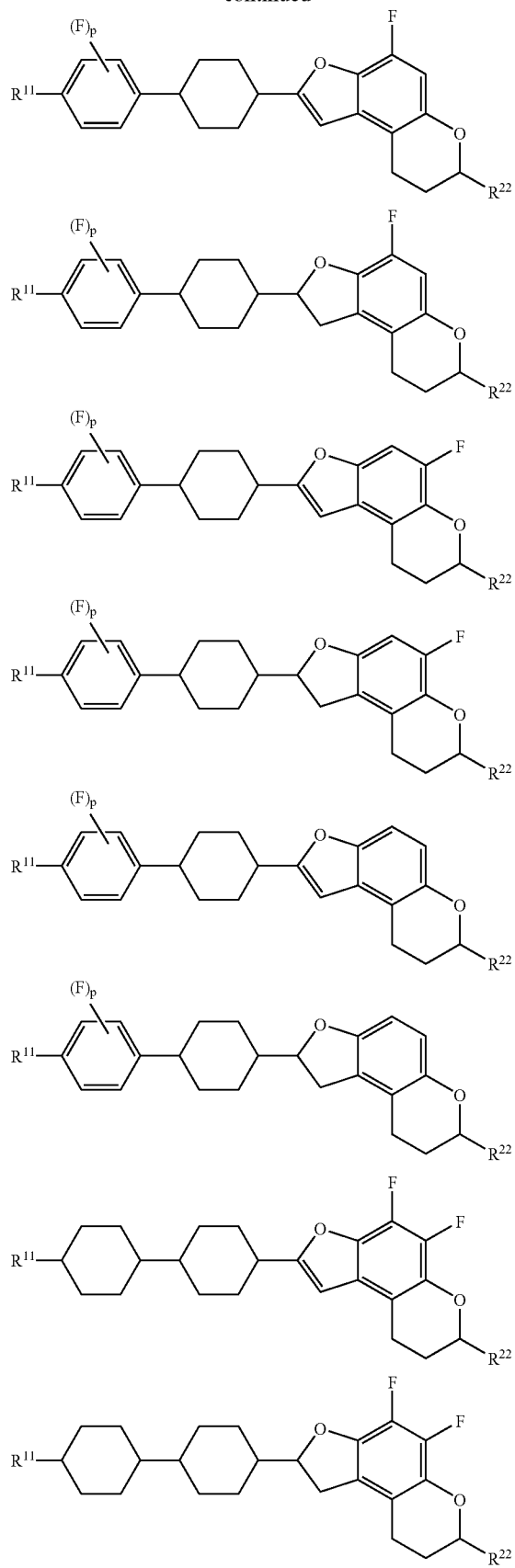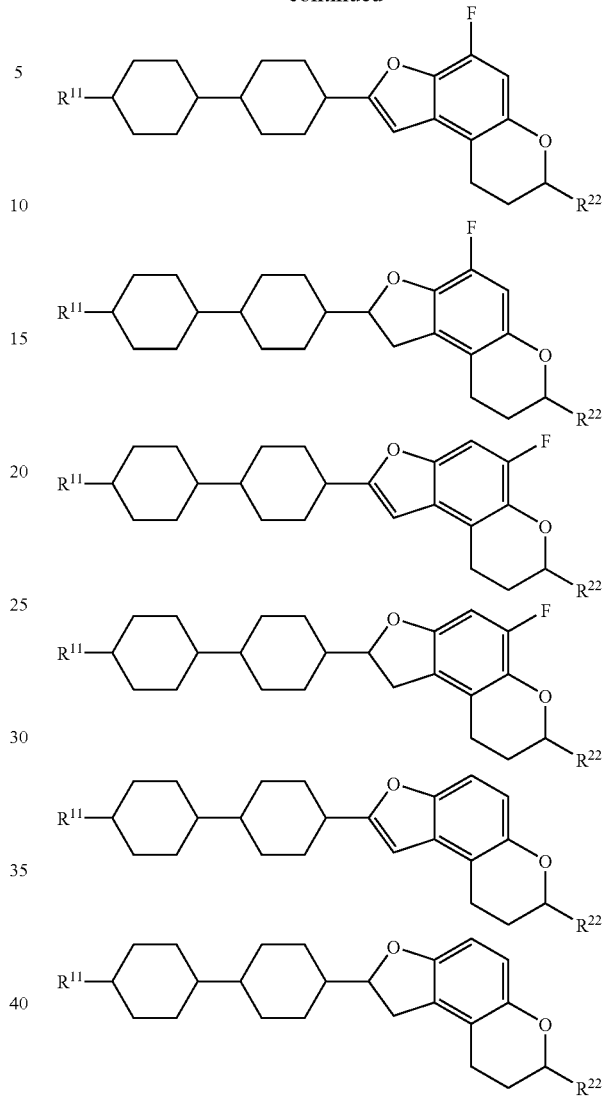

Of the compounds IA-6, preference is given to those containing an unsubstituted or substituted 14-phenylene ring. Particular preference is given here to compounds in which an unsubstituted or substituted 1,4-phenylene ring is linked directly to the skeleton.

Of the compounds IB-6, preference is given to those containing a cyclohexyl ring. Particular preference is given here to compounds in which a cyclohexyl ring is linked directly to the skeleton.

Of the compounds of the formula IA-7, preference is given to compounds of the formulae in which the skeleton is substituted on the left-hand side by an aryl radical and/or the skeleton is linked on the right-hand side to a cyclohexyl radical.

Of the compounds of the formula IB-7, preference is given to compounds of the formulae in which the skeleton is substituted on the left-hand side by a cyclohexyl radical and/or the skeleton is linked on the right-hand side to a cyclohexyl radical.

Of the compounds of the formula IA-8, preference is given to compounds of the formulae in which the skeleton is substituted on the left-hand side by an aryl radical and/or the skeleton is linked on the right-hand side to a cyclohexyl radical.

Of the compounds of the formula IB-8, preference is given to compounds of the formulae in which the skeleton is substituted on the left-hand side by a cyclohexyl radical and/or the skeleton is linked on the right-hand side to a cyclohexyl radical.

Of the compounds of the formula IA-9, preference is given to compounds of the formulae in which the skeleton is substituted on the left-hand side by an aryl radical and/or the skeleton is linked on the right-hand side to a cyclohexyl radical.

Of the compounds of the formula IB-9, preference is given to compounds of the formulae in which the skeleton is substituted on the left-hand side by a cyclohexyl radical and/or the skeleton is linked on the right-hand side to a cyclohexyl radical.

Of the compounds IA-10 and IB-10, preference is given to those containing one or more cyclohexyl rings. Particular preference is given here to compounds in which the cyclohexyl ring is linked directly to the skeleton.

Of the compounds IA-11, preference is given to those containing an unsubstituted or substituted 1,4-phenylene ring. Particular preference is given here to compounds in which the unsubstituted or substituted 1,4-phenylene ring is linked directly to the skeleton.

Of the compounds IB-11, preference is given to those containing one or more cyclohexyl rings. Particular preference is given here to compounds in which the cyclohexyl ring is linked directly to the skeleton.

Compounds of the formula I according to the invention may be chiral owing to their molecular structure and may accordingly occur in various enantiomeric forms. They can therefore be in racemic or optically active form.

The present invention also relates to liquid-crystal media which comprise one or more compound(s) of the formula I.

In a preferred embodiment, the liquid-crystal media in accordance with the present invention comprise a) one or more dielectrically negative compound(s) of the formula I

I

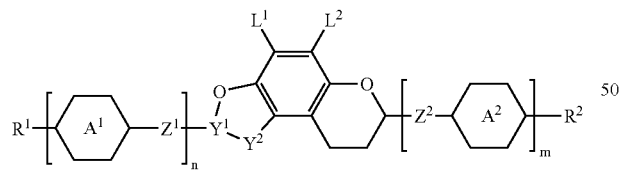

in which the parameters have the meaning given above under formula I, b) one or more dielectrically negative compound(s) of the formula II

II

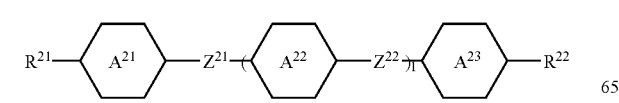

in which $R^{21}$ and $R^{22}$ each, independently of one another, have the meaning given above for $R^1$ under formula I, $Z^{21}$ and $Z^{22}$ each, independently of one another, have the meaning given above for $Z^1$ under formula I, at least one of the rings

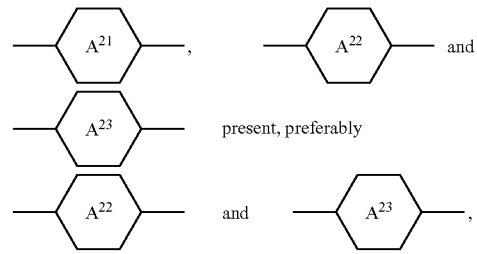

present, preferably denotes

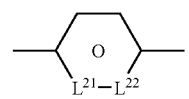

and the others, in each case independently of one another, denote

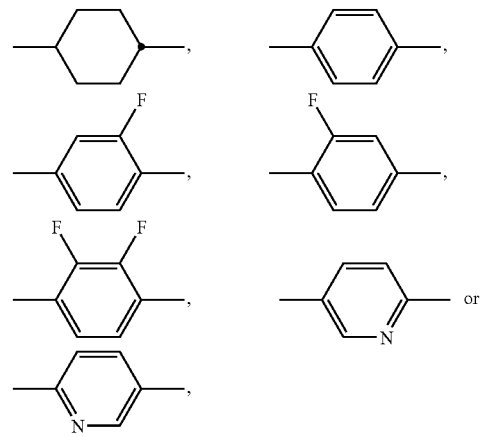

preferably

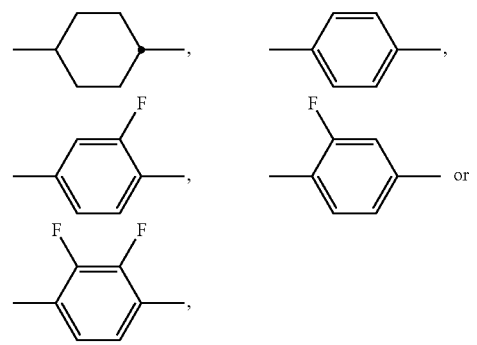

particularly preferably

denotes

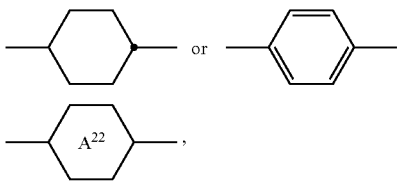

if present, denotes

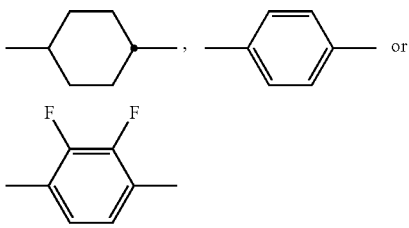

L$^{21}$ and L$^{22}$ both denote C—F or one of the two denotes N and the other denotes C—F, preferably both denote C—F, and l denotes 0, 1 or 2, preferably 0 or 1;

and optionally c) one or more dielectrically neutral compounds of the formula III

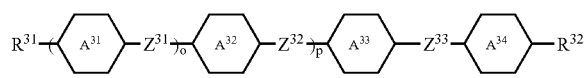 III in which

R$^{31}$ and R$^{32}$ each, independently of one another, have the meaning given above for R$^1$ under formula I, and Z$^{31}$, Z$^{32}$ and Z$^{33}$ each, independently of one another, denote —CH$_2$CH$_2$—, —CH=CH—, —COO— or a single bond,

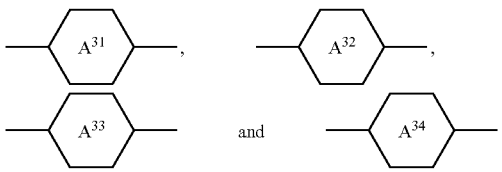

each, independently of one another, denote

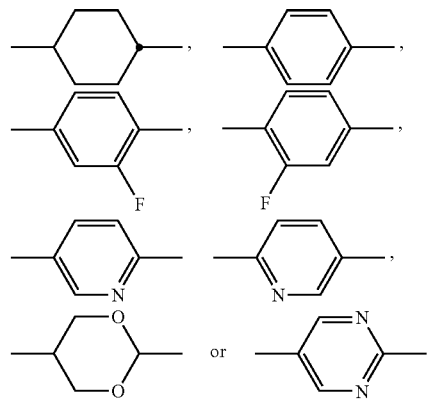

o and p, independently of one another, denote 0 or 1, but preferably

R$^{31}$ and R$^{32}$ each, independently of one another, denote alkyl or alkoxy having 1-5 C atoms or alkenyl having 2-5 C atoms,

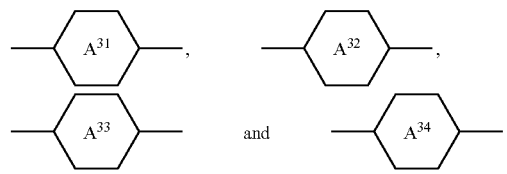

each, independently of one another, denote

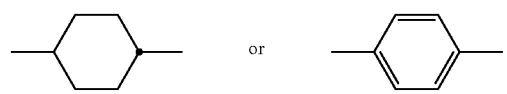

and very particularly preferably at least two of these rings denote

in which very particularly preferably two adjacent rings are linked directly, preferably

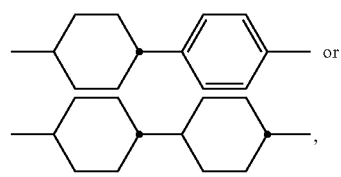

where one or more H atoms in the phenylene ring may be replaced, independently of one another, by F or CN, preferably by F, and one or two non-adjacent CH$_2$ groups of the cyclohexylene ring or one of the cyclohexylene rings may be replaced by O atoms.

The liquid-crystal media preferably comprise one or more compounds of the formula I which contain no biphenyl unit.

The liquid-crystal media particularly preferably comprise one or more compounds of the formula I in which two adjacent rings are linked directly and preferably denote

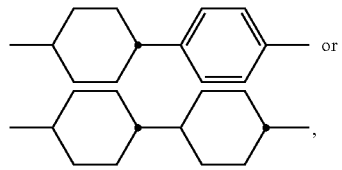 or where one or more H atoms in the phenylene ring may be replaced, independently of one another, by F or CN, preferably by F, and one or two non-adjacent $CH_2$ groups of the cyclohexylene ring or one of the cyclohexylene rings may be replaced by O atoms.

In a preferred embodiment, which may be identical with the embodiments just described, the liquid-crystal media comprise one or more compounds selected from the group of the compounds of the formula I-3.

The liquid-crystal medium preferably comprises one or more compounds selected from the group of the compounds of the formulae II-1 to II-3

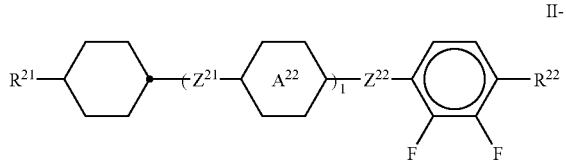

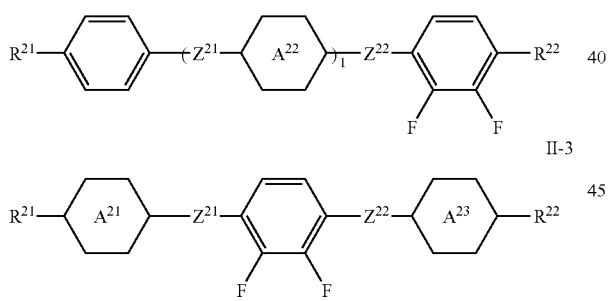

in which
$R^{21}$, $R^{22}$, $Z^{12}$, $Z^{22}$,

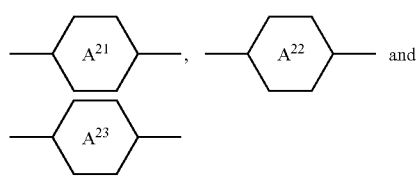

and l each have the meaning given above under formula II. Preferably, $R^{21}$ is alkyl, preferably having 1-5 C atoms, $R^{21}$ is alkyl or alkoxy, preferably each having 1 to 5 C atoms, and $Z^{22}$ and $Z^{21}$, if present, are a single bond.

The liquid-crystal medium particularly preferably comprises one or more compounds selected from the group of the compounds of the formulae III-1 to III-3:

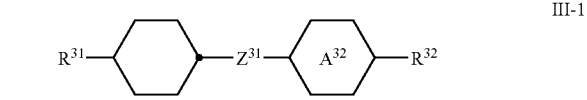

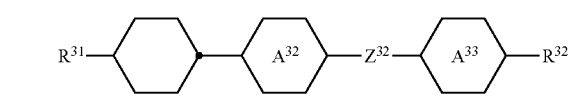

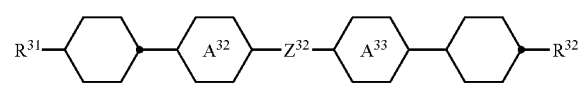

in which $R^{31}$, $R^{32}$, $Z^{31}$, $Z^{32}$,

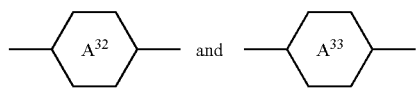

and each have the meaning indicated above under formula III.

The liquid-crystal medium especially preferably comprises one or more compounds selected from the group of the compounds of the formulae III-1a to III-1d, III-1e, III-2a to III-2g, III-3a to III-3d and III-4-a:

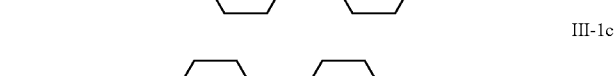

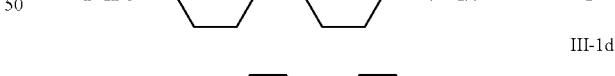

in which n and m each, independently of one another, denote 1 to 5, and o and p each, independently both thereof and of one another, denote 0 to 3,

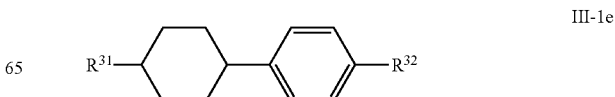

-continued

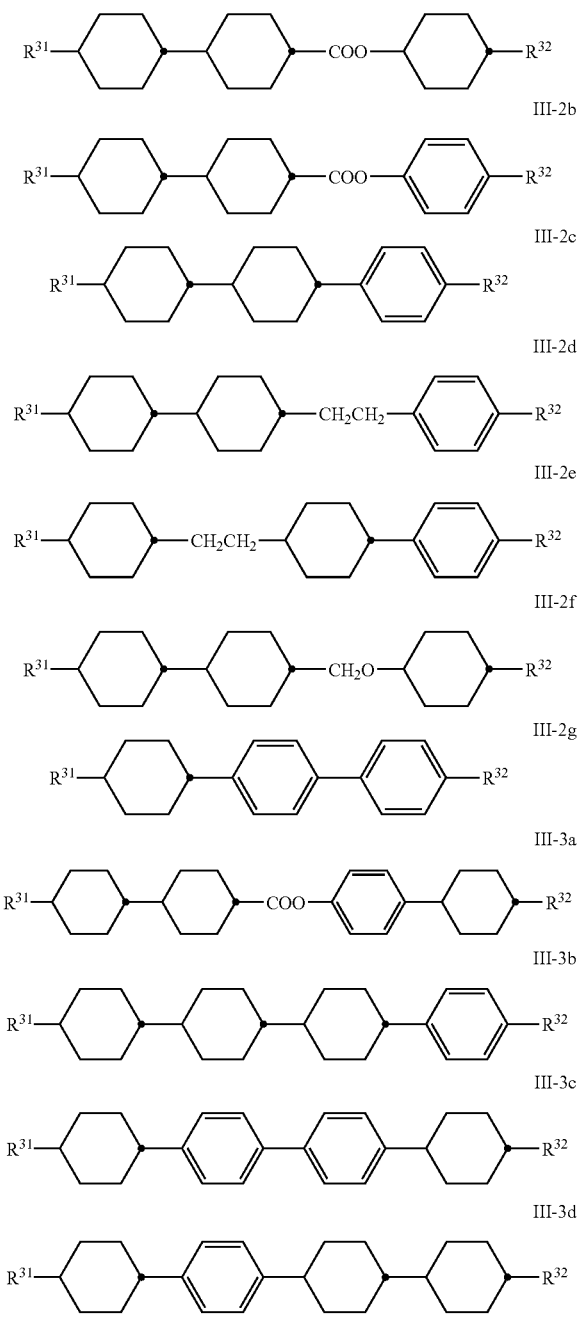

in which $R^{31}$ and $R^{33}$ each have the meaning indicated above under formula III, preferably the meaning indicated under formula III-1, and the phenyl rings, in particular in the compounds III-2g and III-3c, may optionally be fluorinated, but not so that the compounds are identical with those of the formula II and the sub-formulae thereof. Preferably, $R^{31}$ is n-alkyl having 1 to 5 C atoms, especially preferably having 1 to 3 C atoms, and $R^{32}$ is n-alkyl or n-alkoxy having 1 to 5 C atoms or alkenyl having 2 to 5 C atoms. Of these, particular preference is given to compounds of the formulae III-1a to III-1d.

Preferred fluorinated compounds of the formulae III-2g and III-3c are the compounds of the formulae III-2g' and III-3c'

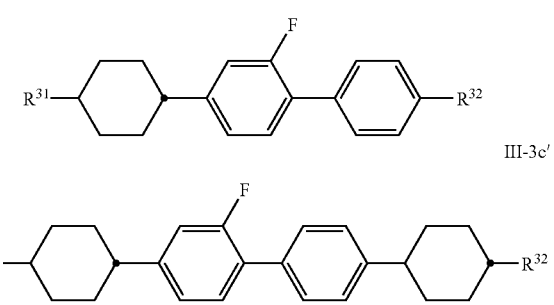

in which $R^{31}$ and $R^{33}$ each have the meaning indicated above under formula III, preferably the meaning indicated under formula III-2g or III-3c.

In the present application, the term compounds is taken to mean both one compound and a plurality of compounds, unless expressly stated otherwise.

The liquid-crystal media according to the invention preferably have nematic phases of in each case from at least −20° C. to 80° C., preferably from −30° C. to 85° C. and very particularly preferably from −40° C. to 100° C. The term "have a nematic phase" here is taken to mean firstly that no smectic phase and no crystallisation are observed at low temperatures at the corresponding temperature and secondly also that no clearing occurs on heating from the nematic phase. The investigation at low temperatures is carried out in a flow viscometer at the corresponding temperature and checked by storage in test cells having a layer thickness corresponding to the electro-optical application for at least 100 hours. At high temperatures, the clearing point is measured in capillaries by conventional methods.

Furthermore, the liquid-crystal media according to the invention are characterised by low optical anisotropy values.

The term "alkyl" preferably encompasses straight-chain and branched alkyl groups having 1 to 7 carbon atoms, in particular the straight-chain groups methyl, ethyl, propyl, butyl, pentyl, hexyl and heptyl. Groups having 2 to 5 carbon atoms are generally preferred.

The term "alkenyl" preferably encompasses straight-chain and branched alkenyl groups having 2 to 7 carbon atoms, in particular the straight-chain groups. Particularly preferred alkenyl groups are $C_2$- to $C_7$-1E-alkenyl, $C_4$- to $C_7$-3E-alkenyl, $C_5$— to $C_7$-4-alkenyl, $C_6$- to $C_{7-5}$-alkenyl and $C_{7-6}$-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluoro-butyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote 1 to 6. Preferably, n is 1 and m is 1 to 6.

Compounds containing a vinyl end group and compounds containing a methyl end group have low rotational viscosity.

In the present application, the term dielectrically positive compounds denotes compounds having a $\Delta\epsilon$ of >1.5, the term dielectrically neutral compounds denotes those in which $-1.5 \leq \Delta\epsilon \leq 1.5$, and the term dielectrically negative compounds denotes those having a $\Delta\epsilon$ of <−1.5. The dielectric anisotropy of the compounds is determined here by dissolving 10% of the compounds in a liquid-crystalline host and determining the capacitance of this mixture at 1 kHz in at least one test cell with a layer thickness of about 20 µm having a homeotropic surface alignment and at least one test cell with a layer thickness of about 20 µm having a homogeneous surface alignment. The measurement voltage is typically 0.5 V to 1.0 V, but is always less than the capacitive threshold of the respective liquid-crystal mixture.

The host mixture used for determining the applicationally relevant physical parameters is ZLI-4792 from Merck KGaA, Germany. As an exception, the determination of the dielectric anisotropy of dielectrically negative compounds is carried out using ZLI-2857, likewise from Merck KGaA, Germany. The values for the respective compound to be investigated are obtained from the change in the properties, for example the dielectric constants, of the host mixture after addition of the compound to be investigated and extrapolation to 100% of the compound employed.

The concentration employed for the compound to be investigated is 10%. If the solubility of the compound to be investigated is inadequate for this purpose, the concentration employed is, by way of exception, halved, i.e. reduced to 5%, 2.5%, etc., until the concentration is below the solubility limit.

The term threshold voltage usually relates to the optical threshold for 10% relative contrast ($V_{10}$). In relation to the liquid-crystal mixtures of negative dielectric anisotropy, however, the term threshold voltage is used in the present application for the capacitive threshold voltage ($V_0$), also known as the Freedericks threshold, unless explicitly stated otherwise.

All concentrations in this application, unless explicitly stated otherwise, are indicated in percent by weight and relate to the corresponding mixture as a whole. All physical properties are and have been determined in accordance with "Merck Liquid Crystals, Physical Properties of Liquid Crystals", status November 1997, Merck KGaA, Germany, and apply to a temperature of 20° C., unless explicitly stated otherwise. $\Delta n$ is determined at 589 nm and $\Delta\epsilon$ at 1 kHz.

In the case of the liquid-crystal media of negative dielectric anisotropy, the threshold voltage was determined as the capacitive threshold $V_0$ in cells with a liquid-crystal layer aligned homeotropically by means of lecithin.

The liquid-crystal media according to the invention may, if necessary, also comprise further additives and optionally also chiral dopants in the conventional amounts. The amount of these additives employed is in total 0% to 10%, based on the amount of the mixture as a whole, preferably 0.1% to 6%. The concentrations of the individual compounds employed are in each case preferably 0.1 to 3%. The concentration of these and similar additives is not taken into account when indicating the concentrations and the concentration ranges of the liquid-crystal compounds in the liquid-crystal media.

The compositions consist of a plurality of compounds, preferably 3 to 30, particularly preferably 6 to 20 and very particularly preferably 10 to 16 compounds, which are mixed in a conventional manner. In general, the desired amount of the components used in lesser amount is dissolved in the components making up the principal constituent, advantageously at elevated temperature. If the selected temperature is above the clearing point of the principal constituent, the completion of the dissolution process is particularly easy to observe. However, it is also possible to prepare the liquid-crystal mixtures in other conventional ways, for example using premixes or from a so-called "multibottle" system.

By means of suitable additives, the liquid-crystal phases according to the invention can be modified in such a way that they can be employed in any type of display and in particular of ECB displays and IPS displays that has been disclosed hitherto.

The examples below serve to illustrate the invention without limiting it. In the examples, the melting point T(C,N), the transition from the smectic (S) phase to the nematic (N) phase T(S,N) and the clearing point T(N,I) of a liquid-crystal substance are indicated in degrees Celsius. The various smectic phases are characterised by corresponding suffixes.

The percentages above and below are, unless explicitly stated otherwise, percent by weight, and the physical properties are the values at 20° C., unless explicitly stated otherwise.

All the temperature values indicated in this application are ° C., and all temperature differences are correspondingly differential degrees, unless explicitly stated otherwise.

In the present application and in particular in the synthesis examples and schemes, the abbreviations have the following meanings:

Bn benzyl,
cl.p. clearing point,
DEAD diethyl azodicarboxylate,
DIAD diisopropyl azodicarboxylate,
DMF dimethylformamide,
sat. saturated,
soln. solution,
MEM 2-methoxyethoxymethyl,
MOM methoxymethyl,
MTBE methyl tert-butyl ether,
Ph phenyl,
m.p. melting point,
$SiO_2$ silica gel,
TBS dimethyl-tert-butylsilyl,
THF tetrahydrofuran and
TMEDA tetramethylethylenediamine.

In the present application and in the examples below, the structures of the liquid-crystal compounds are indicated by means of acronyms, the trans-formation into chemical formulae taking place in accordance with Tables A and B below. All radicals $C_nH_{2n+1}$ and $C_mH_{2m+1}$ are straight-chain alkyl radicals having n and m C atoms respectively. The coding in Table B is self-evident. In Table A, only the acronym for the parent structure is indicated. In individual cases, the acronym for the parent structure is followed, separated by a dash, by a code for the substituents $R^1$, $R^2$, $L^1$, $L^2$ and $L^3$:

| Code for $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO•m | $OC_nH_{2n+1}$ | $C_mH_{2m+1}$ | H | H | H |
| nmFF | $C_nH_{2n+1}$ | $C_mH_{2m+1}$ | F | H | F |
| nOmFF | $C_nH_{2n+1}$ | $OC_mH_{2m+1}$ | F | H | F |
| nO•mFF | $OC_nH_{2n+1}$ | $C_mH_{2m+1}$ | F | H | F |
| nO•OmFF | $OC_nH_{2n+1}$ | $OC_mH_{2m+1}$ | F | H | F |
| n | $C_nH_{2n+1}$ | CN | H | H | H |
| nN•F | $C_nH_{2n+1}$ | CN | F | H | H |
| nN•F•F | $C_nH_{2n+1}$ | CN | F | F | H |
| nF | $C_nH_{2n+1}$ | F | H | H | H |
| nF•F | $C_nH_{2n+1}$ | F | F | H | H |
| nF•F•F | $C_nH_{2n+1}$ | F | F | F | H |
| nCl | $C_nH_{2n+1}$ | Cl | H | H | H |
| nCl•F | $C_nH_{2n+1}$ | Cl | F | H | H |
| nCl•F•F | $C_nH_{2n+1}$ | Cl | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_3$•F | $C_nH_{2n+1}$ | OCF$_3$ | F | H | H |
| nOCF$_3$•F•F | $C_nH_{2n+1}$ | OCF$_3$ | F | F | H |
| nOCF$_2$ | $C_nH_{2n+1}$ | OCHF$_2$ | H | H | H |
| nOCF$_2$•F•F | $C_nH_{2n+1}$ | OCHF$_2$ | F | F | H |
| nS | $C_nH_{2n+1}$ | NCS | H | H | H |
| rVsN | $C_rH_{2r+1}$—CH=CH—$C_sH_{2s}$— | CN | H | H | H |
| nEsN | $C_rH_{2r+1}$—O—$C_sH_{2s}$— | CN | H | H | H |
| nAm | $C_nH_{2n+1}$ | $COOC_mH_{2m+1}$ | H | H | H |
| nF•Cl | $C_nH_{2n+1}$ | F | Cl | H | H |

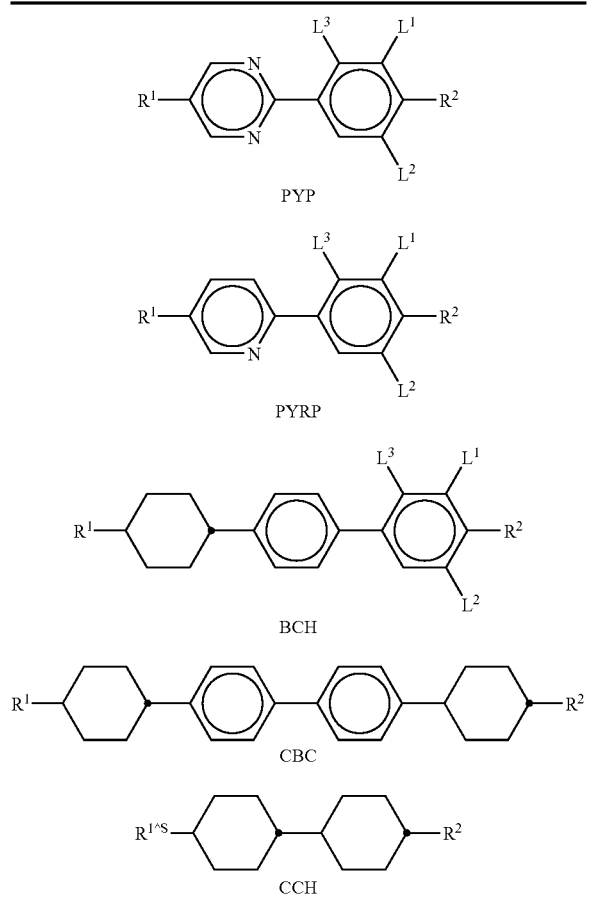

TABLE A

PYP

PYRP

BCH

CBC

CCH

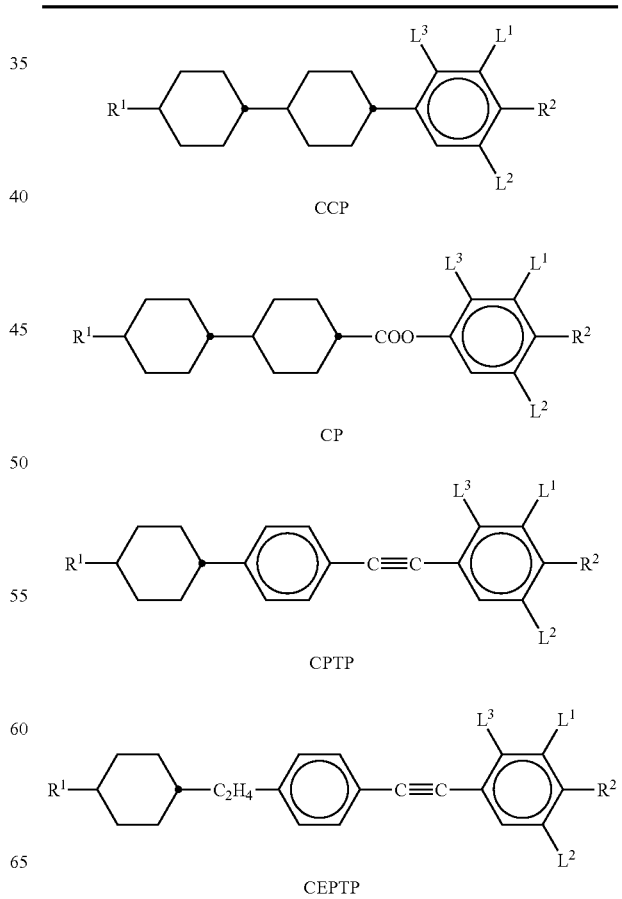

TABLE A-continued

CCP

CP

CPTP

CEPTP

TABLE A-continued
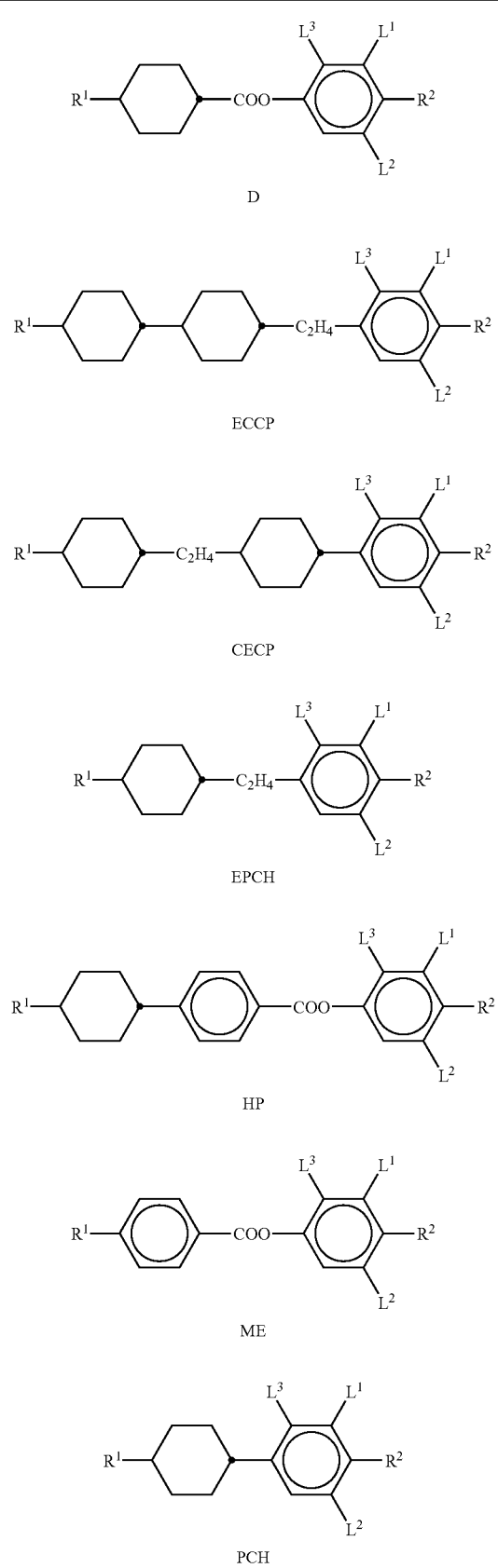
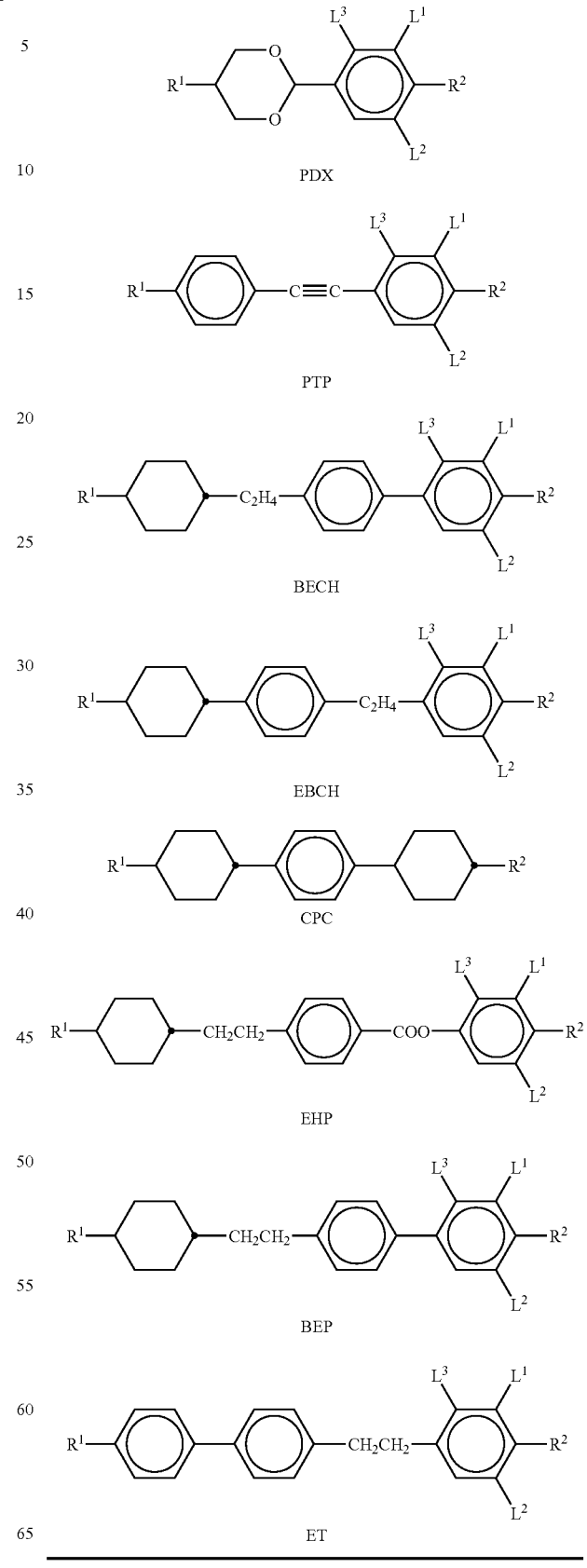

TABLE B
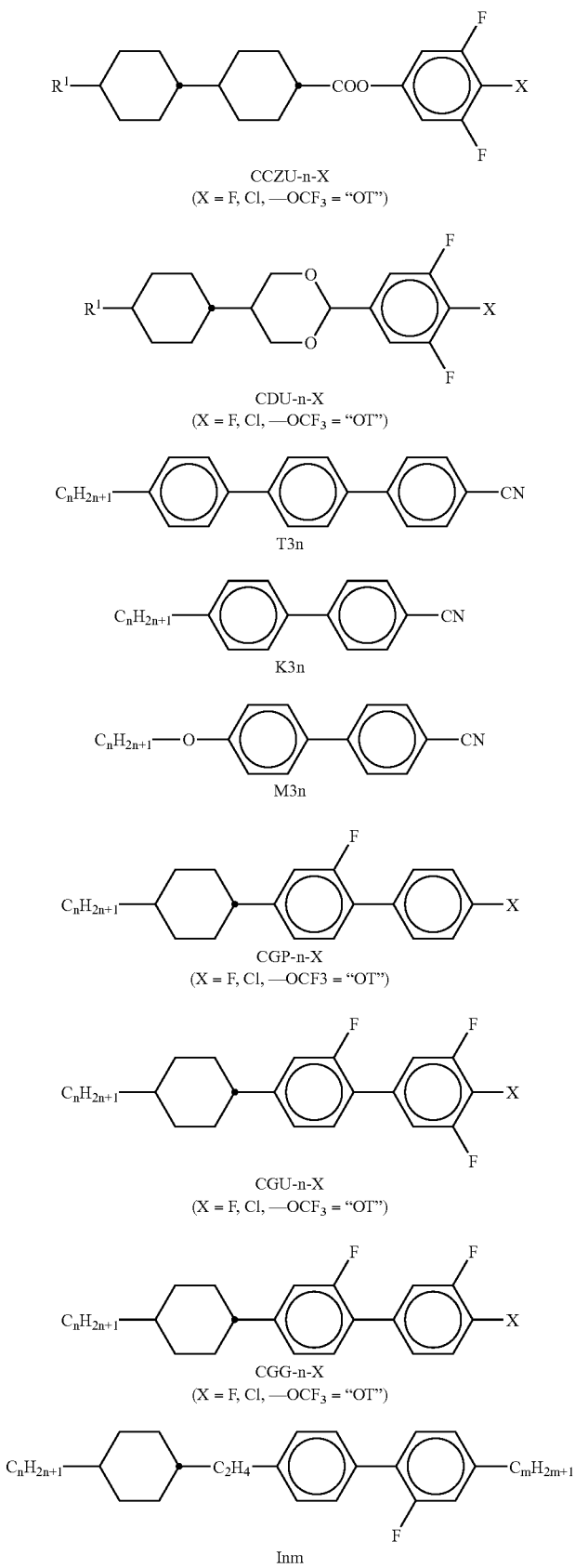

TABLE B-continued
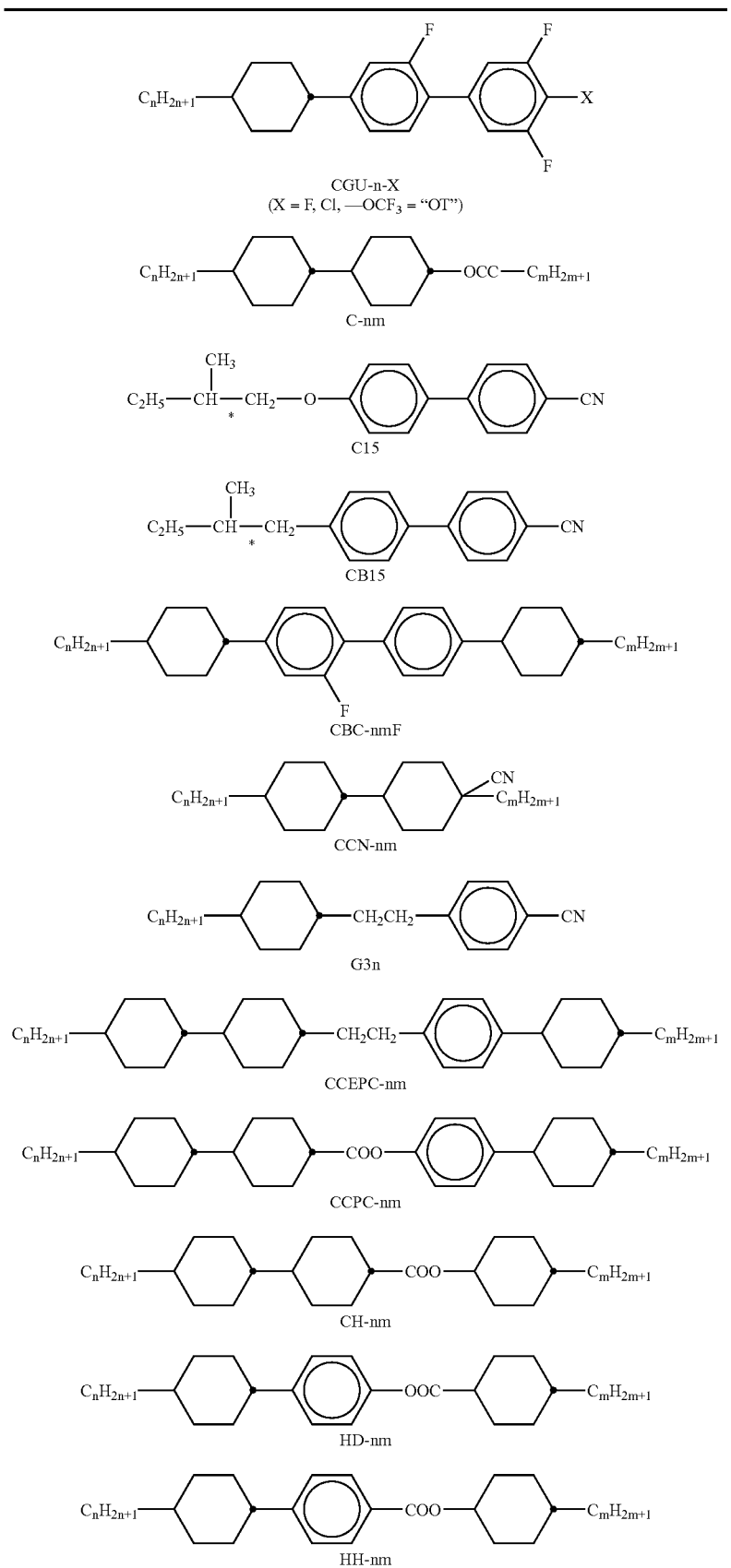

TABLE B-continued
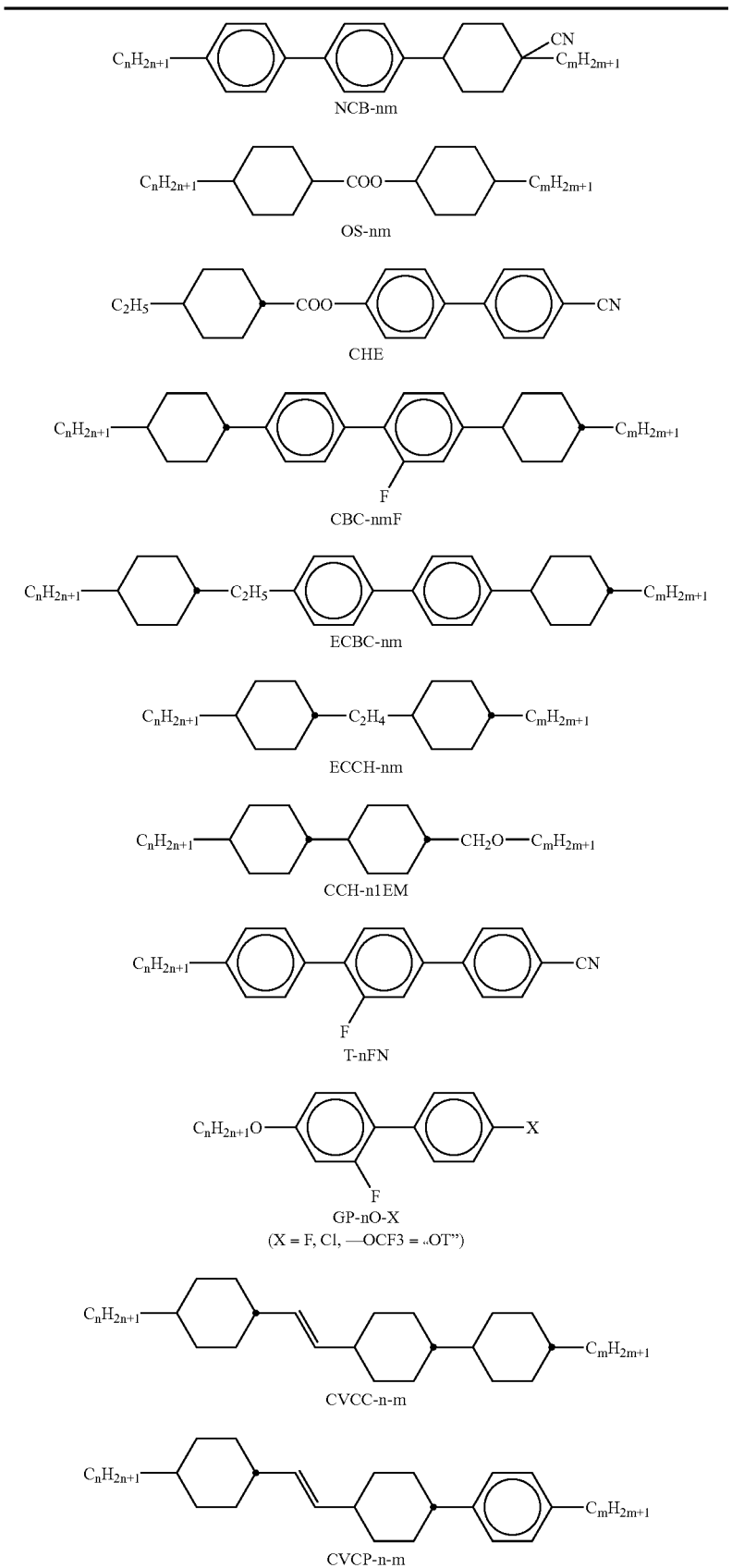

TABLE B-continued
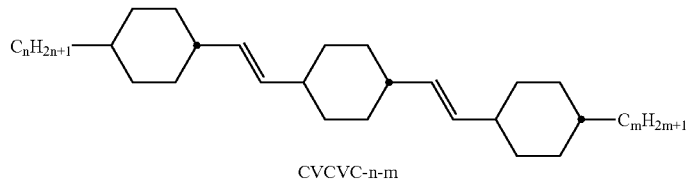
CVCVC-n-m
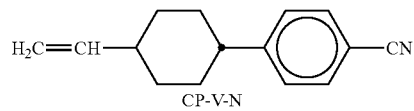
CP-V-N
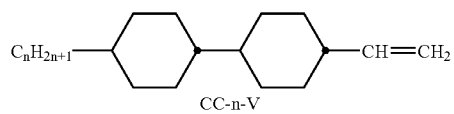
CC-n-V
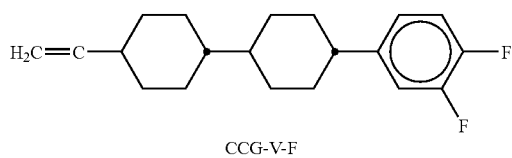
CCG-V-F
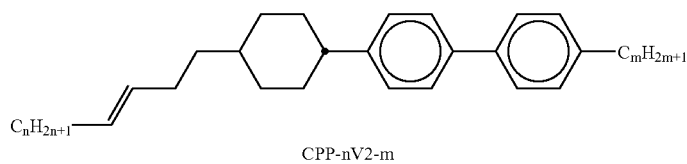
CPP-nV2-m
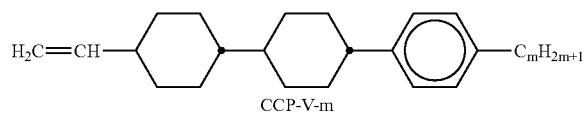
CCP-V-m
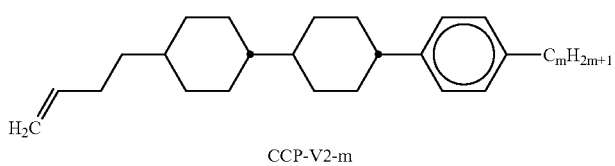
CCP-V2-m
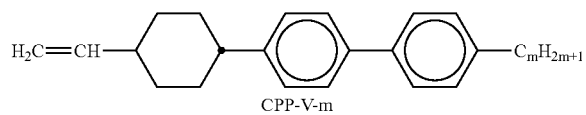
CPP-V-m
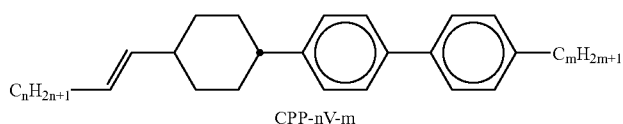
CPP-nV-m
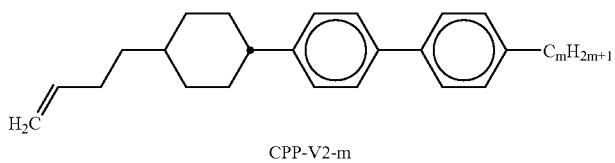
CPP-V2-m
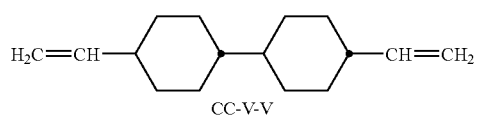
CC-V-V TABLE B-continued
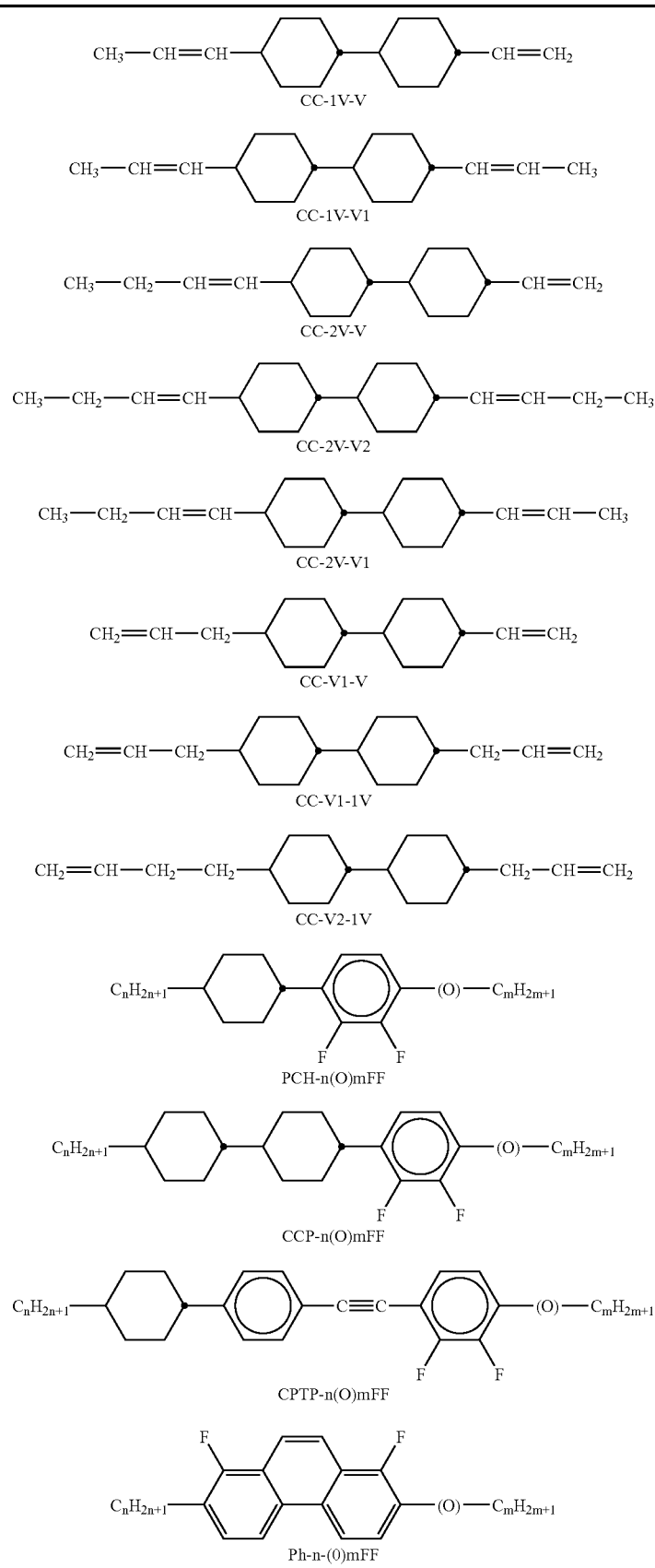

TABLE B-continued
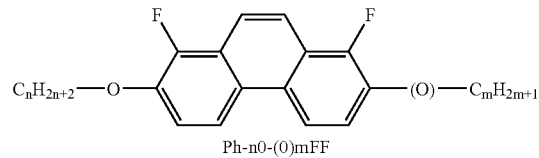
Ph-n0-(0)mFF
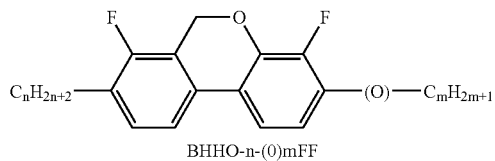
BHHO-n-(0)mFF
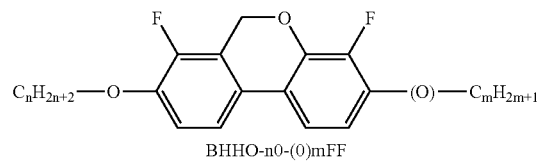
BHHO-n0-(0)mFF
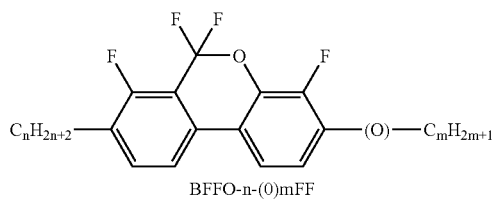
BFFO-n-(0)mFF
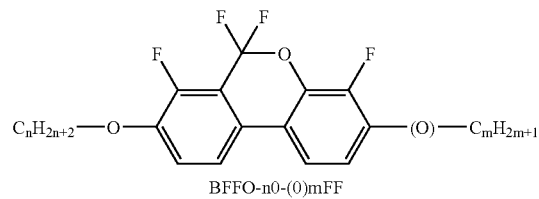
BFFO-n0-(0)mFF
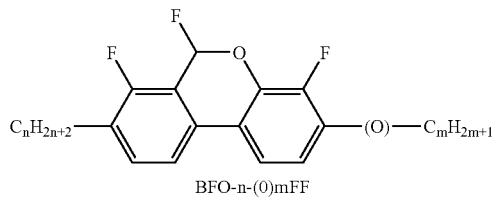
BFO-n-(0)mFF
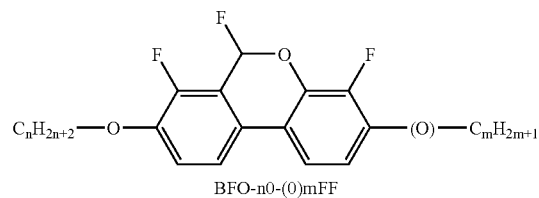
BFO-n0-(0)mFF
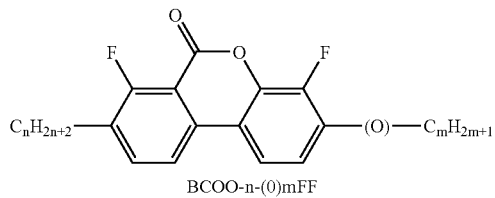
BCOO-n-(0)mFF

TABLE B-continued

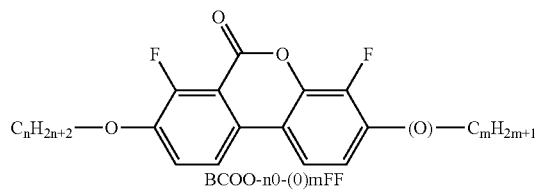

BCOO-n0-(0)mFF

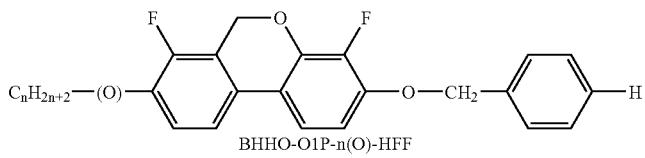

BHHO-O1P-n(O)-HFF

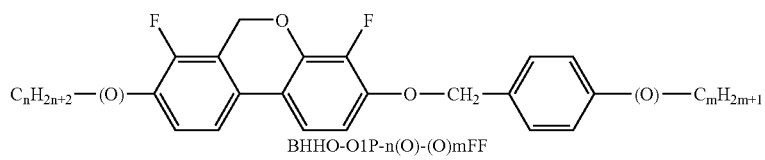

BHHO-O1P-n(O)-(O)mFF

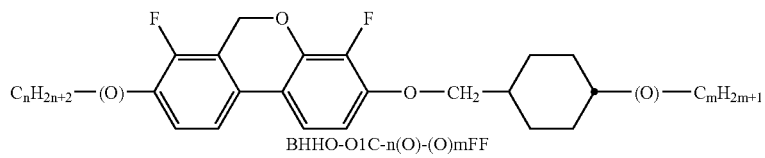

BHHO-O1C-n(O)-(O)mFF

EXAMPLES

The following examples are intended to explain the invention without limiting it. Above and below, percentage data denote percent by weight. All temperatures are indicated in degrees Celsius. Δn denotes the optical anisotropy (589 nm, 20° C.), Δ∈ the dielectric anisotropy (1 kHz, 20° C.), H.R. the voltage holding ratio (at 100° C., after 5 minutes in the oven, 1 V). $V_{10}$, $V_{50}$ and $V_{90}$ (the threshold voltage, mid-grey voltage and saturation voltage respectively) and $V_0$ (the capacitive threshold voltage) were each determined at 20° C.

Example 1

4,5-Difluoro-2-(4-propylcyclohexyl)-8,9-dihydro-7H-furo[3,2-f]-chromene

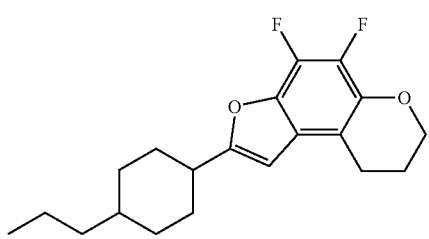

1.1. Preparation of 1,2-difluoro-3-prop-2-ynyloxybenzene

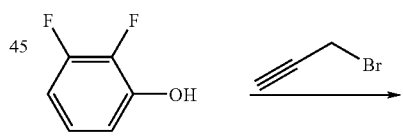

115.0 g (0.88 mol) of 2,3-difluorophenol are refluxed for 3 h together with 118.2 ml (17.7 mol) of propargyl bromide (80% soln. in toluene) and 146.6 g (138.2 mol) of potassium carbonate in 1.6 l of ethyl methyl ketone. The batch is filtered, and the filter residue is washed with MTBE. The filtrate is concentrated to dryness, and the residue is purified by column chromatography ($SiO_2$, n-heptane:MTBE=3:1).

1.2. Preparation of 7,8-difluoro-2H-chromene

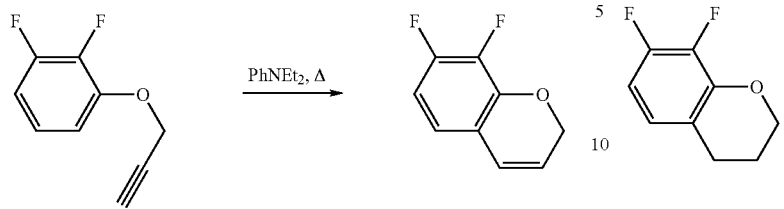

73.0 g (0.43 mol) of 1,2-difluoro-3-prop-2-ynyloxybenzene are heated at 200° C. for 3 h in an autoclave together with 126.0 g (2.17 mol) of potassium fluoride in 650 ml of N,N-diethylaniline. Water is added to the batch, which is then acidified using 25% HCl. The solution is extracted with MTBE, and the combined organic phases are washed with sat. sodium chloride soln. The solution is dried using sodium sulfate and concentrated to dryness. The residue is purified by column chromatography (SiO$_2$, n-heptane:MTBE=10:1). The reaction does not proceed to completion, giving a mixture of 7,8-difluoro-2H-chromene and the starting material 1,2-difluoro-3-prop-2-ynyloxybenzene.

1.3. Preparation of 7,8-difluorochroman

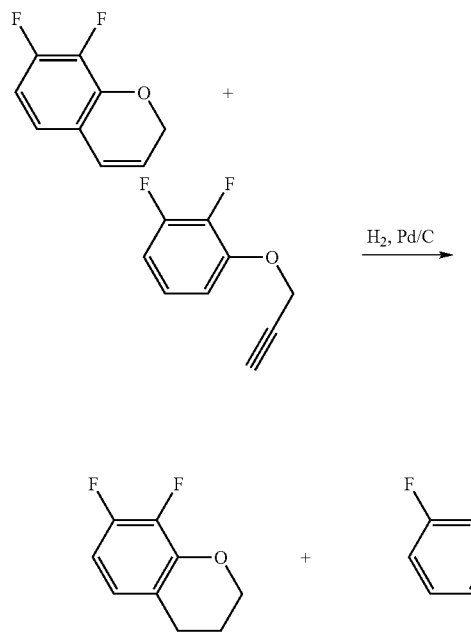

A mixture of 7,8-difluoro-2H-chromene and 1,2-difluoro-3-prop-2-ynyloxybenzene (43.2 g) is hydrogenated at 20° C. for 1 h in 430 ml of THF in the presence of Pd/C (5% Pd). The batch is concentrated to dryness, and the crude product is purified by column chromatography (SiO$_2$, n-pentane:1-chlorobutane=4:1), giving pure 7,8-difluorochroman as a slightly yellowish liquid.

1.4. Preparation of 7,8-difluorochroman-6-ol

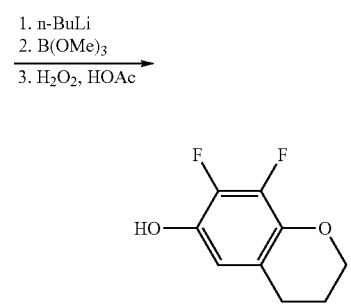

81.2 ml (0.13 mol) of n-BuLi (15% soln. in hexane) are added at −70° C. to a soln. of 20.0 g (0.12 mol) of 7,8-difluorochroman in 400 ml of THF. After 3 h at this temperature, 14.4 ml (0.13 mol) of trimethyl borate are added dropwise, and the batch is warmed to room temperature. 30 ml of dilute acetic acid (about 30%) are added, and 30 ml of aq. hydrogen peroxide soln. (35%) are carefully added to the batch. When the addition is complete, the mixture is stirred at 20° C. for 17 h. Water is added, and the batch is acidified using HCl. The solution is extracted a number of times with MTBE, and the combined organic phases are washed successively with water, sat. sodium chloride soln. and ammonium iron(II) sulfate soln. The solution is dried using sodium sulfate and concentrated to dryness. The crude product is purified by column chromatography (SiO$_2$, n-heptane:MTBE=2:1).

1.5. Preparation of 7,8-difluoro-6-methoxymethoxychroman

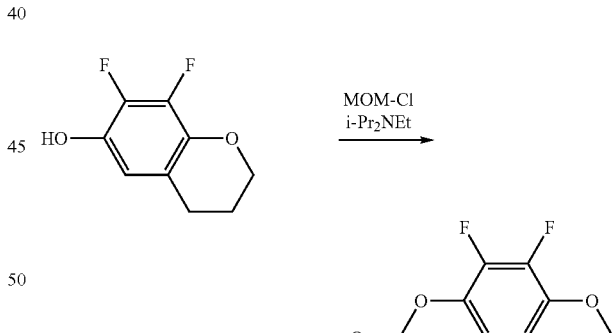

15.0 g (80.6 mmol) of 7,8-difluorochroman-6-ol are dissolved in 135 ml of dichloromethane, and 16.5 ml (94.2 mmol) of N-ethyldiisopropylamine are added with ice-cooling. After 5 min, 7.34 ml (97.0 mmol) of chloromethyl methyl ether are metered in the temperature range from 15 to 30° C. After 18 h at 20° C., 50 ml of triethylamine are added, and the batch is stirred again for 18 h. Water is added to the reaction mixture, and the organic phase is separated off. The aqueous phase is extracted with dichloromethane, and the combined organic phases are washed successively with water and sat. sodium chloride soln. The solution is dried using sodium sulfate and concentrated to dryness. The crude product is purified by column chromatography (SiO$_2$, n-heptane:MTBE=2:1), giving 7,8-difluoro-6-methoxymethoxychroman as a yellowish solid.

1.6. Preparation of 7,8-difluoro-5-iodo-6-methoxymethoxychroman

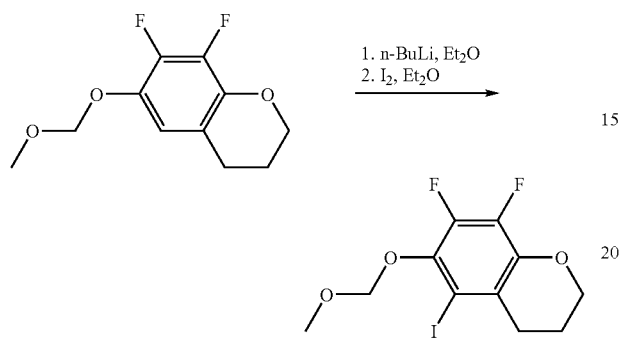

16.6 g (72.1 mmol) of 7,8-difluoro-6-methoxymethoxychroman are initially introduced in 350 ml of THF, and 54.3 ml (86.5 mmol) of n-BuLi (15% soln. in hexane) are added dropwise at −78° C. When the addition is complete, the mixture is stirred at this temperature for 30 min and subsequently at 20° C. for 1 h. The solution is re-cooled to −78° C., and a solution of 22.0 g (86.5 mol) of iodine in 100 ml of THF is added dropwise. The reaction mixture is stirred at room temperature for 1.5 h and subsequently diluted with MTBE. The solution is washed with water and sat. sodium chloride soln. and dried using sodium sulfate. The crude product remaining after removal of the solvents is purified by column chromatography (SiO$_2$, n-heptane:MTBE=2:1), giving 7,8-difluoro-5-iodo-6-methoxymethoxychroman as a brownish oil.

1.7. Preparation of 7,8-difluoro-5-iodochroman-6-ol

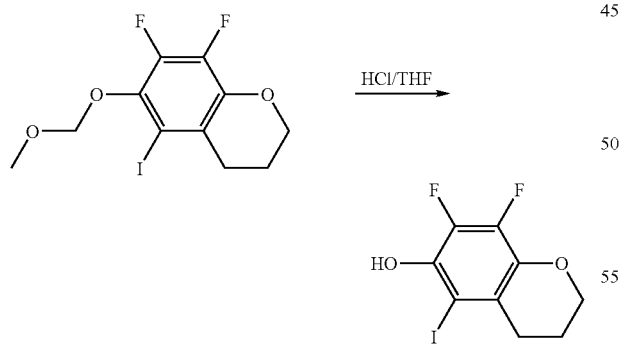

10.4 ml of conc. HCl are added to a solution of 20.2 g (56.7 mmol) of 7,8-difluoro-5-iodo-6-methoxymethoxychroman in 100 ml of THF, and the mixture is stirred at 20° C. for 18 h. The batch is diluted with MTBE, and the solution is washed with water. The aqueous phase is extracted with MTBE, and the combined organic phases are washed with water and sat. sodium chloride soln. The solution is dried using sodium sulfate and concentrated to dryness. The crude product is purified by column chromatography (SiO$_2$, n-heptane:MTBE=1:1), giving 7,8-difluoro-5-iodochroman-6-ol as a pale-brown solid.

1.8. Preparation of 7,8-difluoro-5-(4-propylcyclohexylethynyl)chroman-6-ol

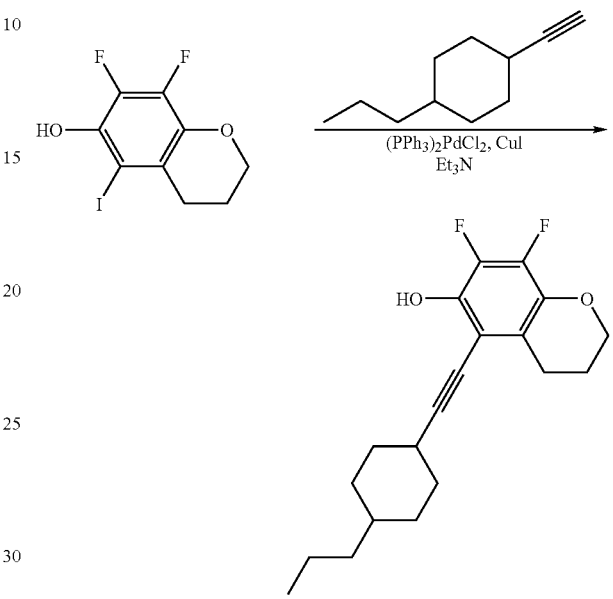

7.0 g (22.4 mmol) of 7,8-difluoro-5-chroman-6-ol are stirred at 50° C. for 18 h together with 5.06 g (33.5 mmol) of 1-ethynyl-4-propylcyclohexane in the presence of 472 mg (0.67 mmol) of bis(triphenylphosphine)palladium(II) chloride and 128 mg (0.67 mmol) of copper(I) iodide in 90 ml of triethylamine. After cooling, the batch is added to ice/water and acidified using hydrochloric acid. The mixture is extracted a number of times with MTBE, and the combined extracts are washed with water and sat. sodium chloride soln. The solution is dried using sodium sulfate and concentrated to dryness. The residue is purified by column chromatography (SiO$_2$, 1-chlorobutane). The oil obtained is used directly for the following reaction.

1.9. Preparation of 4,5-difluoro-2-(4-propylcyclohexyl)-8,9-dihydro-7H-furo-[3,2-f]chromene

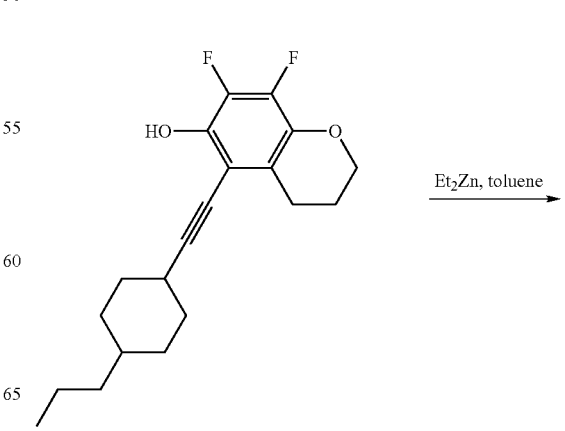

-continued

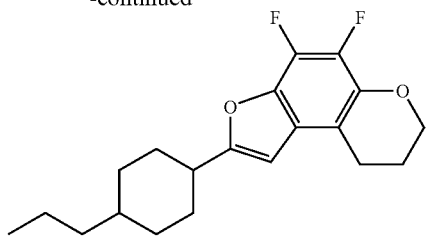

5.80 g (17.3 mmol) of 7,8-difluoro-5-(4-propylcyclohexylethynyl)chroman-6-ol are initially introduced together with 0.26 ml (1.73 mmol) of TMEDA, and 9.6 ml (9.6 mmol) of diethylzinc (1 M soln. in heptane) are added to the mixture at 3° C. When the evolution of gas has subsided, 25 ml of toluene are added, and the batch is refluxed for 40 h. The solution is added to sat. ammonium chloride soln., and the mixture is extracted with toluene. The combined organic phases are washed with water and sat. sodium chloride soln. and dried using sodium sulfate. The solution is concentrated to dryness, and the residue is purified by column chromatography (SiO$_2$, 1-chlorobutane:pentane=2:1). Further purification is carried out by repeated recrystallisation from ethanol at reduced temperature, giving 4,5-difluoro-2-(4-propylcyclohexyl)-8,9-dihydro-7H-furo[3,2-f]chromene as a colourless solid having a melting point of 89° C. (Δ∈=−5.0).

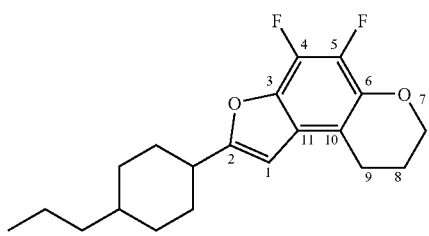

$^1$H-NMR (300 MHz, CHCl$_3$): δ=6.23 (dd, 1H, J=3.0 Hz, J=1.0 Hz, 1-H), 4.27-4.24 (m, 2H, 7-H), 2.81 (td, 2H, J=7.8 Hz, J=1.5 Hz, 9-H), 2.67 (tm, 1H, J=12.0 Hz, H$_{aliph.}$), 2.18-2.04 (m, 4H, H$_{aliph.}$), 1.87 (dm, 2H, J=12.0 Hz, H$_{aliph.}$), 1.54-1.43 (m, 2H, H$_{aliph.}$), 1.39-1.27 (m, 3H, H$_{aliph.}$), 1.26-1.27 (m, 2H, H$_{aliph.}$), 1.11-0.97 (m, 2H, H$_{aliph.}$), 0.90 (t, 3H, J=7.1 Hz, CH$_2$CH$_2$CH$_3$).

$^{19}$F-NMR (282 MHz, CHCl$_3$): δ=−162.7 (dm, 1F, J=19.5 Hz), −166.5 (d, 1F, J=19.5 Hz).

MS (EI): m/e (%)=334 (100, M$^+$), 249 (48).

Example 2

4,5-Difluoro-2-(4-propylcyclohexyl)-1,7,8,9-tetrahydro-2H-furo-[3,2-f]chromene 2.1. Preparation of 4,5-difluoro-2-(4-propylcyclohexyl)-1,7,8,9-tetrahydro-2H-furo[3,2-f]chromene

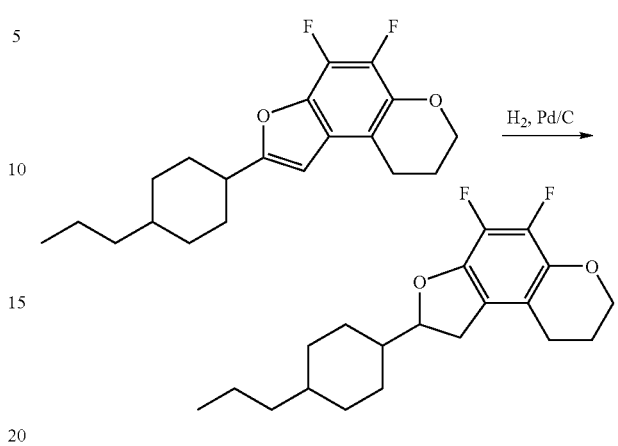

1.00 g (2.99 mmol) of 4,5-difluoro-2-(4-propylcyclohexyl)-8,9-dihydro-7H-furo[3,2-f]chromene is hydrogenated for 15 h at room temperature and atmospheric pressure in THF using elemental hydrogen in the presence of Pd/C (5% Pd). The reaction soln. is concentrated to dryness, and the residue is purified by column chromatography (SiO$_2$, 1-chlorobutane pentane=2:1). Further purification is carried out by recrystallisation from ethanol, giving 4,5-difluoro-2-(4-propylcyclohexyl)-1,7,8,9-tetrahydro-2H-furo[3,2-f]chromene as a colourless solid having an m.p. of 96° C. (Δ∈=−7.0).

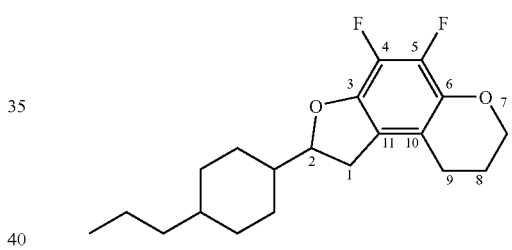

$^1$H-NMR (300 MHz, CHCl$_3$): δ=4.61-4.53 (m, 1H, 2-H), 4.19-4.16 (m, 2H, 7-H), 3.04-2.96 (m, 1H, 1-H), 2.84-2.75 (m, 1H, 1-H), 2.60-2.54 (m, 2H, 9-H), 2.05-1.97 (m, 3H, H$_{aliph.}$), 1.81 (dm, 2H, J=13.2 Hz, H$_{aliph.}$), 1.75-1.66 (m, 2H, H$_{aliph.}$), 1.64-1.56 (m, 1H, H$_{aliph.}$), 1.38-1.24 (m, 2H, H$_{aliph.}$), 1.22-1.01 (m, 4H, H$_{aliph.}$), 0.98-0.82 (m, 5H, H$_{aliph.}$).

$^{19}$F-NMR (282 MHz, CHCl$_3$): δ=−162.1 (d, 1F, J=19.5 Hz), −163.1 (d, 1F, J=19.5 Hz).

MS (EI): m/e (%)=336 (82, M$^+$), 199 (100).

Example 3

4,5-Difluoro-7-pentyl-2-(4-propylcyclohexyl)-8,9-dihydro-7H-furo[3,2-f]chromene

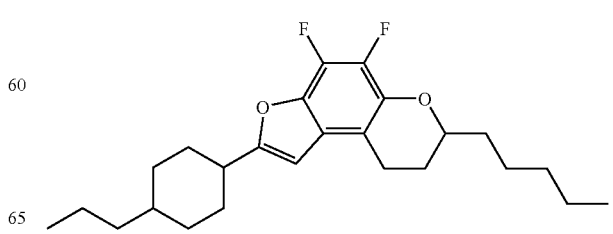

3.1. Preparation of 1-(1-ethynylhexyloxy)-2,3-difluorobenzene

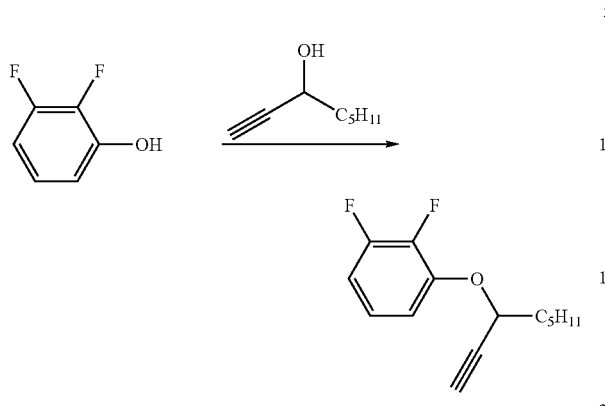

42.4 g (0.33 mol) of 2,3-difluorophenol are initially introduced in 1.2 l of THF together with 50.0 ml (0.34 mol) of 1-octyn-3-ol and 94.1 g (0.36 mol) of triphenylphosphine, and a solution of 76.1 ml (0.39 mol) of DIAD in 100 ml of THF is added dropwise. After 19 h at 20° C., the mixture is diluted with MTBE, and the batch is washed with water. The aqueous phase is extracted with MTBE, and the combined organic phases are washed with sat. sodium chloride soln. The solution is dried using sodium sulfate and concentrated to dryness. The residue is purified by column chromatography (SiO$_2$, 1-chlorobutane), giving 1-(1-ethynylhexyloxy)-2,3-difluorobenzene as a colourless oil.

3.2. Preparation of 7,8-difluoro-2-pentyl-2H-chromene

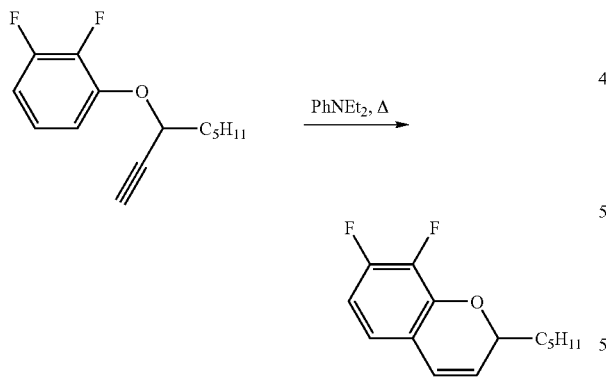

62.0 g (0.26 mol) of 1-(1-ethynylhexyloxy)-2,3-difluorobenzene are heated at 195° C. for 2 h in 390 ml of N,N-diethylaniline. The batch is diluted with MTBE and washed a number of times with 1 N HCl. The organic phase is dried using sodium sulfate and concentrated to dryness. The residue is purified by column chromatography (SiO$_2$, n-pentane:1-chlorobutane=5:1), giving 7,8-difluoro-2-pentyl-2H-chromene as a brown oil.

3.3. Preparation of 7,8-difluoro-2-pentylchroman

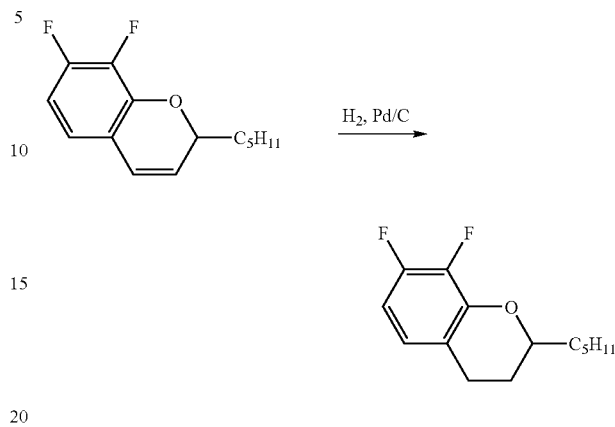

51.0 g (0.21 mol) of 7,8-difluoro-2-pentyl-2H-chromene are hydrogenated for 1 h at room temperature in 510 ml of toluene in the presence of Pd/C (5% Pd). The batch is concentrated to dryness. The crude product (yellowish liquid) can be used directly for the next step.

3.4. Preparation of 7,8-difluoro-2-pentylchroman-6-ol

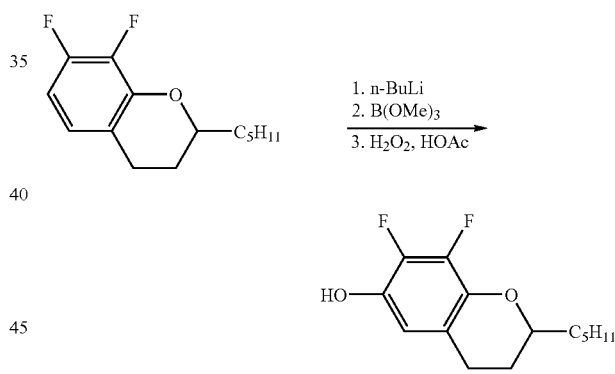

52.4 g (about 0.22 mol) of crude 7,8-difluoro-2-pentylchroman are initially introduced in 400 ml of THF, and 150.7 ml (0.24 mol) of n-BuLi (15% soln. in hexane) are added at −70° C. After 3 h at this temperature, 26.8 ml (0.24 mol) of trimethyl borate are added dropwise, and the batch is warmed to room temperature. 55 ml of dilute acetic acid (about 30%) are added, and 57 ml of hydrogen peroxide soln. (35%) are carefully added to the batch. When the addition is complete, the mixture is stirred for 17 h at room temperature. Water is added, and the batch is acidified using HCl. The solution is extracted a number of times with MTBE, and the combined organic phases are washed successively with water, sat. sodium chloride soln. and ammonium iron(II) sulfate soln. The solution is dried using sodium sulfate and concentrated to dryness. The crude product is purified by column chromatography (SiO$_2$, n-heptane:MTBE=2:1).

3.5. Preparation of 7,8-difluoro-6-methoxymethoxy-2-pentylchroman

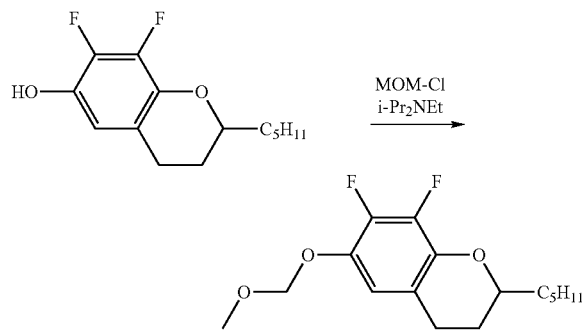

16.9 g (65.9 mmol) of 7,8-difluoro-2-pentylchroman-6-ol are dissolved in 110 ml of dichloromethane, and 13.5 ml (77.1 mmol) of N-ethyldiisopropylamine are added with ice-cooling. After 5 min, 6.0 ml (79.0 mmol) of chloromethyl methyl ether are metered in the temperature range from 15 to 30° C. After 16 h at room temperature, 50 ml of triethylamine are added, and the batch is stirred again for 24 h. Water is added to the reaction mixture, and the organic phase is separated off. The aqueous phase is extracted with dichloromethane, and the combined organic phases are washed successively with water and sat. sodium chloride soln. The solution is dried using sodium sulfate and concentrated to dryness. The crude product is purified by column chromatography (SiO$_2$, 1-chlorobutane), giving 7,8-difluoro-6-methoxymethoxy-2-pentylchroman as a yellowish oil.

3.6. Preparation of 7,8-difluoro-5-iodo-6-methoxymethoxy-2-pentylchroman

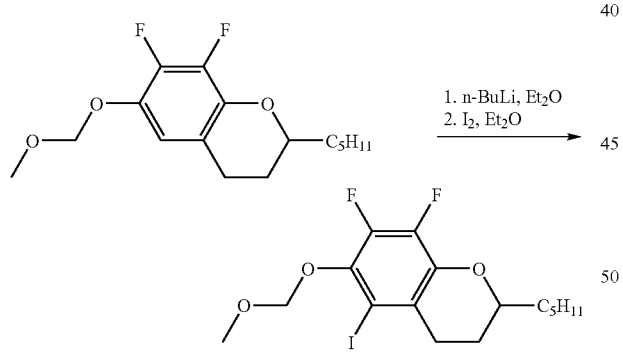

17.7 g (58.9 mmol) of 7,8-difluoro-6-methoxymethoxy-2-pentylchroman are initially introduced in 370 ml of THF, and 47.7 ml (75.9 mmol) of n-BuLi (15% soln. in hexane) are added dropwise at −78° C. When the addition is complete, the mixture is stirred at this temperature for 30 min and subsequently at room temperature for 1 h. The solution is re-cooled to −78° C., and a solution of 17.9 g (70.7 mol) of iodine in 100 ml of THF is added dropwise. The reaction mixture is stirred at room temperature for 90 min and subsequently diluted with MTBE. Sat. sodium hydrogensulfite soln. is added to the mixture, which is subsequently washed with water and sat. sodium chloride soln. The crude product remaining after drying using sodium sulfate and removal of the solvents is purified by column chromatography (SiO$_2$, n-heptane:MTBE=3:1), giving 7,8-difluoro-5-iodo-6-methoxymethoxy-2-pentylchroman as a brown oil.

3.7. Preparation of 7,8-difluoro-5-iodo-2-pentylchroman-6-ol

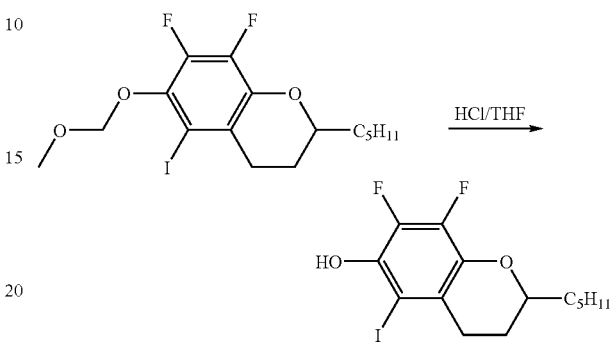

9.2 ml of conc. HCl are added to a solution of 21.4 g (50.2 mmol) of 7,8-difluoro-5-iodo-6-methoxymethoxy-2-pentylchroman in 90 ml of THF, and the mixture is stirred at room temperature for 17 h. The batch is diluted with MTBE, and the solution is washed with water. The aqueous phase is extracted with MTBE, and the combined organic phases are washed with water and sat. sodium chloride soln. The solution is dried using sodium sulfate and concentrated to dryness. The crude product is purified by column chromatography (SiO$_2$, n-heptane:MTBE=1:1), giving 7,8-difluoro-5-iodo-2-pentylchroman-6-ol as a beige solid.

3.8. Preparation of 7,8-difluoro-2-pentyl-5-(4-propylcyclohexylethynyl)chroman-6-ol

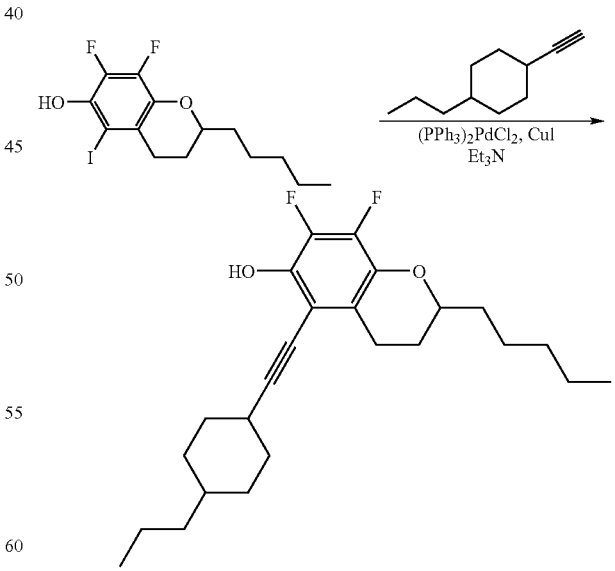

8.0 g (20.9 mmol) of 7,8-difluoro-5-iodo-2-pentylchroman-6-ol are stirred at 50° C. for 19 h together with 4.72 g (31.4 mmol) of 1-ethynyl-4-propylcyclohexane in the presence of 441 mg (0.63 mmol) of bis(triphenylphosphine)palladium(II) chloride and 120 mg (0.63 mmol) of copper(I)

iodide in 90 ml of triethylamine. After cooling, the batch is added to ice/water and acidified using hydrochloric acid. The mixture is extracted a number of times with MTBE, and the combined extracts are washed with water and sat. sodium chloride soln. The solution is dried using sodium sulfate and concentrated to dryness. The residue is purified by column chromatography (SiO$_2$, 1-chlorobutane). The phenol obtained is used directly for the following reaction.

3.9. Preparation of 4,5-difluoro-7-pentyl-2-(4-propylcyclohexyl)-8,9-dihydro-7H-furo[3,2-f]chromene 3.00 g (7.41 mmol) of 7,8-difluoro-2-pentyl-5-(4-propylcyclohexylethynyl)chroman-6-ol are initially introduced together with 0.11 ml (0.74 mmol) of TMEDA, and 4.1 ml (4.1 mmol) of diethylzinc (1 M soln. in heptane) are added to the mixture at 3° C. When the evolution of gas has subsided, 11 ml of toluene are added, and the batch is refluxed for 40 h. The solution is added to sat. ammonium chloride soln., and the mixture is extracted with toluene. The combined organic phases are washed with water and sat. sodium chloride soln. and dried using sodium sulfate. The solution is concentrated to dryness, and the residue is purified by column chromatography (SiO$_2$, 1-chlorobutane:pentane=2:1). Further purification is carried out by repeated recrystallisation from ethanol at reduced temperature, giving 4,5-difluoro-7-pentyl-2-(4-propylcyclohexyl)-8,9-dihydro-7H-furo[3,2-f]chromene as a colourless solid having the phase sequence C 56° C. N 62° C. I (Δε=−6.8).

$^1$H-NMR (400 MHz, CHCl$_3$): δ=6.22 (dd, 1H, J=3.2 Hz, J=0.8 Hz, 1-H), 4.05-3.99 (m, 1H, 7-H), 2.83-2.79 (m, 2H, 9-H), 2.67 (tm, 1H, J=12.0 Hz, H$_{aliph.}$), 2.17-2.04 (m, 3H, H$_{aliph.}$), 1.90-1.75 (m, 4H, H$_{aliph.}$), 1.67-1.53 (m, 4H, H$_{aliph.}$), 1.50-1.40 (m, 2H, H$_{aliph.}$), 1.38-1.26 (m, 6H, H$_{aliph.}$), 1.25-1.18 (m, 2H, H$_{aliph.}$), 1.09-0.99 (m, 2H, H$_{aliph.}$), 0.93-0.88 (m, 6H, CH$_2$CH$_3$).

$^{19}$F-NMR (376 MHz, CHCl$_3$): δ=−162.9 (dm, 1F, J=19.2 Hz), −166.2 (d, 1F, J=19.2 Hz).

MS (EI): m/e (%)=404 (98, M$^+$), 307 (100).

Example 4

4,5-Difluoro-7-pentyl-2-(4-propylcyclohexyl)-1,7,8,9-tetrahydro-2H-furo[3,2-f]chromene

4.1. Preparation of 4,5-difluoro-7-pentyl-2-(4-propylcyclohexyl)-1,7,8,9-tetrahydro-2H-furo[3,2-f]chromene

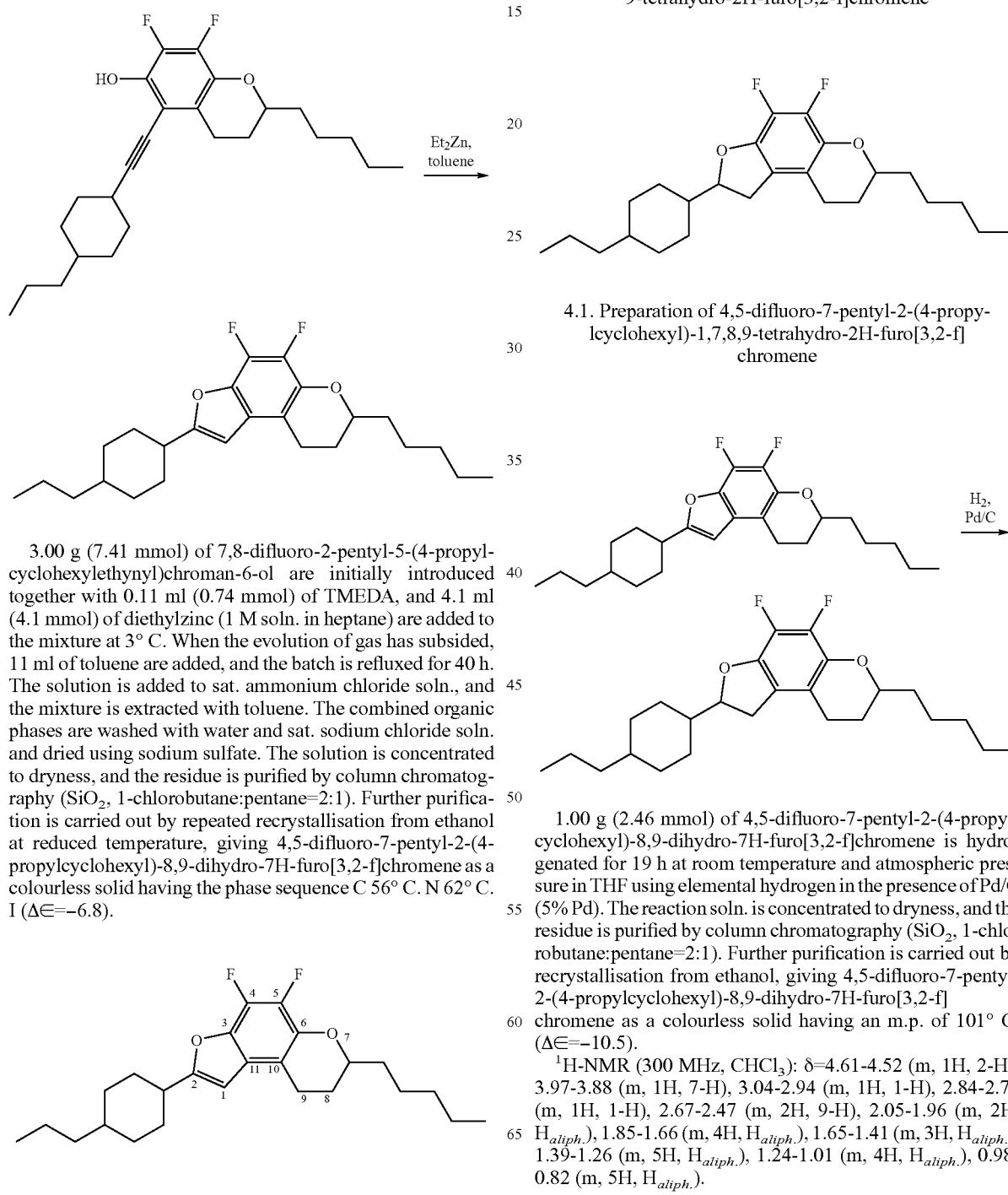

1.00 g (2.46 mmol) of 4,5-difluoro-7-pentyl-2-(4-propylcyclohexyl)-8,9-dihydro-7H-furo[3,2-f]chromene is hydrogenated for 19 h at room temperature and atmospheric pressure in THF using elemental hydrogen in the presence of Pd/C (5% Pd). The reaction soln. is concentrated to dryness, and the residue is purified by column chromatography (SiO$_2$, 1-chlorobutane:pentane=2:1). Further purification is carried out by recrystallisation from ethanol, giving 4,5-difluoro-7-pentyl-2-(4-propylcyclohexyl)-8,9-dihydro-7H-furo[3,2-f]chromene as a colourless solid having an m.p. of 101° C. (Δε=−10.5).

$^1$H-NMR (300 MHz, CHCl$_3$): δ=4.61-4.52 (m, 1H, 2-H), 3.97-3.88 (m, 1H, 7-H), 3.04-2.94 (m, 1H, 1-H), 2.84-2.74 (m, 1H, 1-H), 2.67-2.47 (m, 2H, 9-H), 2.05-1.96 (m, 2H, H$_{aliph.}$), 1.85-1.66 (m, 4H, H$_{aliph.}$), 1.65-1.41 (m, 3H, H$_{aliph.}$), 1.39-1.26 (m, 5H, H$_{aliph.}$), 1.24-1.01 (m, 4H, H$_{aliph.}$), 0.98-0.82 (m, 5H, H$_{aliph.}$).

$^{19}$F-NMR (282 MHz, CHCl$_3$): δ=−161.9 (dm, 1F, J=19.2 Hz), −163.8 (d, 1F, J=19.2 Hz).

MS (EI): m/e (%)=406 (100, M$^+$).

Example 5

4,5-Difluoro-2-methyl-7-propyl-8,9-dihydro-7H-furo[3,2-f]-chromene

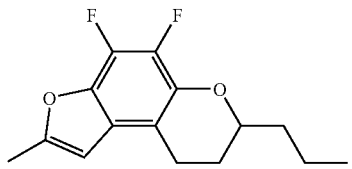

5.1. Preparation of 5-bromo-1,2-difluoro-3-prop-2-ynyloxybenzene

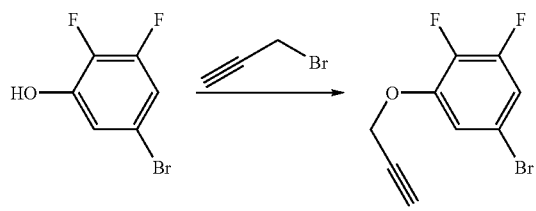

50.0 g (0.24 mol) of 5-bromo-2,3-difluorophenol are refluxed for 3 h together with 32.0 ml (0.29 mol) of propargyl bromide (80% soln. in toluene) and 39.7 g (0.29 mol) of potassium carbonate in 860 ml of ethyl methyl ketone. The batch is filtered, and the filter residue is washed with MTBE. The filtrate is concentrated to dryness, and the residue is purified by column chromatography (SiO$_2$, n-heptane:MTBE=3:1).

5.2. Preparation of 4-bromo-6,7-difluoro-2-methylbenzofuran

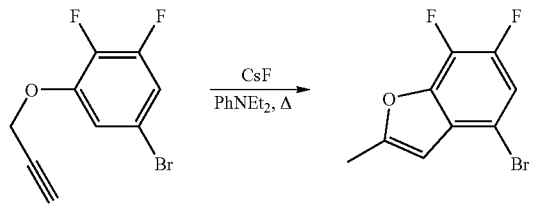

51.9 g (0.21 mol) of 5-bromo-1,2-difluoro-3-prop-2-ynyloxybenzene are heated at 205° C. for 4 h together with 20.7 g (0.14 mol) of caesium fluoride in 300 ml of N,N-diethylaniline. The batch is diluted with MTBE and washed a number of times with 1 N HCl. The solution is dried using sodium sulfate and concentrated to dryness. The residue is purified by column chromatography (SiO$_2$, n-heptane:1-chlorobutane=3:1), giving 4-bromo-6,7-difluoro-2-methylbenzofuran as a yellow solid.

5.3. Preparation of 4-bromo-6,7-difluoro-2-methylbenzofuran-5-ol

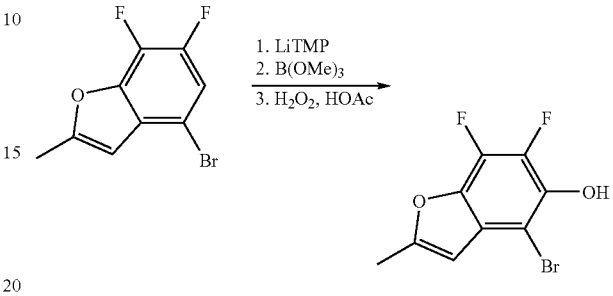

107.1 ml (0.17 mol) of n-BuLi (15% soln. in hexane) are initially introduced at −70° C. in 150 ml of THF, and 29.0 ml (0.17 mol) of 2,2,6,6-tetramethylpiperidine are added. After 30 min at this temperature, a solution of 38.3 g (0.16 mol) of 4-bromo-6,7-difluoro-2-methylbenzofuran in 100 ml of THF is metered in. After 3 h at this temperature, 19.1 ml (0.17 mol) of trimethyl borate are added dropwise, and the batch is warmed to room temperature. 40 ml of dilute acetic acid (about 30%) are added, and 40 ml of aqueous hydrogen peroxide soln. (35%) are carefully added to the batch. When the addition is complete, the mixture is stirred at 20° C. for 18 h. Water is added, and the batch is acidified using HCl. The solution is extracted a number of times with MTBE, and the combined organic phases are washed successively with water, sat. sodium chloride soln. and ammonium iron(II) sulfate soln. The solution is dried using sodium sulfate and concentrated to dryness. The crude product is purified by column chromatography (SiO$_2$, n-heptane:1-chlorobutane=2:1), giving 4-bromo-6,7-difluoro-2-methylbenzofuran-5-ol as a beige solid.

5.4. Preparation of 4-bromo-6,7-difluoro-5-(2-methoxyethoxymethoxy)-2-methylbenzofuran

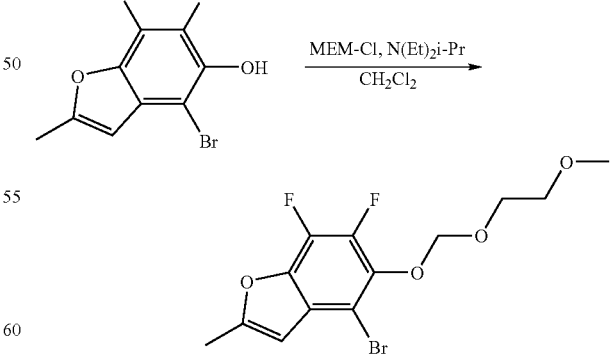

23.0 g (87.4 mmol) of 4-bromo-6,7-difluoro-2-methylbenzofuran-5-ol are initially introduced at 0° C. in 120 ml of dichloromethane, and 17.9 ml (0.11 mol) of N-ethyldiisopropylamine and 11.9 ml (0.11 mol) of MEMCl are added successively. The batch is stirred at 20° C. for 16 h, and excess MEMCl is quenched using triethylamine. Water is added, and the organic phase is separated off. The aqueous phase is extracted with dichloromethane, and the combined organic phases are washed with water and sat. sodium chloride soln. The solution is dried using sodium sulfate and concentrated to dryness. The crude product is purified by column chromatography (SiO$_2$, n-heptane:MTBE=2:1).

5.5. Preparation of 6,7-difluoro-5-(2-methoxyethoxymethoxy)-2-methylbenzofuran-4-carbaldehyde

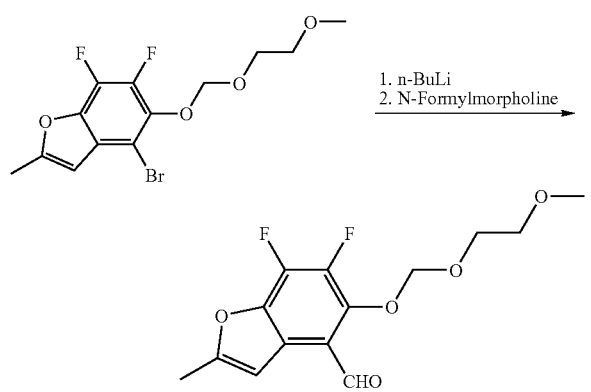

27.2 g (77.5 mmol) of 4-bromo-6,7-difluoro-5-(2-methoxyethoxymethoxy)-2-methylbenzofuran are initially introduced at −75° C. in 500 ml of THF, and 52.0 ml (85.2 mmol) of n-BuLi (15% soln. in hexane) are added. After 2 h at this temperature, 15.5 ml (155 mmol) of N-formylmorpholine are metered in, and the batch is stirred at this temperature for 2 h. The reaction soln. is slowly warmed to −10° C. and hydrolysed using dil. HCl. The batch is extracted with MTBE, and the combined organic phases are washed with sat. sodium chloride soln. The solution is dried using sodium sulfate and concentrated to dryness. The residue is purified by column chromatography (SiO$_2$, n-heptane:MTBE=2:1→n-heptane:MTBE=1:1).

5.6. Preparation of 6,7-difluoro-5-hydroxy-2-methylbenzofuran-4-carbaldehyde

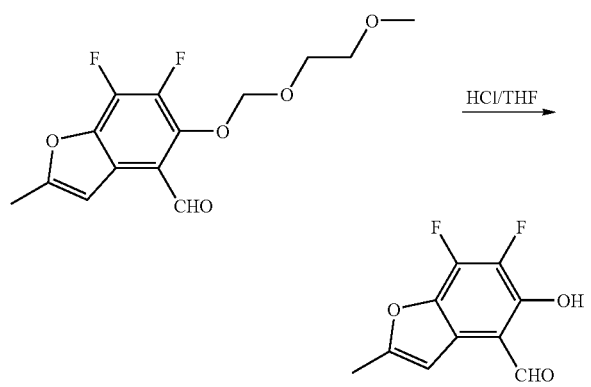

18.0 g (60.0 mmol) of 6,7-difluoro-5-(2-methoxyethoxymethoxy)-2-methylbenzofuran-4-carbaldehyde are stirred for 17 h at 20° C. together with 11.0 ml of conc. HCl in 100 ml of THF. The reaction soln. is diluted with MTBE and washed with water. The aqueous phase is extracted with MTBE, and the combined organic phases are washed successively with water and sat. sodium chloride soln. The solution is dried using sodium sulfate and concentrated to dryness. The crude product is purified by column chromatography (SiO$_2$, 1-chlorobutane), giving 6,7-difluoro-5-hydroxy-2-methylbenzofuran-4-carbaldehyde as a yellow crystalline solid.

5.7. Preparation of 4,5-difluoro-2-methyl-7-propyl-7H-furo[3,2-f]chromene

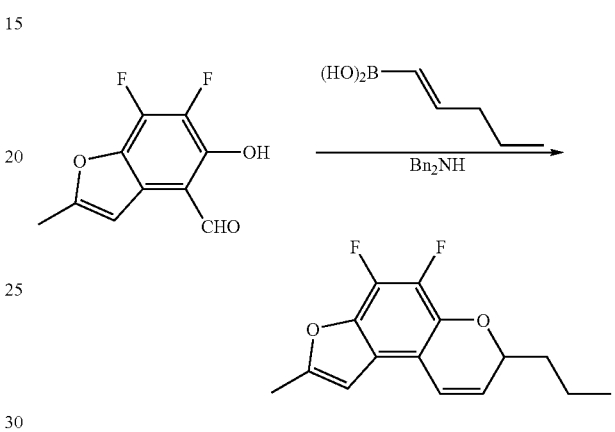

4.0 g (18.9 mmol) of 6,7-difluoro-5-hydroxy-2-methylbenzofuran-4-carbaldehyde are stirred for 20 h at 90° C. together with 2.79 g (24.5 mmol) of 1-penteneboronic acid and 0.72 ml (3.73 mmol) of dibenzylamine in 95 ml of 1,4-dioxane. Water is added to the reaction mixture, which is then extracted with MTBE. The organic phase is separated off, and the aqueous phase is extracted with MTBE. The combined organic phases are washed with water and sat. sodium chloride soln. The solution is dried using sodium sulfate and concentrated to dryness. The crude product is firstly purified by column chromatography (SiO$_2$, 1-chlorobutane) and subsequently crystallised from methanol, giving 4,5-difluoro-2-methyl-7-propyl-7H-furo[3,2-f]chromene as a yellow, crystalline solid.

5.8. Preparation of 4,5-difluoro-2-methyl-7-propyl-8,9-dihydro-7H-furo[3,2-f]-chromene

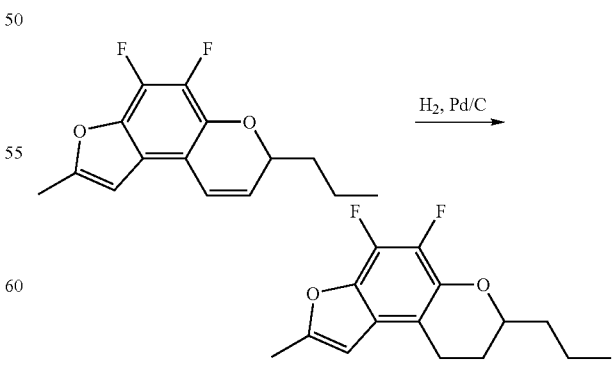

3.5 g (13.2 mmol) of 4,5-difluoro-2-methyl-7-propyl-7H-furo[3,2-f]chromene are hydrogenated for a few minutes in toluene using elemental hydrogen in the presence of Pd/C (5% Pd). The reaction soln. is concentrated to dryness, and the residue is purified by column chromatography (SiO$_2$, n-heptane:1-chlorobutane=2:1). The further purification is carried out by recrystallisation from ethanol and subsequent absorptive (SiO$_2$, n-heptane:1-chlorobutane=3:1) filtration, giving 4,5-difluoro-2-methyl-7-propyl-8,9-dihydro-7H-furo[3,2-f]chromene as a colourless solid having an m.p. of 75° C. (Δ∈c=−7.8).

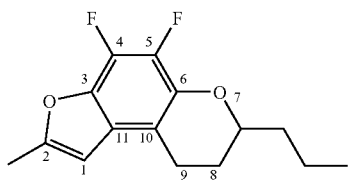

$^1$H-NMR (250 MHz, CHCl$_3$): δ=6.26 (q, 1H, $^4$J=1.0 Hz, 1-H), 4.09-4.00 (m, 1H, 7-H), 2.83-2.77 (m, 2-H, 9-H), 2.43 (s, 3H, 2-Me), 2.12-2.02 (m, 1H, 8-H), 1.86-1.70 (m, 2H, H$_{aliph.}$), 1.69-1.45 (m, 3H, 8-H, H$_{aliph.}$), 0.99 (t, 3H, CH$_2$CH$_2$CH$_3$).
$^{19}$F-NMR (235 MHz, CHCl$_3$): δ=−164.2 (dm, 1F, J=19.5 Hz), −167.4 (d, 1F, J=19.5 Hz).
MS (EI): m/e (%)=266 (37, M$^+$), 223 (6, [M-C$_3$H$_7$]$^+$), 197 (100).

Example 6

4,5-Difluoro-2-methyl-7-propyl-1,7,8,9-tetrahydro-2H-furo[3,2-f]-chromene

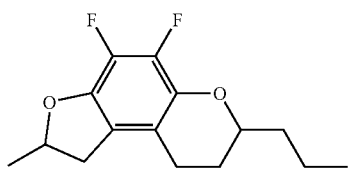

6.1. Preparation of 4,5-difluoro-2-methyl-7-propyl-1,7,8,9-tetrahydro-2H-furo-[3,2-f]chromene

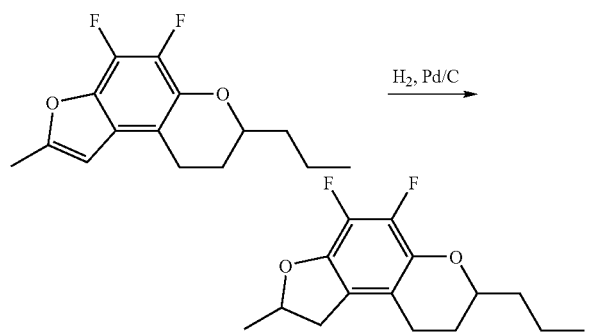

2.0 g (7.51 mmol) of 4,5-difluoro-2-methyl-7-propyl-8,9-dihydro-7H-furo-[3,2-f]chromene are hydrogenated for 18 h at elevated temperature in THF using elemental hydrogen in the presence of Pd/C (5% Pd). The reaction soln. is concentrated to dryness, and the residue is purified by column chromatography (SiO$_2$, 1-chlorobutane), giving 4,5-difluoro-2-methyl-7-propyl-1,7,8,9-tetrahydro-2H-furo[3,2-f]chromene as a colourless solid having an m.p. of 87° C. (Δ∈=−10.1).

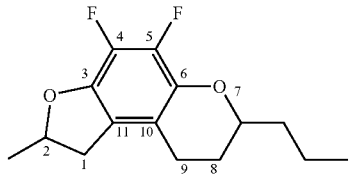

$^1$H-NMR (250 MHz, CHCl$_3$): δ=5.06-4.92 (m, 1H, 2-H), 4.00-3.90 (m, 1H, 7-H), 3.21-3.09 (m, 1H, 1-H), 2.71-2.46 (m, 3H, 1-H, 9-H), 2.06-1.95 (m, 1H, 8-H), 1.80-1.53 (m, 5H, 8-H, CH$_2$CH$_2$CH$_3$), 1.48 (d, 3H, J=6.3 Hz, 2-Me), 0.97 (t, 3H, J=7.0 Hz, CH$_2$CH$_2$CH$_3$).
$^{19}$F-NMR (235 MHz, CHCl$_3$): δ=−160.6 (dm, 1F, J=19.5 Hz), −162.8 (d, 1F, J=19.5 Hz).
MS (EI): m/e (%)=268 (89, M$^+$), 225 (6, [M-C$_3$H$_7$]$^+$), 199 (100).

Example 7

4,5-Difluoro-2-methyl-7-pentyl-8,9-dihydro-7H-furo[3,2-f]-chromene

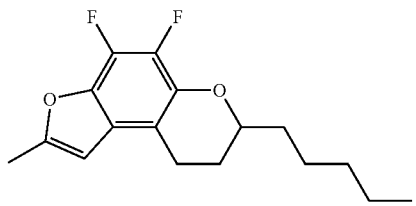

7.1. Preparation of 4,5-difluoro-2-methyl-7-pentyl-7H-furo[3,2-f]chromene

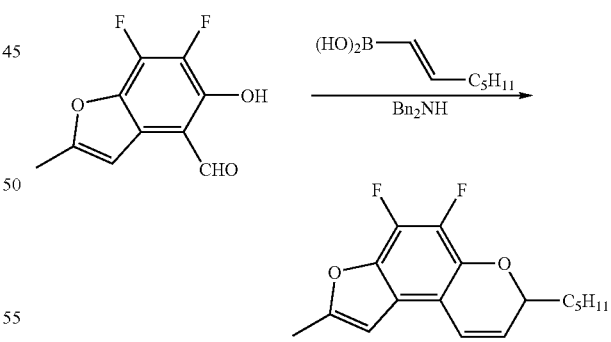

4.0 g (18.6 mmol) of 6,7-difluoro-5-hydroxy-2-methyl-benzofuran-4-carbaldehyde are stirred for 20 h at 90° C. together with 3.21 g (22.6 mmol) of 1-hepteneboronic acid and 0.72 ml (3.73 mmol) of dibenzylamine in 95 ml of 1,4-dioxane. Water is added to the reaction mixture, which is then extracted with MTBE. The organic phase is separated off, and the aqueous phase is extracted with MTBE. The combined organic phases are washed with water and sat. sodium chloride soln. The solution is dried using sodium sulfate and concentrated to dryness. The crude product is firstly purified

7.2. Preparation of 4,5-difluoro-2-methyl-7-pentyl-8,9-dihydro-7H-furo[3,2-f]-chromene

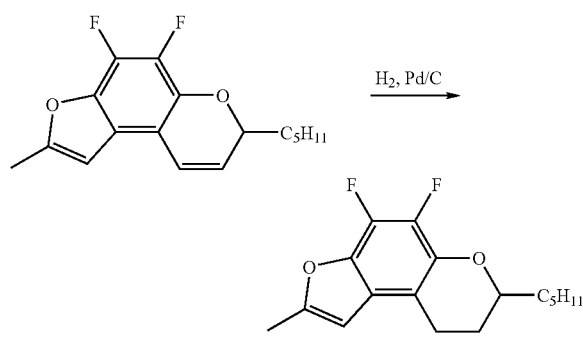

2.8 g (9.58 mmol) of 4,5-difluoro-2-methyl-7-pentyl-7H-furo[3,2-f]chromene are hydrogenated for a few minutes in toluene using elemental hydrogen in the presence of Pd/C (5% Pd). The reaction soln. is concentrated to dryness, and the residue is purified by column chromatography (SiO$_2$, n-heptane:1-chlorobutane=2:1). The further purification is carried out by recrystallisation from ethanol, giving 4,5-difluoro-2-methyl-7-pentyl-8,9-dihydro-7H-furo[3,2-f]chromene as a colourless solid having an m.p. of 61° C. (Δ∈=−6.7).

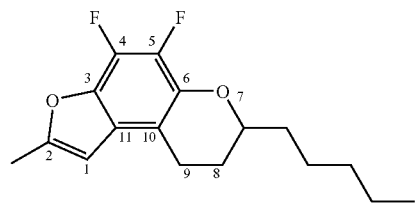

$^1$H-NMR (500 MHz, CHCl$_3$): δ=6.27 (bs, 1H, 1-H), 4.06-4.01 (m, 1H, 7-H), 2.82-2.79 (m, 2H, 9-H), 2.44 (s, 3H, 2-Me), 2.10-2.05 (m, 1H, H$_{aliph.}$), 1.86-1.75 (m, 2H, H$_{aliph.}$), 1.67-1.60 (m, 1H, H$_{aliph.}$), 1.59-1.54 (m, 1H, H$_{aliph.}$), 1.51-1.43 (m, 1H, H$_{aliph.}$), 1.37-1.33 (m, 4H, H$_{aliph.}$), 0.91 (t, 3H, J=7.0 Hz, (CH$_2$)$_4$CH$_3$).

$^{19}$F-NMR (235 MHz, CHCl$_3$): δ=−163.2 (dm, 1F, J=19.5 Hz), −166.4 (d, 1F, J=19.5 Hz).

MS (EI): m/e (%)=294 (27, M$^+$), 223 (6, [M-C$_5$H$_{11}$]$^+$), 197 (100).

8.1. Preparation of 4,5-difluoro-2-methyl-7-pentyl-1,7,8,9-tetrahydro-2H-furo-[3,2-f]chromene

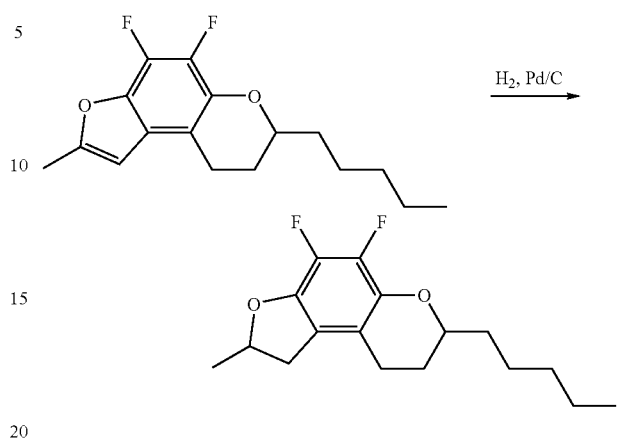

2.0 g (7.51 mmol) of 4,5-difluoro-2-methyl-7-pentyl-8,9-dihydro-7H-furo-[3,2-f]chromene are hydrogenated for 18 h at elevated temperature in THF using elemental hydrogen in the presence of Pd/C (5% Pd). The reaction soln. is concentrated to dryness, and the residue is purified by column chromatography (SiO$_2$, n-heptane:MTBE=4:1). Further purification is carried out by recrystallisation from ethanol at 5° C., giving 4,5-difluoro-2-methyl-7-pentyl-1,7,8,9-tetrahydro-2H-furo[3,2-f]chromene as a colourless solid having an m.p. of 76° C. (Δ∈=−8.2).

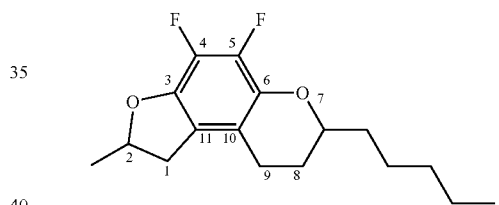

$^1$H-NMR (250 MHz, CHCl$_3$): δ=5.07-4.92 (m, 1H, 2-H), 3.99-3.88 (m, 1H, 7-H), 3.22-3.09 (m, 1H, 1-H), 2.71-2.53 (m, 3H, 1-H, 9-H), 2.06-1.96 (m, 1H, 8-H), 1.80-1.51 (m, 5H, H$_{aliph.}$), 1.48 (d, 3H, J=6.3 Hz, 2-Me), 1.36-1.32 (m, 4H, H$_{aliph.}$), 0.91 (t, 3H, J=7.0 Hz, (CH$_2$)$_4$CH$_3$).

$^{19}$F-NMR (235 MHz, CHCl$_3$): δ=−162.1 (dm, 1F, J=19.5 Hz), −164.2 (d, 1F, J=19.5 Hz).

MS (EI): m/e (%)=296 (98, M$^+$), 199 (100).

Example 9

4,5-Difluoro-7-pentyl-2-(4-propylphenyl)-8,9-dihydro-7H-furo-[3,2-f]chromene

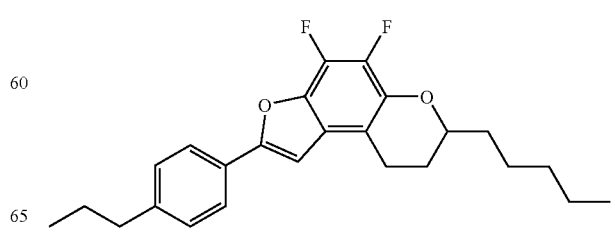

9.1. Preparation of 4,5-difluoro-7-pentyl-2-(4-propylphenyl)-8,9-dihydro-7H-furo[3,2-f]chromene

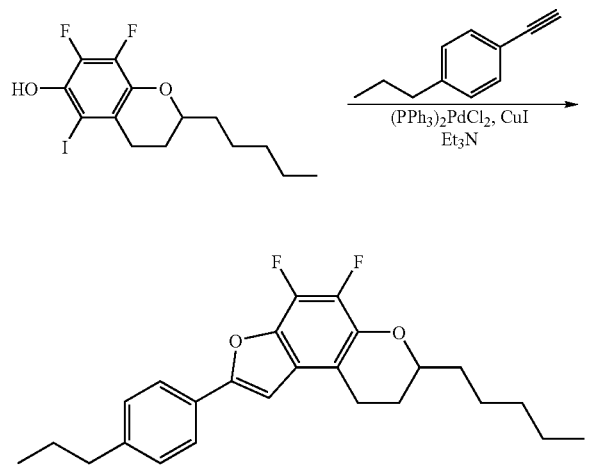

2.0 g (5.23 mmol) of 7,8-difluoro-5-iodo-2-pentylchroman-6-ol are firstly stirred for 6 h at 60° C. together with 1.13 g (7.85 mmol) of ethynyl-n-propylbenzene in the presence of 110 mg (0.16 mmol) of bis(triphenylphosphine)palladium(II) chloride and 30 mg (0.16 mmol) of copper(I) iodide in 22 ml of triethylamine. The mixture is subsequently refluxed for 18 h. After cooling, the batch is added to ice/water and acidified using hydrochloric acid. The mixture is extracted a number of times with MTBE, and the combined extracts are washed with water and sat. sodium chloride soln. The solution is dried using sodium sulfate and concentrated to dryness. The residue is purified by column chromatography ($SiO_2$, pentane: 1-chlorobutane=10:1). Further purification is carried out by recrystallisation from ethanol at 5° C., giving 4,5-difluoro-7-pentyl-2-(4-propylphenyl)-8,9-dihydro-7H-furo[3,2-f]chromene as a solid having the phase sequence Tg −31° C. C 70° C. N 79° C. I (Δε=−7.2).

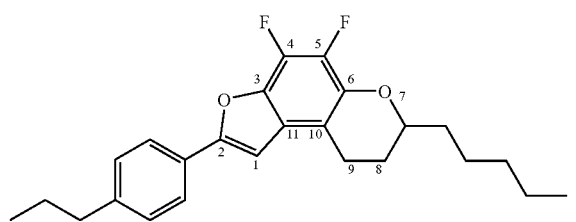

$^1$H-NMR (250 MHz, $CHCl_3$): δ=7.72 (d, 2H, J=8.3 Hz, $H_{arom.}$), 7.23 (d, 2H, J=8.3 Hz, $H_{arom.}$), 6.81 (d, 1H, J=2.7 Hz), 4.08-4.00 (m, 1H, 7-H), 2.88-2.83 (m, 2H, 9-H), 2.62 (t, 2H, J=7.8 Hz, $H_{benzyl.}$), 2.14-2.05 (m, 1H, $H_{aliph.}$), 1.90-1.76 (m, 2H, $H_{aliph.}$), 1.73-1.61 (m, 4H, $H_{aliph.}$), 1.57-1.44 (m, 1H, $H_{aliph.}$), 1.39-1.33 (m, 4H, $H_{aliph.}$), 0.98-0.89 (m, 6H, $H_{aliph.}$).

$^{19}$F-NMR (282 MHz, $CHCl_3$): δ=−162.5 (dd, 1F, J=19.2 Hz, J=1.9 Hz), −164.3 (d, 1F, J=19.2 Hz).

MS (EI): m/e (%)=398 (100, M$^+$), 301 (97).

Examples 10 to 86

The following are prepared analogously to Examples 1, 3 and 9:

| No. | $R^1$ | $R^2$ | Phase sequence T/° C. |
|---|---|---|---|
| 10 | $CH_3$ | $CH_3$ | |
| 11 | $CH_3$ | $C_2H_5$ | |
| 12 | $CH_3$ | n-$C_3H_7$ | |
| 13 | $CH_3$ | n-$C_4H_9$ | |
| 15 | $CH_3$ | n-$C_5H_{11}$ | |
| 16 | $CH_3$ | n-$C_6H_{13}$ | |
| 17 | $CH_3$ | n-$C_7H_{15}$ | |
| 18 | $C_2H_5$ | $CH_3$ | |
| 19 | $C_2H_5$ | $C_2H_5$ | |
| 20 | $C_2H_5$ | n-$C_3H_7$ | |
| 21 | $C_2H_5$ | n-$C_4H_9$ | |
| 22 | $C_2H_5$ | n-$C_5H_{11}$ | |
| 23 | $C_2H_5$ | n-$C_6H_{13}$ | |
| 24 | $C_2H_5$ | n-$C_7H_{15}$ | |
| 25 | n-$C_3H_7$ | $CH_3$ | |
| 26 | n-$C_3H_7$ | $C_2H_5$ | |
| 27 | n-$C_3H_7$ | n-$C_3H_7$ | |
| 28 | n-$C_3H_7$ | n-$C_4H_9$ | |
| 3 | n-$C_3H_7$ | n-$C_5H_{11}$ | C 56 N 62 I |
| 29 | n-$C_3H_7$ | n-$C_6H_{13}$ | |
| 30 | n-$C_3H_7$ | n-$C_7H_{15}$ | |
| 31 | n-$C_4H_9$ | $CH_3$ | |
| 32 | n-$C_4H_9$ | $C_2H_5$ | |
| 33 | n-$C_4H_9$ | n-$C_3H_7$ | |
| 34 | n-$C_4H_9$ | n-$C_4H_9$ | |
| 35 | n-$C_4H_9$ | n-$C_5H_{11}$ | |
| 36 | n-$C_4H_9$ | n-$C_6H_{13}$ | |
| 37 | n-$C_4H_9$ | n-$C_7H_{15}$ | |
| 38 | n-$C_5H_{11}$ | $CH_3$ | |
| 39 | n-$C_5H_{11}$ | $C_2H_5$ | |
| 40 | n-$C_5H_{11}$ | n-$C_3H_7$ | |
| 41 | n-$C_5H_{11}$ | n-$C_4H_9$ | |
| 42 | n-$C_5H_{11}$ | n-$C_5H_{11}$ | |
| 43 | n-$C_5H_{11}$ | n-$C_6H_{13}$ | |
| 44 | n-$C_5H_{11}$ | n-$C_7H_{15}$ | |
| 45 | n-$C_6H_{13}$ | $CH_3$ | |
| 46 | n-$C_6H_{13}$ | $C_2H_5$ | |
| 47 | n-$C_6H_{13}$ | n-$C_3H_7$ | |
| 48 | n-$C_6H_{13}$ | n-$C_4H_9$ | |
| 49 | n-$C_6H_{13}$ | n-$C_5H_{11}$ | |
| 50 | n-$C_6H_{13}$ | n-$C_6H_{13}$ | |
| 51 | n-$C_6H_{13}$ | n-$C_7H_{15}$ | |
| 52 | n-$C_7H_{15}$ | $CH_3$ | |
| 53 | n-$C_7H_{15}$ | $C_2H_5$ | |
| 54 | n-$C_7H_{15}$ | n-$C_3H_7$ | |
| 55 | n-$C_7H_{15}$ | n-$C_4H_9$ | |
| 56 | n-$C_7H_{15}$ | n-$C_5H_{11}$ | |
| 57 | n-$C_7H_{15}$ | n-$C_6H_{13}$ | |
| 58 | n-$C_7H_{15}$ | n-$C_7H_{15}$ | |
| 59 | $CH_3O$ | $CH_3$ | |
| 60 | $CH_3O$ | $C_2H_5$ | |
| 61 | $CH_3O$ | n-$C_3H_7$ | |
| 62 | $CH_3O$ | n-$C_4H_9$ | |
| 63 | $CH_3O$ | n-$C_5H_{11}$ | |
| 64 | $CH_3O$ | n-$C_6H_{13}$ | |
| 65 | $CH_3O$ | n-$C_7H_{15}$ | |
| 66 | $C_2H_5O$ | $CH_3$ | |
| 67 | $C_2H_5O$ | $C_2H_5$ | |
| 68 | $C_2H_5O$ | n-$C_3H_7$ | |

-continued

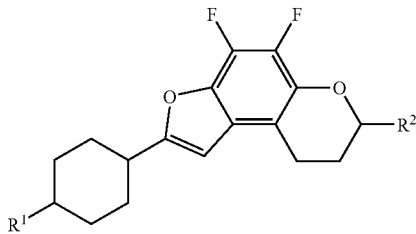

| No. | R¹ | R² | Phase sequence T/° C. |
|---|---|---|---|
| 69 | $C_2H_5O$ | $n\text{-}C_4H_9$ | |
| 70 | $C_2H_5O$ | $n\text{-}C_5H_{11}$ | |
| 71 | $C_2H_5O$ | $n\text{-}C_6H_{13}$ | |
| 72 | $C_2H_5O$ | $n\text{-}C_7H_{15}$ | |
| 73 | $CH_2=CH$ | $CH_3$ | |
| 74 | $CH_2=CH$ | $C_2H_5$ | |
| 75 | $CH_2=CH$ | $n\text{-}C_3H_7$ | |
| 76 | $CH_2=CH$ | $n\text{-}C_4H_9$ | |
| 77 | $CH_2=CH$ | $n\text{-}C_5H_{11}$ | |
| 78 | $CH_2=CH$ | $n\text{-}C_6H_{13}$ | |
| 79 | $CH_2=CH$ | $n\text{-}C_7H_{15}$ | |
| 80 | $CH_3-CH=CH$ | $CH_3$ | |
| 81 | $CH_3-CH=CH$ | $C_2H_5$ | |
| 82 | $CH_3-CH=CH$ | $n\text{-}C_3H_7$ | |
| 83 | $CH_3-CH=CH$ | $n\text{-}C_4H_9$ | |
| 84 | $CH_3-CH=CH$ | $n\text{-}C_5H_{11}$ | |
| 85 | $CH_3-CH=CH$ | $n\text{-}C_6H_{13}$ | |
| 86 | $CH_3-CH=CH$ | $n\text{-}C_7H_{15}$ | |

Note:
* values extrapolated from 10% solution in ZLI-4792 or ZLI-2857 (Δε).

Examples 87 to 163

The following are prepared analogously to Examples 1, 3 and 9:

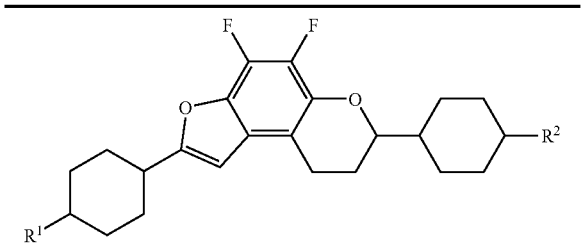

| No. | R¹ | R² | Phase sequence T/° C. |
|---|---|---|---|
| 87 | $CH_3$ | $CH_3$ | |
| 88 | $CH_3$ | $C_2H_5$ | |
| 89 | $CH_3$ | $n\text{-}C_3H_7$ | |
| 90 | $CH_3$ | $n\text{-}C_4H_9$ | |
| 91 | $CH_3$ | $n\text{-}C_5H_{11}$ | |
| 92 | $CH_3$ | $n\text{-}C_6H_{13}$ | |
| 93 | $CH_3$ | $n\text{-}C_7H_{15}$ | |
| 94 | $C_2H_5$ | $CH_3$ | |
| 95 | $C_2H_5$ | $C_2H_5$ | |
| 96 | $C_2H_5$ | $n\text{-}C_3H_7$ | |
| 97 | $C_2H_5$ | $n\text{-}C_4H_9$ | |
| 98 | $C_2H_5$ | $n\text{-}C_5H_{11}$ | |
| 99 | $C_2H_5$ | $n\text{-}C_6H_{13}$ | |
| 100 | $C_2H_5$ | $n\text{-}C_7H_{15}$ | |
| 101 | $n\text{-}C_3H_7$ | $CH_3$ | |
| 102 | $n\text{-}C_3H_7$ | $C_2H_5$ | |
| 103 | $n\text{-}C_3H_7$ | $n\text{-}C_3H_7$ | |

-continued

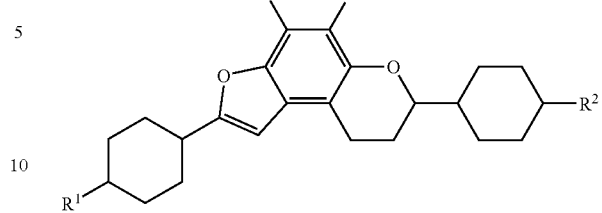

| No. | R¹ | R² | Phase sequence T/° C. |
|---|---|---|---|
| 104 | $n\text{-}C_3H_7$ | $n\text{-}C_4H_9$ | |
| 105 | $n\text{-}C_3H_7$ | $n\text{-}C_5H_{11}$ | |
| 106 | $n\text{-}C_3H_7$ | $n\text{-}C_6H_{13}$ | |
| 107 | $n\text{-}C_3H_7$ | $n\text{-}C_7H_{15}$ | |
| 108 | $n\text{-}C_4H_9$ | $CH_3$ | |
| 109 | $n\text{-}C_4H_9$ | $C_2H_5$ | |
| 110 | $n\text{-}C_4H_9$ | $n\text{-}C_3H_7$ | |
| 111 | $n\text{-}C_4H_9$ | $n\text{-}C_4H_9$ | |
| 112 | $n\text{-}C_4H_9$ | $n\text{-}C_5H_{11}$ | |
| 113 | $n\text{-}C_4H_9$ | $n\text{-}C_6H_{13}$ | |
| 114 | $n\text{-}C_4H_9$ | $n\text{-}C_7H_{15}$ | |
| 115 | $n\text{-}C_5H_{11}$ | $CH_3$ | |
| 116 | $n\text{-}C_5H_{11}$ | $C_2H_5$ | |
| 117 | $n\text{-}C_5H_{11}$ | $n\text{-}C_3H_7$ | |
| 118 | $n\text{-}C_5H_{11}$ | $n\text{-}C_4H_9$ | |
| 119 | $n\text{-}C_5H_{11}$ | $n\text{-}C_5H_{11}$ | |
| 120 | $n\text{-}C_5H_{11}$ | $n\text{-}C_6H_{13}$ | |
| 121 | $n\text{-}C_5H_{11}$ | $n\text{-}C_7H_{15}$ | |
| 122 | $n\text{-}C_6H_{13}$ | $CH_3$ | |
| 123 | $n\text{-}C_6H_{13}$ | $C_2H_5$ | |
| 124 | $n\text{-}C_6H_{13}$ | $n\text{-}C_3H_7$ | |
| 125 | $n\text{-}C_6H_{13}$ | $n\text{-}C_4H_9$ | |
| 126 | $n\text{-}C_6H_{13}$ | $n\text{-}C_5H_{11}$ | |
| 127 | $n\text{-}C_6H_{13}$ | $n\text{-}C_6H_{13}$ | |
| 128 | $n\text{-}C_6H_{13}$ | $n\text{-}C_7H_{15}$ | |
| 129 | $n\text{-}C_7H_{15}$ | $CH_3$ | |
| 130 | $n\text{-}C_7H_{15}$ | $C_2H_5$ | |
| 131 | $n\text{-}C_7H_{15}$ | $n\text{-}C_3H_7$ | |
| 132 | $n\text{-}C_7H_{15}$ | $n\text{-}C_4H_9$ | |
| 133 | $n\text{-}C_7H_{15}$ | $n\text{-}C_5H_{11}$ | |
| 134 | $n\text{-}C_7H_{15}$ | $n\text{-}C_6H_{13}$ | |
| 135 | $n\text{-}C_7H_{15}$ | $n\text{-}C_7H_{15}$ | |
| 136 | $CH_3O$ | $CH_3$ | |
| 137 | $CH_3O$ | $C_2H_5$ | |
| 138 | $CH_3O$ | $n\text{-}C_3H_7$ | |
| 139 | $CH_3O$ | $n\text{-}C_4H_9$ | |
| 140 | $CH_3O$ | $n\text{-}C_5H_{11}$ | |
| 141 | $CH_3O$ | $n\text{-}C_6H_{13}$ | |
| 142 | $CH_3O$ | $n\text{-}C_7H_{15}$ | |
| 143 | $C_2H_5O$ | $CH_3$ | |
| 144 | $C_2H_5O$ | $C_2H_5$ | |
| 145 | $C_2H_5O$ | $n\text{-}C_3H_7$ | |
| 146 | $C_2H_5O$ | $n\text{-}C_4H_9$ | |
| 147 | $C_2H_5O$ | $n\text{-}C_5H_{11}$ | |
| 148 | $C_2H_5O$ | $n\text{-}C_6H_{13}$ | |
| 149 | $C_2H_5O$ | $n\text{-}C_7H_{15}$ | |
| 150 | $CH_2=CH$ | $CH_3$ | |
| 151 | $CH_2=CH$ | $C_2H_5$ | |
| 152 | $CH_2=CH$ | $n\text{-}C_3H_7$ | |
| 153 | $CH_2=CH$ | $n\text{-}C_4H_9$ | |
| 154 | $CH_2=CH$ | $n\text{-}C_5H_{11}$ | |
| 155 | $CH_2=CH$ | $n\text{-}C_6H_{13}$ | |
| 156 | $CH_2=CH$ | $n\text{-}C_7H_{15}$ | |
| 157 | $CH_3-CH=CH$ | $CH_3$ | |
| 158 | $CH_3-CH=CH$ | $C_2H_5$ | |
| 159 | $CH_3-CH=CH$ | $n\text{-}C_3H_7$ | |
| 160 | $CH_3-CH=CH$ | $n\text{-}C_4H_9$ | |
| 161 | $CH_3-CH=CH$ | $n\text{-}C_5H_{11}$ | |
| 162 | $CH_3-CH=CH$ | $n\text{-}C_6H_{13}$ | |
| 163 | $CH_3-CH=CH$ | $n\text{-}C_7H_{15}$ | |

Note:
* values extrapolated from 10% solution in ZLI-4792 or ZLI-2857 (Δε).

Examples 164 to 239

The following are prepared analogously to Examples 2 and 4:

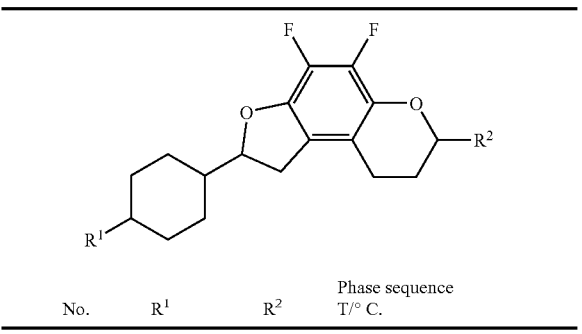

| No. | $R^1$ | $R^2$ | Phase sequence T/° C. |
|---|---|---|---|
| 164 | $CH_3$ | $CH_3$ | |
| 165 | $CH_3$ | $C_2H_5$ | |
| 166 | $CH_3$ | $n-C_3H_7$ | |
| 167 | $CH_3$ | $n-C_4H_9$ | |
| 168 | $CH_3$ | $n-C_5H_{11}$ | |
| 169 | $CH_3$ | $n-C_6H_{13}$ | |
| 170 | $CH_3$ | $n-C_7H_{15}$ | |
| 171 | $C_2H_5$ | $CH_3$ | |
| 172 | $C_2H_5$ | $C_2H_5$ | |
| 173 | $C_2H_5$ | $n-C_3H_7$ | |
| 174 | $C_2H_5$ | $n-C_4H_9$ | |
| 175 | $C_2H_5$ | $n-C_5H_{11}$ | |
| 176 | $C_2H_5$ | $n-C_6H_{13}$ | |
| 177 | $C_2H_5$ | $n-C_7H_{15}$ | |
| 178 | $n-C_3H_7$ | $CH_3$ | |
| 179 | $n-C_3H_7$ | $C_2H_5$ | |
| 180 | $n-C_3H_7$ | $n-C_3H_7$ | |
| 181 | $n-C_3H_7$ | $n-C_4H_9$ | |
| 4 | $n-C_3H_7$ | $n-C_5H_{11}$ | C 101 I |
| 182 | $n-C_3H_7$ | $n-C_6H_{13}$ | |
| 183 | $n-C_3H_7$ | $n-C_7H_{15}$ | |
| 184 | $n-C_4H_9$ | $CH_3$ | |
| 185 | $n-C_4H_9$ | $C_2H_5$ | |
| 186 | $n-C_4H_9$ | $n-C_3H_7$ | |
| 187 | $n-C_4H_9$ | $n-C_4H_9$ | |
| 188 | $n-C_4H_9$ | $n-C_5H_{11}$ | |
| 189 | $n-C_4H_9$ | $n-C_6H_{13}$ | |
| 190 | $n-C_4H_9$ | $n-C_7H_{15}$ | |
| 191 | $n-C_5H_{11}$ | $CH_3$ | |
| 192 | $n-C_5H_{11}$ | $C_2H_5$ | |
| 193 | $n-C_5H_{11}$ | $n-C_3H_7$ | |
| 208 | $n-C_5H_{11}$ | $n-C_4H_9$ | |
| 209 | $n-C_5H_{11}$ | $n-C_5H_{11}$ | |
| 210 | $n-C_5H_{11}$ | $n-C_6H_{13}$ | |
| 211 | $n-C_5H_{11}$ | $n-C_7H_{15}$ | |
| 212 | $n-C_6H_{13}$ | $CH_3$ | |
| 213 | $n-C_6H_{13}$ | $C_2H_5$ | |
| 214 | $n-C_6H_{13}$ | $n-C_3H_7$ | |
| 215 | $n-C_6H_{13}$ | $n-C_4H_9$ | |
| 216 | $n-C_6H_{13}$ | $n-C_5H_{11}$ | |
| 217 | $n-C_6H_{13}$ | $n-C_6H_{13}$ | |
| 218 | $n-C_6H_{13}$ | $n-C_7H_{15}$ | |
| 219 | $n-C_7H_{15}$ | $CH_3$ | |
| 220 | $n-C_7H_{15}$ | $C_2H_5$ | |
| 221 | $n-C_7H_{15}$ | $n-C_3H_7$ | |
| 222 | $n-C_7H_{15}$ | $n-C_4H_9$ | |
| 223 | $n-C_7H_{15}$ | $n-C_5H_{11}$ | |
| 224 | $n-C_7H_{15}$ | $n-C_6H_{13}$ | |
| 225 | $n-C_7H_{15}$ | $n-C_7H_{15}$ | |
| 226 | $CH_3O$ | $CH_3$ | |
| 227 | $CH_3O$ | $C_2H_5$ | |
| 228 | $CH_3O$ | $n-C_3H_7$ | |
| 229 | $CH_3O$ | $n-C_4H_9$ | |
| 230 | $CH_3O$ | $n-C_5H_{11}$ | |
| 231 | $CH_3O$ | $n-C_6H_{13}$ | |
| 232 | $CH_3O$ | $n-C_7H_{15}$ | |
| 233 | $C_2H_5O$ | $CH_3$ | |
| 234 | $C_2H_5O$ | $C_2H_5$ | |
| 235 | $C_2H_5O$ | $n-C_3H_7$ | |

-continued

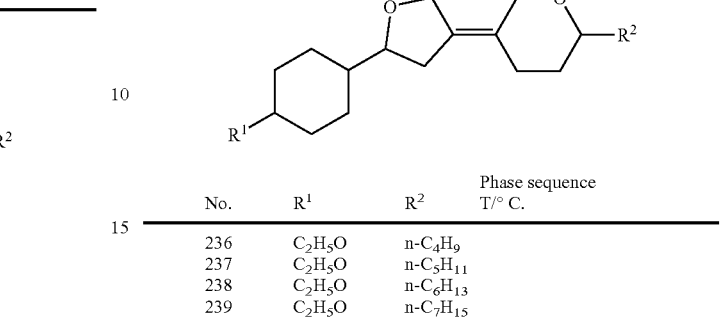

| No. | $R^1$ | $R^2$ | Phase sequence T/° C. |
|---|---|---|---|
| 236 | $C_2H_5O$ | $n-C_4H_9$ | |
| 237 | $C_2H_5O$ | $n-C_5H_{11}$ | |
| 238 | $C_2H_5O$ | $n-C_6H_{13}$ | |
| 239 | $C_2H_5O$ | $n-C_7H_{15}$ | |

Note:
* values extrapolated from 10% solution in ZLI-4792 or ZLI-2857 (Δε).

Examples 240 to 302

The following are prepared analogously to Examples 2 and 4:

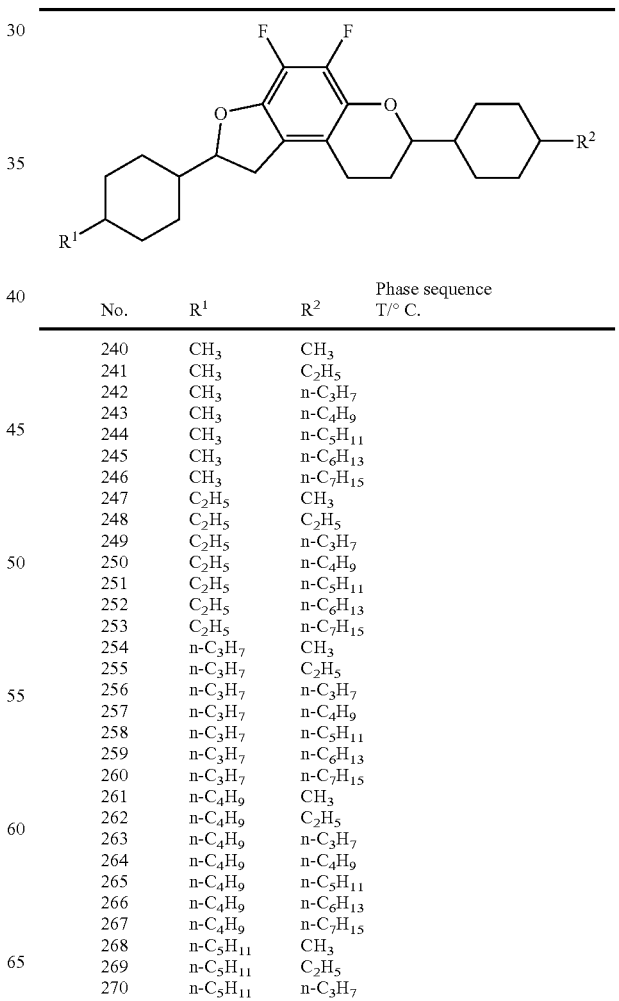

| No. | $R^1$ | $R^2$ | Phase sequence T/° C. |
|---|---|---|---|
| 240 | $CH_3$ | $CH_3$ | |
| 241 | $CH_3$ | $C_2H_5$ | |
| 242 | $CH_3$ | $n-C_3H_7$ | |
| 243 | $CH_3$ | $n-C_4H_9$ | |
| 244 | $CH_3$ | $n-C_5H_{11}$ | |
| 245 | $CH_3$ | $n-C_6H_{13}$ | |
| 246 | $CH_3$ | $n-C_7H_{15}$ | |
| 247 | $C_2H_5$ | $CH_3$ | |
| 248 | $C_2H_5$ | $C_2H_5$ | |
| 249 | $C_2H_5$ | $n-C_3H_7$ | |
| 250 | $C_2H_5$ | $n-C_4H_9$ | |
| 251 | $C_2H_5$ | $n-C_5H_{11}$ | |
| 252 | $C_2H_5$ | $n-C_6H_{13}$ | |
| 253 | $C_2H_5$ | $n-C_7H_{15}$ | |
| 254 | $n-C_3H_7$ | $CH_3$ | |
| 255 | $n-C_3H_7$ | $C_2H_5$ | |
| 256 | $n-C_3H_7$ | $n-C_3H_7$ | |
| 257 | $n-C_3H_7$ | $n-C_4H_9$ | |
| 258 | $n-C_3H_7$ | $n-C_5H_{11}$ | |
| 259 | $n-C_3H_7$ | $n-C_6H_{13}$ | |
| 260 | $n-C_3H_7$ | $n-C_7H_{15}$ | |
| 261 | $n-C_4H_9$ | $CH_3$ | |
| 262 | $n-C_4H_9$ | $C_2H_5$ | |
| 263 | $n-C_4H_9$ | $n-C_3H_7$ | |
| 264 | $n-C_4H_9$ | $n-C_4H_9$ | |
| 265 | $n-C_4H_9$ | $n-C_5H_{11}$ | |
| 266 | $n-C_4H_9$ | $n-C_6H_{13}$ | |
| 267 | $n-C_4H_9$ | $n-C_7H_{15}$ | |
| 268 | $n-C_5H_{11}$ | $CH_3$ | |
| 269 | $n-C_5H_{11}$ | $C_2H_5$ | |
| 270 | $n-C_5H_{11}$ | $n-C_3H_7$ | |

-continued

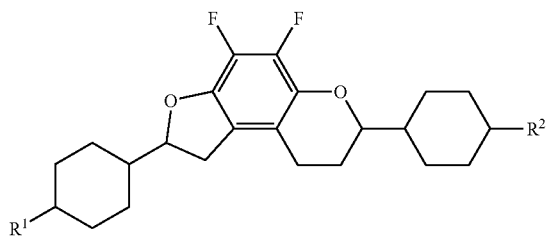

| No. | R¹ | R² | Phase sequence T/° C. |
|---|---|---|---|
| 271 | n-$C_5H_{11}$ | n-$C_4H_9$ | |
| 272 | n-$C_5H_{11}$ | n-$C_5H_{11}$ | |
| 273 | n-$C_5H_{11}$ | n-$C_6H_{13}$ | |
| 274 | n-$C_5H_{11}$ | n-$C_7H_{15}$ | |
| 275 | n-$C_6H_{13}$ | $CH_3$ | |
| 276 | n-$C_6H_{13}$ | $C_2H_5$ | |
| 277 | n-$C_6H_{13}$ | n-$C_3H_7$ | |
| 278 | n-$C_6H_{13}$ | n-$C_4H_9$ | |
| 279 | n-$C_6H_{13}$ | n-$C_5H_{11}$ | |
| 280 | n-$C_6H_{13}$ | n-$C_6H_{13}$ | |
| 281 | n-$C_6H_{13}$ | n-$C_7H_{15}$ | |
| 282 | n-$C_7H_{15}$ | $CH_3$ | |
| 283 | n-$C_7H_{15}$ | $C_2H_5$ | |
| 284 | n-$C_7H_{15}$ | n-$C_3H_7$ | |
| 285 | n-$C_7H_{15}$ | n-$C_4H_9$ | |
| 286 | n-$C_7H_{15}$ | n-$C_5H_{11}$ | |
| 287 | n-$C_7H_{15}$ | n-$C_6H_{13}$ | |
| 288 | n-$C_7H_{15}$ | n-$C_7H_{15}$ | |
| 289 | $CH_3O$ | $CH_3$ | |
| 290 | $CH_3O$ | $C_2H_5$ | |
| 291 | $CH_3O$ | n-$C_3H_7$ | |
| 292 | $CH_3O$ | n-$C_4H_9$ | |
| 293 | $CH_3O$ | n-$C_5H_{11}$ | |
| 294 | $CH_3O$ | n-$C_6H_{13}$ | |
| 295 | $CH_3O$ | n-$C_7H_{15}$ | |
| 296 | $C_2H_5O$ | $CH_3$ | |
| 297 | $C_2H_5O$ | $C_2H_5$ | |
| 298 | $C_2H_5O$ | n-$C_3H_7$ | |
| 299 | $C_2H_5O$ | n-$C_4H_9$ | |
| 300 | $C_2H_5O$ | n-$C_5H_{11}$ | |
| 300 | $C_2H_5O$ | n-$C_6H_{13}$ | |
| 302 | $C_2H_5O$ | n-$C_7H_{15}$ | |

Note:
* values extrapolated from 10% solution in ZLI-4792 or ZLI-2857 (Δε).

Examples 303 to 307

The following are prepared analogously to Examples 5 and 7:

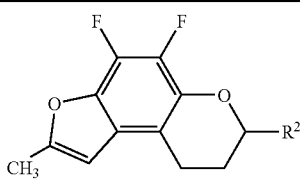

| No. | R² | Phase sequence T/° C. |
|---|---|---|
| 303 | $CH_3$ | |
| 304 | $C_2H_5$ | |
| 5 | n-$C_3H_7$ | C 75 I |
| 305 | n-$C_4H_9$ | |
| 7 | n-$C_5H_{11}$ | C 61 I |
| 306 | n-$C_6H_{13}$ | |
| 307 | n-$C_7H_{15}$ | |

Note:
* values extrapolated from 10% solution in ZLI-4792 or ZLI-2857 (Δε).

Examples 308 to 314

The following are prepared analogously to Examples 5 and 7:

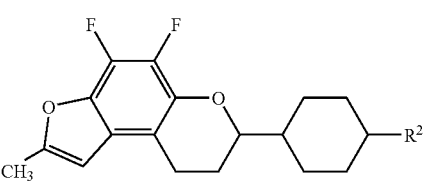

| No. | R² | Phase sequence T/° C. |
|---|---|---|
| 308 | $CH_3$ | |
| 309 | $C_2H_5$ | |
| 310 | n-$C_3H_7$ | |
| 311 | n-$C_4H_9$ | |
| 312 | n-$C_5H_{11}$ | |
| 313 | n-$C_6H_{13}$ | |
| 314 | n-$C_7H_{15}$ | |

Note:
* values extrapolated from 10% solution in ZLI-4792 or ZLI-2857 (Δε).

Examples 315 to 319

The following are prepared analogously to Examples 6 and 8:

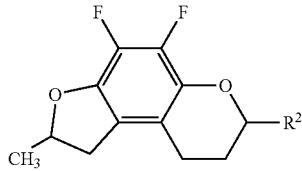

| No. | R² | Phase sequence T/° C. |
|---|---|---|
| 315 | $CH_3$ | |
| 316 | $C_2H_5$ | |
| 6 | n-$C_3H_7$ | C 87 I |
| 317 | n-$C_4H_9$ | |
| 8 | n-$C_5H_{11}$ | C 76 I |
| 318 | n-$C_6H_{13}$ | |
| 319 | n-$C_7H_{15}$ | |

Note:
* values extrapolated from 10% solution in ZLI-4792 or ZLI-2857 (Δε).

Examples 320 to 325

The following are prepared analogously to Examples 6 and 8:

[Structure: difluoro-furan-chroman-cyclohexyl-R² with CH₃ on furan]

| No. | R² | Phase sequence T/° C. |
|---|---|---|
| 320 | CH₃ | |
| 241 | C₂H₅ | |
| 321 | n-C₃H₇ | |
| 322 | n-C₄H₉ | |
| 323 | n-C₅H₁₁ | |
| 324 | n-C₆H₁₃ | |
| 325 | n-C₇H₁₅ | |

Note:
* values extrapolated from 10% solution in ZLI-4792 or ZLI-2857 (Δε).

Examples 326 to 381

The following are prepared analogously to Examples 1, 3 and 9:

[Structure: difluoro-furan-chroman with R¹ and R²]

| No. | R¹ | R² | Phase sequence T/° C. |
|---|---|---|---|
| 326 | C₂H₅ | CH₃ | |
| 327 | C₂H₅ | C₂H₅ | |
| 328 | C₂H₅ | n-C₃H₇ | |
| 329 | C₂H₅ | n-C₄H₉ | |
| 330 | C₂H₅ | n-C₅H₁₁ | |
| 331 | C₂H₅ | n-C₆H₁₃ | |
| 332 | C₂H₅ | n-C₇H₁₅ | |
| 333 | n-C₃H₇ | CH₃ | |
| 334 | n-C₃H₇ | C₂H₅ | |
| 335 | n-C₃H₇ | n-C₃H₇ | |
| 336 | n-C₃H₇ | n-C₄H₉ | |
| 337 | n-C₃H₇ | n-C₅H₁₁ | |
| 338 | n-C₃H₇ | n-C₆H₁₃ | |
| 339 | n-C₃H₇ | n-C₇H₁₅ | |
| 340 | n-C₄H₉ | CH₃ | |
| 341 | n-C₄H₉ | C₂H₅ | |
| 342 | n-C₄H₉ | n-C₃H₇ | |
| 343 | n-C₄H₉ | n-C₄H₉ | |
| 344 | n-C₄H₉ | n-C₅H₁₁ | |
| 345 | n-C₄H₉ | n-C₆H₁₃ | |
| 346 | n-C₄H₉ | n-C₇H₁₅ | |
| 347 | n-C₅H₁₁ | CH₃ | |
| 348 | n-C₅H₁₁ | C₂H₅ | |
| 349 | n-C₅H₁₁ | n-C₃H₇ | |
| 350 | n-C₅H₁₁ | n-C₄H₉ | |
| 351 | n-C₅H₁₁ | n-C₅H₁₁ | |
| 352 | n-C₅H₁₁ | n-C₆H₁₃ | |
| 353 | n-C₅H₁₁ | n-C₇H₁₅ | |
| 354 | n-C₆H₁₃ | CH₃ | |
| 355 | n-C₆H₁₃ | C₂H₅ | |
| 356 | n-C₆H₁₃ | n-C₃H₇ | |
| 357 | n-C₆H₁₃ | n-C₄H₉ | |
| 358 | n-C₆H₁₃ | n-C₅H₁₁ | |
| 359 | n-C₆H₁₃ | n-C₆H₁₃ | |
| 360 | n-C₆H₁₃ | n-C₇H₁₅ | |
| 361 | n-C₇H₁₅ | CH₃ | |
| 362 | n-C₇H₁₅ | C₂H₅ | |
| 363 | n-C₇H₁₅ | n-C₃H₇ | |
| 364 | n-C₇H₁₅ | n-C₄H₉ | |
| 365 | n-C₇H₁₅ | n-C₅H₁₁ | |
| 366 | n-C₇H₁₅ | n-C₆H₁₃ | |
| 367 | n-C₇H₁₅ | n-C₇H₁₅ | |
| 368 | CH₂=CH | CH₃ | |
| 369 | CH₂=CH | C₂H₅ | |
| 370 | CH₂=CH | n-C₃H₇ | |
| 371 | CH₂=CH | n-C₄H₉ | |
| 372 | CH₂=CH | n-C₅H₁₁ | |
| 373 | CH₂=CH | n-C₆H₁₃ | |
| 374 | CH₂=CH | n-C₇H₁₅ | |
| 375 | CH₃—CH=CH | CH₃ | |
| 376 | CH₃—CH=CH | C₂H₅ | |
| 377 | CH₃—CH=CH | n-C₃H₇ | |
| 378 | CH₃—CH=CH | n-C₄H₉ | |
| 379 | CH₃—CH=CH | n-C₅H₁₁ | |
| 380 | CH₃—CH=CH | n-C₆H₁₃ | |
| 381 | CH₃—CH=CH | n-C₇H₁₅ | |

Note:
* values extrapolated from 10% solution in ZLI-4792 or ZLI-2857 (Δε).

Examples 382 to 437

The following are prepared analogously to Examples 1, 3 and 9:

[Structure: difluoro-furan-chroman-cyclohexyl-R² with R¹ on furan]

| No. | R¹ | R² | Phase sequence T/° C. |
|---|---|---|---|
| 382 | C₂H₅ | CH₃ | |
| 383 | C₂H₅ | C₂H₅ | |
| 394 | C₂H₅ | n-C₃H₇ | |
| 395 | C₂H₅ | n-C₄H₉ | |
| 396 | C₂H₅ | n-C₅H₁₁ | |
| 397 | C₂H₅ | n-C₆H₁₃ | |
| 398 | C₂H₅ | n-C₇H₁₅ | |
| 399 | n-C₃H₇ | CH₃ | |
| 390 | n-C₃H₇ | C₂H₅ | |
| 391 | n-C₃H₇ | n-C₃H₇ | |
| 392 | n-C₃H₇ | n-C₄H₉ | |
| 393 | n-C₃H₇ | n-C₅H₁₁ | |
| 394 | n-C₃H₇ | n-C₆H₁₃ | |
| 395 | n-C₃H₇ | n-C₇H₁₅ | |
| 396 | n-C₄H₉ | CH₃ | |

-continued

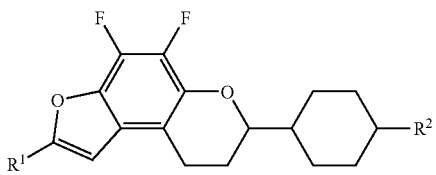

| No. | R¹ | R² | Phase sequence T/° C. |
|---|---|---|---|
| 397 | n-C$_4$H$_9$ | C$_2$H$_5$ | |
| 398 | n-C$_4$H$_9$ | n-C$_3$H$_7$ | |
| 399 | n-C$_4$H$_9$ | n-C$_4$H$_9$ | |
| 400 | n-C$_4$H$_9$ | n-C$_5$H$_{11}$ | |
| 401 | n-C$_4$H$_9$ | n-C$_6$H$_{13}$ | |
| 402 | n-C$_4$H$_9$ | n-C$_7$H$_{15}$ | |
| 403 | n-C$_5$H$_{11}$ | CH$_3$ | |
| 404 | n-C$_5$H$_{11}$ | C$_2$H$_5$ | |
| 405 | n-C$_5$H$_{11}$ | n-C$_3$H$_7$ | |
| 406 | n-C$_5$H$_{11}$ | n-C$_4$H$_9$ | |
| 407 | n-C$_5$H$_{11}$ | n-C$_5$H$_{11}$ | |
| 408 | n-C$_5$H$_{11}$ | n-C$_6$H$_{13}$ | |
| 409 | n-C$_5$H$_{11}$ | n-C$_7$H$_{15}$ | |
| 410 | n-C$_6$H$_{13}$ | CH$_3$ | |
| 411 | n-C$_6$H$_{13}$ | C$_2$H$_5$ | |
| 412 | n-C$_6$H$_{13}$ | n-C$_3$H$_7$ | |
| 413 | n-C$_6$H$_{13}$ | n-C$_4$H$_9$ | |
| 414 | n-C$_6$H$_{13}$ | n-C$_5$H$_{11}$ | |
| 415 | n-C$_6$H$_{13}$ | n-C$_6$H$_{13}$ | |
| 416 | n-C$_6$H$_{13}$ | n-C$_7$H$_{15}$ | |
| 417 | n-C$_7$H$_{15}$ | CH$_3$ | |
| 418 | n-C$_7$H$_{15}$ | C$_2$H$_5$ | |
| 419 | n-C$_7$H$_{15}$ | n-C$_3$H$_7$ | |
| 420 | n-C$_7$H$_{15}$ | n-C$_4$H$_9$ | |
| 421 | n-C$_7$H$_{15}$ | n-C$_5$H$_{11}$ | |
| 422 | n-C$_7$H$_{15}$ | n-C$_6$H$_{13}$ | |
| 423 | n-C$_7$H$_{15}$ | n-C$_7$H$_{15}$ | |
| 424 | CH$_2$=CH | CH$_3$ | |
| 425 | CH$_2$=CH | C$_2$H$_5$ | |
| 426 | CH$_2$=CH | n-C$_3$H$_7$ | |
| 427 | CH$_2$=CH | n-C$_4$H$_9$ | |
| 428 | CH$_2$=CH | n-C$_5$H$_{11}$ | |
| 429 | CH$_2$=CH | n-C$_6$H$_{13}$ | |
| 430 | CH$_2$=CH | n-C$_7$H$_{15}$ | |
| 431 | CH$_3$—CH=CH | CH$_3$ | |
| 432 | CH$_3$—CH=CH | C$_2$H$_5$ | |
| 453 | CH$_3$—CH=CH | n-C$_3$H$_7$ | |
| 434 | CH$_3$—CH=CH | n-C$_4$H$_9$ | |
| 435 | CH$_3$—CH=CH | n-C$_5$H$_{11}$ | |
| 436 | CH$_3$—CH=CH | n-C$_6$H$_{13}$ | |
| 437 | CH$_3$—CH=CH | n-C$_7$H$_{15}$ | |

Note:
* values extrapolated from 10% solution in ZLI-4792 or ZLI-2857 (Δε).

Examples 438 to 480

The following are prepared analogously to Examples 2 and 4:

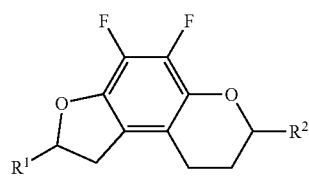

| No. | R¹ | R² | Phase sequence T/° C. |
|---|---|---|---|
| 438 | CH$_3$ | n-C$_7$H$_{15}$ | |
| 439 | C$_2$H$_5$ | CH$_3$ | |
| 440 | C$_2$H$_5$ | C$_2$H$_5$ | |
| 441 | C$_2$H$_5$ | n-C$_3$H$_7$ | |
| 442 | C$_2$H$_5$ | n-C$_4$H$_9$ | |
| 443 | C$_2$H$_5$ | n-C$_5$H$_{11}$ | |
| 444 | C$_2$H$_5$ | n-C$_6$H$_{13}$ | |
| 445 | C$_2$H$_5$ | n-C$_7$H$_{15}$ | |
| 446 | n-C$_3$H$_7$ | CH$_3$ | |
| 447 | n-C$_3$H$_7$ | C$_2$H$_5$ | |
| 448 | n-C$_3$H$_7$ | n-C$_3$H$_7$ | |
| 449 | n-C$_3$H$_7$ | n-C$_4$H$_9$ | |
| 450 | n-C$_3$H$_7$ | n-C$_5$H$_{11}$ | |
| 451 | n-C$_3$H$_7$ | n-C$_6$H$_{13}$ | |
| 452 | n-C$_3$H$_7$ | n-C$_7$H$_{15}$ | |
| 453 | n-C$_4$H$_9$ | CH$_3$ | |
| 454 | n-C$_4$H$_9$ | C$_2$H$_5$ | |
| 455 | n-C$_4$H$_9$ | n-C$_3$H$_7$ | |
| 456 | n-C$_4$H$_9$ | n-C$_4$H$_9$ | |
| 457 | n-C$_4$H$_9$ | n-C$_5$H$_{11}$ | |
| 458 | n-C$_4$H$_9$ | n-C$_6$H$_{13}$ | |
| 459 | n-C$_4$H$_9$ | n-C$_7$H$_{15}$ | |
| 460 | n-C$_5$H$_{11}$ | CH$_3$ | |
| 461 | n-C$_5$H$_{11}$ | C$_2$H$_5$ | |
| 462 | n-C$_5$H$_{11}$ | n-C$_3$H$_7$ | |
| 463 | n-C$_5$H$_{11}$ | n-C$_4$H$_9$ | |
| 464 | n-C$_5$H$_{11}$ | n-C$_5$H$_{11}$ | |
| 465 | n-C$_5$H$_{11}$ | n-C$_6$H$_{13}$ | |
| 466 | n-C$_5$H$_{11}$ | n-C$_7$H$_{15}$ | |
| 467 | n-C$_6$H$_{13}$ | CH$_3$ | |
| 468 | n-C$_6$H$_{13}$ | C$_2$H$_5$ | |
| 469 | n-C$_6$H$_{13}$ | n-C$_3$H$_7$ | |
| 470 | n-C$_6$H$_{13}$ | n-C$_4$H$_9$ | |
| 471 | n-C$_6$H$_{13}$ | n-C$_5$H$_{11}$ | |
| 472 | n-C$_6$H$_{13}$ | n-C$_6$H$_{13}$ | |
| 473 | n-C$_6$H$_{13}$ | n-C$_7$H$_{15}$ | |
| 474 | n-C$_7$H$_{15}$ | CH$_3$ | |
| 475 | n-C$_7$H$_{15}$ | C$_2$H$_5$ | |
| 476 | n-C$_7$H$_{15}$ | n-C$_3$H$_7$ | |
| 477 | n-C$_7$H$_{15}$ | n-C$_4$H$_9$ | |
| 478 | n-C$_7$H$_{15}$ | n-C$_5$H$_{11}$ | |
| 479 | n-C$_7$H$_{15}$ | n-C$_6$H$_{13}$ | |
| 480 | n-C$_7$H$_{15}$ | n-C$_7$H$_{15}$ | |

Note:
* values extrapolated from 10% solution in ZLI-4792 or ZLI-2857 (Δε).

Examples 481 to 523

The following are prepared analogously to Examples 2 and 4:

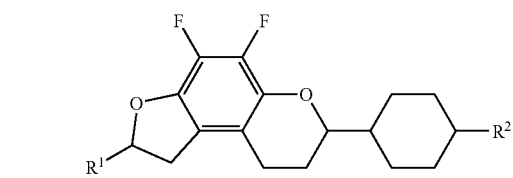

| No. | R¹ | R² | Phase sequence T/° C. |
|---|---|---|---|
| 481 | CH₃ | n-C₇H₁₅ | |
| 482 | C₂H₅ | CH₃ | |
| 483 | C₂H₅ | C₂H₅ | |
| 484 | C₂H₅ | n-C₃H₇ | |
| 485 | C₂H₅ | n-C₄H₉ | |
| 486 | C₂H₅ | n-C₅H₁₁ | |
| 487 | C₂H₅ | n-C₆H₁₃ | |
| 488 | C₂H₅ | n-C₇H₁₅ | |
| 489 | n-C₃H₇ | CH₃ | |
| 490 | n-C₃H₇ | C₂H₅ | |
| 491 | n-C₃H₇ | n-C₃H₇ | |
| 492 | n-C₃H₇ | n-C₄H₉ | |
| 493 | n-C₃H₇ | n-C₅H₁₁ | |
| 494 | n-C₃H₇ | n-C₆H₁₃ | |
| 495 | n-C₃H₇ | n-C₇H₁₅ | |
| 496 | n-C₄H₉ | CH₃ | |
| 497 | n-C₄H₉ | C₂H₅ | |
| 498 | n-C₄H₉ | n-C₃H₇ | |
| 499 | n-C₄H₉ | n-C₄H₉ | |
| 500 | n-C₄H₉ | n-C₅H₁₁ | |
| 501 | n-C₄H₉ | n-C₆H₁₃ | |
| 502 | n-C₄H₉ | n-C₇H₁₅ | |
| 503 | n-C₅H₁₁ | CH₃ | |
| 504 | n-C₅H₁₁ | C₂H₅ | |
| 505 | n-C₅H₁₁ | n-C₃H₇ | |
| 586 | n-C₅H₁₁ | n-C₄H₉ | |
| 507 | n-C₅H₁₁ | n-C₅H₁₁ | |
| 508 | n-C₅H₁₁ | n-C₆H₁₃ | |
| 509 | n-C₅H₁₁ | n-C₇H₁₅ | |
| 510 | n-C₆H₁₃ | CH₃ | |
| 511 | n-C₆H₁₃ | C₂H₅ | |
| 512 | n-C₆H₁₃ | n-C₃H₇ | |
| 513 | n-C₆H₁₃ | n-C₄H₉ | |
| 514 | n-C₆H₁₃ | n-C₅H₁₁ | |
| 515 | n-C₆H₁₃ | n-C₆H₁₃ | |
| 516 | n-C₆H₁₃ | n-C₇H₁₅ | |
| 517 | n-C₇H₁₅ | CH₃ | |
| 518 | n-C₇H₁₅ | C₂H₅ | |
| 519 | n-C₇H₁₅ | n-C₃H₇ | |
| 520 | n-C₇H₁₅ | n-C₄H₉ | |
| 521 | n-C₇H₁₅ | n-C₅H₁₁ | |
| 522 | n-C₇H₁₅ | n-C₆H₁₃ | |
| 523 | n-C₇H₁₅ | n-C₇H₁₅ | |

Note:
* values extrapolated from 10% solution in ZLI-4792 or ZLI-2857 (Δε).

Examples 524 to 599

The following are prepared analogously to Example 9:

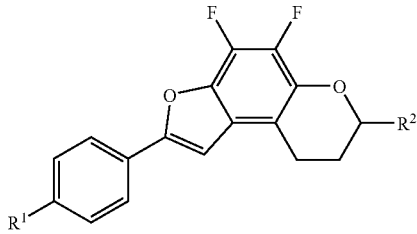

| No. | R¹ | R² | Phase sequence T/° C. |
|---|---|---|---|
| 524 | CH₃ | CH₃ | |
| 525 | CH₃ | C₂H₅ | |
| 526 | CH₃ | n-C₃H₇ | |
| 527 | CH₃ | n-C₄H₉ | |
| 528 | CH₃ | n-C₅H₁₁ | |
| 529 | CH₃ | n-C₆H₁₃ | |
| 530 | CH₃ | n-C₇H₁₅ | |
| 531 | C₂H₅ | CH₃ | |
| 532 | C₂H₅ | C₂H₅ | |
| 533 | C₂H₅ | n-C₃H₇ | |
| 534 | C₂H₅ | n-C₄H₉ | |
| 535 | C₂H₅ | n-C₅H₁₁ | |
| 536 | C₂H₅ | n-C₆H₁₃ | |
| 537 | C₂H₅ | n-C₇H₁₅ | |
| 538 | n-C₃H₇ | CH₃ | |
| 539 | n-C₃H₇ | C₂H₅ | |
| 540 | n-C₃H₇ | n-C₃H₇ | |
| 541 | n-C₃H₇ | n-C₄H₉ | |
| 9 | n-C₃H₇ | n-C₅H₁₁ | T_g −31 C 70 N 79 I |
| 542 | n-C₃H₇ | n-C₆H₁₃ | |
| 543 | n-C₃H₇ | n-C₇H₁₅ | |
| 544 | n-C₄H₉ | CH₃ | |
| 545 | n-C₄H₉ | C₂H₅ | |
| 546 | n-C₄H₉ | n-C₃H₇ | |
| 547 | n-C₄H₉ | n-C₄H₉ | |
| 548 | n-C₄H₉ | n-C₅H₁₁ | |
| 549 | n-C₄H₉ | n-C₆H₁₃ | |
| 550 | n-C₄H₉ | n-C₇H₁₅ | |
| 551 | n-C₅H₁₁ | CH₃ | |
| 552 | n-C₅H₁₁ | C₂H₅ | |
| 553 | n-C₅H₁₁ | n-C₃H₇ | |
| 554 | n-C₅H₁₁ | n-C₄H₉ | |
| 555 | n-C₅H₁₁ | n-C₅H₁₁ | |
| 556 | n-C₅H₁₁ | n-C₆H₁₃ | |
| 557 | n-C₅H₁₁ | n-C₇H₁₅ | |
| 558 | n-C₆H₁₃ | CH₃ | |
| 559 | n-C₆H₁₃ | C₂H₅ | |
| 560 | n-C₆H₁₃ | n-C₃H₇ | |
| 561 | n-C₆H₁₃ | n-C₄H₉ | |
| 562 | n-C₆H₁₃ | n-C₅H₁₁ | |
| 563 | n-C₆H₁₃ | n-C₆H₁₃ | |
| 564 | n-C₆H₁₃ | n-C₇H₁₅ | |
| 565 | n-C₇H₁₅ | CH₃ | |
| 566 | n-C₇H₁₅ | C₂H₅ | |
| 567 | n-C₇H₁₅ | n-C₃H₇ | |
| 568 | n-C₇H₁₅ | n-C₄H₉ | |
| 569 | n-C₇H₁₅ | n-C₅H₁₁ | |
| 570 | n-C₇H₁₅ | n-C₆H₁₃ | |
| 571 | n-C₇H₁₅ | n-C₇H₁₅ | |
| 572 | CH₃O | CH₃ | |
| 573 | CH₃O | C₂H₅ | |
| 574 | CH₃O | n-C₃H₇ | |
| 575 | CH₃O | n-C₄H₉ | |
| 576 | CH₃O | n-C₅H₁₁ | |
| 577 | CH₃O | n-C₆H₁₃ | |
| 578 | CH₃O | n-C₇H₁₅ | |
| 579 | C₂H₅O | CH₃ | |
| 580 | C₂H₅O | C₂H₅ | |
| 581 | C₂H₅O | n-C₃H₇ | |
| 582 | C₂H₅O | n-C₄H₉ | |

-continued

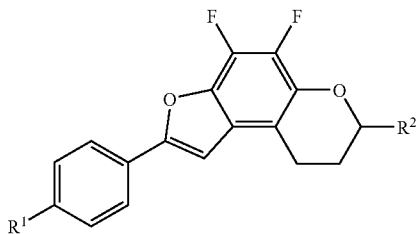

| No. | R¹ | R² | Phase sequence T/° C. |
|---|---|---|---|
| 583 | $C_2H_5O$ | $n-C_5H_{11}$ | |
| 584 | $C_2H_5O$ | $n-C_6H_{13}$ | |
| 599 | $C_2H_5O$ | $n-C_7H_{15}$ | |

Note:
* values extrapolated from 10% solution in ZLI-4792 or ZLI-2857 (Δε).

Examples 600 to 676

The following are prepared analogously to Example 9:

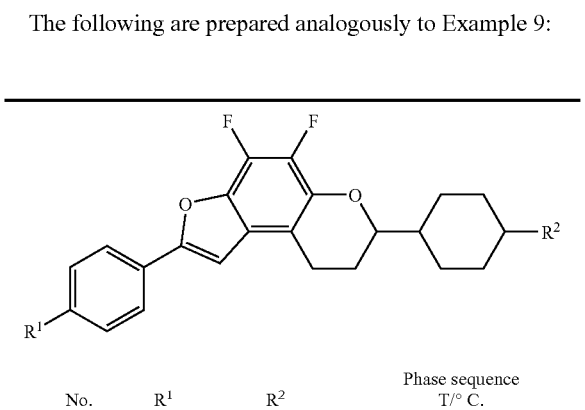

| No. | R¹ | R² | Phase sequence T/° C. |
|---|---|---|---|
| 600 | $CH_3$ | $CH_3$ | |
| 601 | $CH_3$ | $C_2H_5$ | |
| 602 | $CH_3$ | $n-C_3H_7$ | |
| 603 | $CH_3$ | $n-C_4H_9$ | |
| 604 | $CH_3$ | $n-C_5H_{11}$ | |
| 605 | $CH_3$ | $n-C_6H_{13}$ | |
| 606 | $CH_3$ | $n-C_7H_{15}$ | |
| 607 | $C_2H_5$ | $CH_3$ | |
| 608 | $C_2H_5$ | $C_2H_5$ | |
| 609 | $C_2H_5$ | $n-C_3H_7$ | |
| 610 | $C_2H_5$ | $n-C_4H_9$ | |
| 611 | $C_2H_5$ | $n-C_5H_{11}$ | |
| 612 | $C_2H_5$ | $n-C_6H_{13}$ | |
| 613 | $C_2H_5$ | $n-C_7H_{15}$ | |
| 614 | $n-C_3H_7$ | $CH_3$ | |
| 615 | $n-C_3H_7$ | $C_2H_5$ | |
| 616 | $n-C_3H_7$ | $n-C_3H_7$ | |
| 617 | $n-C_3H_7$ | $n-C_4H_9$ | |
| 618 | $n-C_3H_7$ | $n-C_5H_{11}$ | |
| 619 | $n-C_3H_7$ | $n-C_6H_{13}$ | |
| 620 | $n-C_3H_7$ | $n-C_7H_{15}$ | |
| 621 | $n-C_4H_9$ | $CH_3$ | |
| 622 | $n-C_4H_9$ | $C_2H_5$ | |
| 623 | $n-C_4H_9$ | $n-C_3H_7$ | |
| 624 | $n-C_4H_9$ | $n-C_4H_9$ | |
| 625 | $n-C_4H_9$ | $n-C_5H_{11}$ | |
| 626 | $n-C_4H_9$ | $n-C_6H_{13}$ | |
| 627 | $n-C_4H_9$ | $n-C_7H_{15}$ | |
| 628 | $n-C_5H_{11}$ | $CH_3$ | |
| 629 | $n-C_5H_{11}$ | $C_2H_5$ | |
| 630 | $n-C_5H_{11}$ | $n-C_3H_7$ | |
| 631 | $n-C_5H_{11}$ | $n-C_4H_9$ | |
| 632 | $n-C_5H_{11}$ | $n-C_5H_{11}$ | |

-continued

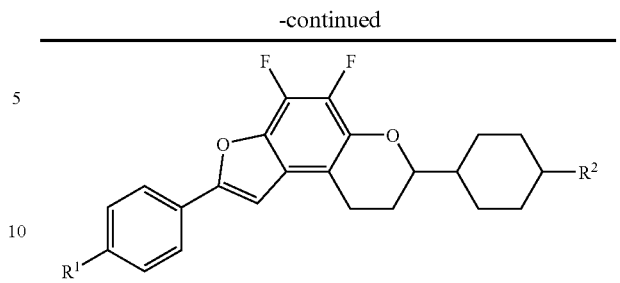

| No. | R¹ | R² | Phase sequence T/° C. |
|---|---|---|---|
| 633 | $n-C_5H_{11}$ | $n-C_6H_{13}$ | |
| 634 | $n-C_5H_{11}$ | $n-C_7H_{15}$ | |
| 635 | $n-C_6H_{13}$ | $CH_3$ | |
| 636 | $n-C_6H_{13}$ | $C_2H_5$ | |
| 637 | $n-C_6H_{13}$ | $n-C_3H_7$ | |
| 638 | $n-C_6H_{13}$ | $n-C_4H_9$ | |
| 639 | $n-C_6H_{13}$ | $n-C_5H_{11}$ | |
| 640 | $n-C_6H_{13}$ | $n-C_6H_{13}$ | |
| 641 | $n-C_6H_{13}$ | $n-C_7H_{15}$ | |
| 642 | $n-C_7H_{15}$ | $CH_3$ | |
| 643 | $n-C_7H_{15}$ | $C_2H_5$ | |
| 644 | $n-C_7H_{15}$ | $n-C_3H_7$ | |
| 645 | $n-C_7H_{15}$ | $n-C_4H_9$ | |
| 646 | $n-C_7H_{15}$ | $n-C_5H_{11}$ | |
| 677 | $n-C_7H_{15}$ | $n-C_6H_{13}$ | |
| 648 | $n-C_7H_{15}$ | $n-C_7H_{15}$ | |
| 649 | $CH_3O$ | $CH_3$ | |
| 650 | $CH_3O$ | $C_2H_5$ | |
| 651 | $CH_3O$ | $n-C_3H_7$ | |
| 652 | $CH_3O$ | $n-C_4H_9$ | |
| 653 | $CH_3O$ | $n-C_5H_{11}$ | |
| 654 | $CH_3O$ | $n-C_6H_{13}$ | |
| 669 | $CH_3O$ | $n-C_7H_{15}$ | |
| 670 | $C_2H_5O$ | $CH_3$ | |
| 671 | $C_2H_5O$ | $C_2H_5$ | |
| 672 | $C_2H_5O$ | $n-C_3H_7$ | |
| 673 | $C_2H_5O$ | $n-C_4H_9$ | |
| 674 | $C_2H_5O$ | $n-C_5H_{11}$ | |
| 675 | $C_2H_5O$ | $n-C_6H_{13}$ | |
| 676 | $C_2H_5O$ | $n-C_7H_{15}$ | |

Note:
* values extrapolated from 10% solution in ZLI-4792 or ZLI-2857 (Δε).

Examples 677 to 753

The following are prepared from 31 analogously to Examples 1, 3 and 9:

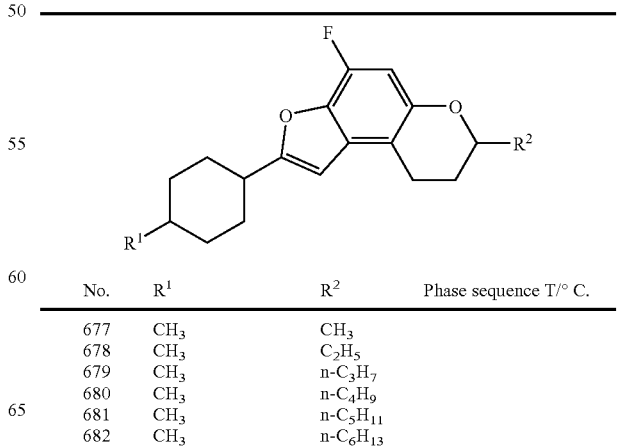

| No. | R¹ | R² | Phase sequence T/° C. |
|---|---|---|---|
| 677 | $CH_3$ | $CH_3$ | |
| 678 | $CH_3$ | $C_2H_5$ | |
| 679 | $CH_3$ | $n-C_3H_7$ | |
| 680 | $CH_3$ | $n-C_4H_9$ | |
| 681 | $CH_3$ | $n-C_5H_{11}$ | |
| 682 | $CH_3$ | $n-C_6H_{13}$ | |

-continued

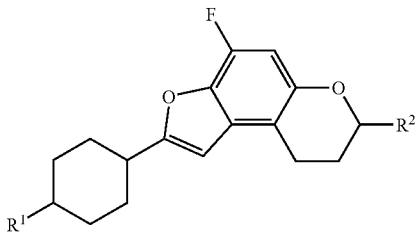

| No. | R¹ | R² | Phase sequence T/° C. |
|---|---|---|---|
| 683 | CH₃ | n-C₇H₁₅ | |
| 684 | C₂H₅ | CH₃ | |
| 685 | C₂H₅ | C₂H₅ | |
| 686 | C₂H₅ | n-C₃H₇ | |
| 687 | C₂H₅ | n-C₄H₉ | |
| 688 | C₂H₅ | n-C₅H₁₁ | |
| 689 | C₂H₅ | n-C₆H₁₃ | |
| 690 | C₂H₅ | n-C₇H₁₅ | |
| 691 | n-C₃H₇ | CH₃ | |
| 692 | n-C₃H₇ | C₂H₅ | |
| 693 | n-C₃H₇ | n-C₃H₇ | |
| 694 | n-C₃H₇ | n-C₄H₉ | |
| 695 | n-C₃H₇ | n-C₅H₁₁ | |
| 696 | n-C₃H₇ | n-C₆H₁₃ | |
| 697 | n-C₃H₇ | n-C₇H₁₅ | |
| 698 | n-C₄H₉ | CH₃ | |
| 699 | n-C₄H₉ | C₂H₅ | |
| 700 | n-C₄H₉ | n-C₃H₇ | |
| 701 | n-C₄H₉ | n-C₄H₉ | |
| 702 | n-C₄H₉ | n-C₅H₁₁ | |
| 703 | n-C₄H₉ | n-C₆H₁₃ | |
| 704 | n-C₄H₉ | n-C₇H₁₅ | |
| 705 | n-C₅H₁₁ | CH₃ | |
| 706 | n-C₅H₁₁ | C₂H₅ | |
| 707 | n-C₅H₁₁ | n-C₃H₇ | |
| 708 | n-C₅H₁₁ | n-C₄H₉ | |
| 709 | n-C₅H₁₁ | n-C₅H₁₁ | |
| 710 | n-C₅H₁₁ | n-C₆H₁₃ | |
| 711 | n-C₅H₁₁ | n-C₇H₁₅ | |
| 712 | n-C₆H₁₃ | CH₃ | |
| 713 | n-C₆H₁₃ | C₂H₅ | |
| 714 | n-C₆H₁₃ | n-C₃H₇ | |
| 715 | n-C₆H₁₃ | n-C₄H₉ | |
| 716 | n-C₆H₁₃ | n-C₅H₁₁ | |
| 717 | n-C₆H₁₃ | n-C₆H₁₃ | |
| 718 | n-C₆H₁₃ | n-C₇H₁₅ | |
| 719 | n-C₇H₁₅ | CH₃ | |
| 720 | n-C₇H₁₅ | C₂H₅ | |
| 721 | n-C₇H₁₅ | n-C₃H₇ | |
| 722 | n-C₇H₁₅ | n-C₄H₉ | |
| 723 | n-C₇H₁₅ | n-C₅H₁₁ | |
| 724 | n-C₇H₁₅ | n-C₆H₁₃ | |
| 725 | n-C₇H₁₅ | n-C₇H₁₅ | |
| 726 | CH₃O | CH₃ | |
| 727 | CH₃O | C₂H₅ | |
| 728 | CH₃O | n-C₃H₇ | |
| 729 | CH₃O | n-C₄H₉ | |
| 730 | CH₃O | n-C₅H₁₁ | |
| 731 | CH₃O | n-C₆H₁₃ | |
| 732 | CH₃O | n-C₇H₁₅ | |
| 733 | C₂H₅O | CH₃ | |
| 734 | C₂H₅O | C₂H₅ | |
| 735 | C₂H₅O | n-C₃H₇ | |
| 736 | C₂H₅O | n-C₄H₉ | |
| 737 | C₂H₅O | n-C₅H₁₁ | |
| 738 | C₂H₅O | n-C₆H₁₃ | |
| 739 | C₂H₅O | n-C₇H₁₅ | |
| 740 | CH₂=CH | CH₃ | |
| 741 | CH₂=CH | C₂H₅ | |
| 742 | CH₂=CH | n-C₃H₇ | |
| 743 | CH₂=CH | n-C₄H₉ | |
| 744 | CH₂=CH | n-C₅H₁₁ | |
| 745 | CH₂=CH | n-C₆H₁₃ | |
| 746 | CH₂=CH | n-C₇H₁₅ | |
| 747 | CH₃—CH=CH | CH₃ | |

-continued

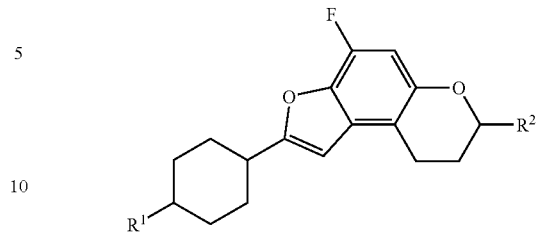

| No. | R¹ | R² | Phase sequence T/° C. |
|---|---|---|---|
| 748 | CH₃—CH=CH | C₂H₅ | |
| 749 | CH₃—CH=CH | n-C₃H₇ | |
| 750 | CH₃—CH=CH | n-C₄H₉ | |
| 751 | CH₃—CH=CH | n-C₅H₁₁ | |
| 752 | CH₃—CH=CH | n-C₆H₁₃ | |
| 753 | CH₃—CH=CH | n-C₇H₁₅ | |

Note:
* values extrapolated from 10% solution in ZLI-4792 or ZLI-2857 (Δε).

Examples 754 to 821

The following are prepared from 36 analogously to Examples 1, 3 and 9:

| No. | R¹ | R² | Phase sequence T/° C. |
|---|---|---|---|
| 754 | CH₃ | CH₃ | |
| 755 | CH₃ | C₂H₅ | |
| 756 | CH₃ | n-C₃H₇ | |
| 757 | CH₃ | n-C₄H₉ | |
| 758 | CH₃ | n-C₅H₁₁ | |
| 759 | CH₃ | n-C₆H₁₃ | |
| 760 | CH₃ | n-C₇H₁₅ | |
| 761 | C₂H₅ | CH₃ | |
| 762 | C₂H₅ | C₂H₅ | |
| 763 | C₂H₅ | n-C₃H₇ | |
| 764 | C₂H₅ | n-C₄H₉ | |
| 765 | C₂H₅ | n-C₅H₁₁ | |
| 766 | C₂H₅ | n-C₆H₁₃ | |
| 767 | C₂H₅ | n-C₇H₁₅ | |
| 768 | n-C₃H₇ | CH₃ | |
| 769 | n-C₃H₇ | C₂H₅ | |
| 770 | n-C₃H₇ | n-C₃H₇ | |
| 771 | n-C₃H₇ | n-C₄H₉ | |
| 772 | n-C₃H₇ | n-C₅H₁₁ | |
| 773 | n-C₃H₇ | n-C₆H₁₃ | |
| 774 | n-C₃H₇ | n-C₇H₁₅ | |
| 775 | n-C₄H₉ | CH₃ | |
| 776 | n-C₄H₉ | C₂H₅ | |
| 777 | n-C₄H₉ | n-C₃H₇ | |
| 778 | n-C₄H₉ | n-C₄H₉ | |
| 779 | n-C₄H₉ | n-C₅H₁₁ | |
| 780 | n-C₄H₉ | n-C₆H₁₃ | |
| 781 | n-C₄H₉ | n-C₇H₁₅ | |
| 782 | n-C₅H₁₁ | CH₃ | |
| 783 | n-C₅H₁₁ | C₂H₅ | |
| 784 | n-C₅H₁₁ | n-C₃H₇ | |

-continued

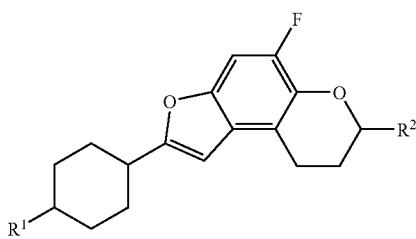

| No. | $R^1$ | $R^2$ | Phase sequence T/° C. |
|---|---|---|---|
| 785 | n-$C_5H_{11}$ | n-$C_4H_9$ | |
| 786 | n-$C_5H_{11}$ | n-$C_5H_{11}$ | |
| 787 | n-$C_5H_{11}$ | n-$C_6H_{13}$ | |
| 788 | n-$C_5H_{11}$ | n-$C_7H_{15}$ | |
| 789 | n-$C_6H_{13}$ | $CH_3$ | |
| 790 | n-$C_6H_{13}$ | $C_2H_5$ | |
| 791 | n-$C_6H_{13}$ | n-$C_3H_7$ | |
| 792 | n-$C_6H_{13}$ | n-$C_4H_9$ | |
| 793 | n-$C_6H_{13}$ | n-$C_5H_{11}$ | |
| 794 | n-$C_6H_{13}$ | n-$C_6H_{13}$ | |
| 795 | n-$C_6H_{13}$ | n-$C_7H_{15}$ | |
| 796 | n-$C_7H_{15}$ | $CH_3$ | |
| 797 | n-$C_7H_{15}$ | $C_2H_5$ | |
| 798 | n-$C_7H_{15}$ | n-$C_3H_7$ | |
| 799 | n-$C_7H_{15}$ | n-$C_4H_9$ | |
| 800 | n-$C_7H_{15}$ | n-$C_5H_{11}$ | |
| 801 | n-$C_7H_{15}$ | n-$C_6H_{13}$ | |
| 802 | n-$C_7H_{15}$ | n-$C_7H_{15}$ | |
| 803 | $CH_3O$ | $CH_3$ | |
| 804 | $CH_3O$ | $C_2H_5$ | |
| 806 | $CH_3O$ | n-$C_3H_7$ | |
| 807 | $CH_3O$ | n-$C_4H_9$ | |
| 808 | $CH_3O$ | n-$C_5H_{11}$ | |
| 809 | $CH_3O$ | n-$C_6H_{13}$ | |
| 810 | $CH_3O$ | n-$C_7H_{15}$ | |
| 811 | $C_2H_5O$ | $CH_3$ | |
| 812 | $C_2H_5O$ | $C_2H_5$ | |
| 813 | $C_2H_5O$ | n-$C_3H_7$ | |
| 814 | $C_2H_5O$ | n-$C_4H_9$ | |
| 815 | $C_2H_5O$ | n-$C_5H_{11}$ | |
| 816 | $C_2H_5O$ | n-$C_6H_{13}$ | |
| 817 | $C_2H_5O$ | n-$C_7H_{15}$ | |
| 818 | $CH_2$=CH | $CH_3$ | |
| 819 | $CH_2$=CH | $C_2H_5$ | |
| 820 | $CH_2$=CH | n-$C_3H_7$ | |
| 821 | $CH_2$=CH | n-$C_4H_9$ | |
| 822 | $CH_2$=CH | n-$C_5H_{11}$ | |
| 823 | $CH_2$=CH | n-$C_6H_{13}$ | |
| 824 | $CH_2$=CH | n-$C_7H_{15}$ | |
| 825 | $CH_3$—CH=CH | $CH_3$ | |
| 826 | $CH_3$—CH=CH | $C_2H_5$ | |
| 827 | $CH_3$—CH=CH | n-$C_3H_7$ | |
| 828 | $CH_3$—CH=CH | n-$C_4H_9$ | |
| 829 | $CH_3$—CH=CH | n-$C_5H_{11}$ | |
| 820 | $CH_3$—CH=CH | n-$C_6H_{13}$ | |
| 821 | $CH_3$—CH=CH | n-$C_7H_{15}$ | |

Note:
* values extrapolated from 10% solution in ZLI-4792 or ZLI-2857 (Δε).

Examples 822 to 877

The following are prepared from 31 analogously to Examples 1, 3 and 9:

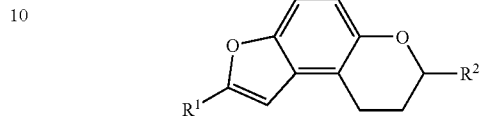

| No. | $R^1$ | $R^2$ | Phase sequence T/° C. |
|---|---|---|---|
| 822 | $C_2H_5$ | $CH_3$ | |
| 823 | $C_2H_5$ | $C_2H_5$ | |
| 824 | $C_2H_5$ | n-$C_3H_7$ | |
| 825 | $C_2H_5$ | n-$C_4H_9$ | |
| 826 | $C_2H_5$ | n-$C_5H_{11}$ | |
| 827 | $C_2H_5$ | n-$C_6H_{13}$ | |
| 828 | $C_2H_5$ | n-$C_7H_{15}$ | |
| 829 | n-$C_3H_7$ | $CH_3$ | |
| 830 | n-$C_3H_7$ | $C_2H_5$ | |
| 831 | n-$C_3H_7$ | n-$C_3H_7$ | |
| 832 | n-$C_3H_7$ | n-$C_4H_9$ | |
| 833 | n-$C_3H_7$ | n-$C_5H_{11}$ | |
| 834 | n-$C_3H_7$ | n-$C_6H_{13}$ | |
| 835 | n-$C_3H_7$ | n-$C_7H_{15}$ | |
| 836 | n-$C_4H_9$ | $CH_3$ | |
| 837 | n-$C_4H_9$ | $C_2H_5$ | |
| 838 | n-$C_4H_9$ | n-$C_3H_7$ | |
| 839 | n-$C_4H_9$ | n-$C_4H_9$ | |
| 840 | n-$C_4H_9$ | n-$C_5H_{11}$ | |
| 841 | n-$C_4H_9$ | n-$C_6H_{13}$ | |
| 842 | n-$C_4H_9$ | n-$C_7H_{15}$ | |
| 843 | n-$C_5H_{11}$ | $CH_3$ | |
| 844 | n-$C_5H_{11}$ | $C_2H_5$ | |
| 845 | n-$C_5H_{11}$ | n-$C_3H_7$ | |
| 846 | n-$C_5H_{11}$ | n-$C_4H_9$ | |
| 847 | n-$C_5H_{11}$ | n-$C_5H_{11}$ | |
| 848 | n-$C_5H_{11}$ | n-$C_6H_{13}$ | |
| 849 | n-$C_5H_{11}$ | n-$C_7H_{15}$ | |
| 850 | n-$C_6H_{13}$ | $CH_3$ | |
| 851 | n-$C_6H_{13}$ | $C_2H_5$ | |
| 852 | n-$C_6H_{13}$ | n-$C_3H_7$ | |
| 853 | n-$C_6H_{13}$ | n-$C_4H_9$ | |
| 854 | n-$C_6H_{13}$ | n-$C_5H_{11}$ | |
| 855 | n-$C_6H_{13}$ | n-$C_6H_{13}$ | |
| 856 | n-$C_6H_{13}$ | n-$C_7H_{15}$ | |
| 857 | n-$C_7H_{15}$ | $CH_3$ | |
| 858 | n-$C_7H_{15}$ | $C_2H_5$ | |
| 859 | n-$C_7H_{15}$ | n-$C_3H_7$ | |
| 860 | n-$C_7H_{15}$ | n-$C_4H_9$ | |
| 861 | n-$C_7H_{15}$ | n-$C_5H_{11}$ | |
| 862 | n-$C_7H_{15}$ | n-$C_6H_{13}$ | |
| 863 | n-$C_7H_{15}$ | n-$C_7H_{15}$ | |
| 864 | $CH_2$=CH | $CH_3$ | |
| 865 | $CH_2$=CH | $C_2H_5$ | |
| 866 | $CH_2$=CH | n-$C_3H_7$ | |
| 867 | $CH_2$=CH | n-$C_4H_9$ | |
| 868 | $CH_2$=CH | n-$C_5H_{11}$ | |
| 869 | $CH_2$=CH | n-$C_6H_{13}$ | |
| 870 | $CH_2$=CH | n-$C_7H_{15}$ | |
| 871 | $CH_3$—CH=CH | $CH_3$ | |
| 872 | $CH_3$—CH=CH | $C_2H_5$ | |
| 873 | $CH_3$—CH=CH | n-$C_3H_7$ | |
| 874 | $CH_3$—CH=CH | n-$C_4H_9$ | |
| 875 | $CH_3$—CH=CH | n-$C_5H_{11}$ | |
| 876 | $CH_3$—CH=CH | n-$C_6H_{13}$ | |
| 877 | $CH_3$—CH=CH | n-$C_7H_{15}$ | |

Note:
* values extrapolated from 10% solution in ZLI-4792 or ZLI-2857 (Δε).

Examples 878 to 940

The following are prepared from 36 analogously to Examples 1, 3 and 9:

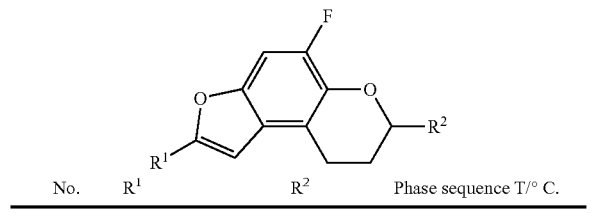

| No. | $R^1$ | $R^2$ | Phase sequence T/° C. |
|---|---|---|---|
| 878 | $CH_3$ | $CH_3$ | |
| 879 | $CH_3$ | $C_2H_5$ | |
| 880 | $CH_3$ | $n-C_3H_7$ | |
| 881 | $CH_3$ | $n-C_4H_9$ | |
| 882 | $CH_3$ | $n-C_5H_{11}$ | |
| 883 | $CH_3$ | $n-C_6H_{13}$ | |
| 884 | $CH_3$ | $n-C_7H_{15}$ | |
| 885 | $C_2H_5$ | $CH_3$ | |
| 886 | $C_2H_5$ | $C_2H_5$ | |
| 887 | $C_2H_5$ | $n-C_3H_7$ | |
| 888 | $C_2H_5$ | $n-C_4H_9$ | |
| 889 | $C_2H_5$ | $n-C_5H_{11}$ | |
| 890 | $C_2H_5$ | $n-C_6H_{13}$ | |
| 891 | $C_2H_5$ | $n-C_7H_{15}$ | |
| 892 | $n-C_3H_7$ | $CH_3$ | |
| 893 | $n-C_3H_7$ | $C_2H_5$ | |
| 894 | $n-C_3H_7$ | $n-C_3H_7$ | |
| 895 | $n-C_3H_7$ | $n-C_4H_9$ | |
| 896 | $n-C_3H_7$ | $n-C_5H_{11}$ | |
| 897 | $n-C_3H_7$ | $n-C_6H_{13}$ | |
| 898 | $n-C_3H_7$ | $n-C_7H_{15}$ | |
| 899 | $n-C_4H_9$ | $CH_3$ | |
| 900 | $n-C_4H_9$ | $C_2H_5$ | |
| 901 | $n-C_4H_9$ | $n-C_3H_7$ | |
| 902 | $n-C_4H_9$ | $n-C_4H_9$ | |
| 903 | $n-C_4H_9$ | $n-C_5H_{11}$ | |
| 904 | $n-C_4H_9$ | $n-C_6H_{13}$ | |
| 905 | $n-C_4H_9$ | $n-C_7H_{15}$ | |
| 906 | $n-C_5H_{11}$ | $CH_3$ | |
| 907 | $n-C_5H_{11}$ | $C_2H_5$ | |
| 908 | $n-C_5H_{11}$ | $n-C_3H_7$ | |
| 909 | $n-C_5H_{11}$ | $n-C_4H_9$ | |
| 910 | $n-C_5H_{11}$ | $n-C_5H_{11}$ | |
| 911 | $n-C_5H_{11}$ | $n-C_6H_{13}$ | |
| 912 | $n-C_5H_{11}$ | $n-C_7H_{15}$ | |
| 913 | $n-C_6H_{13}$ | $CH_3$ | |
| 914 | $n-C_6H_{13}$ | $C_2H_5$ | |
| 915 | $n-C_6H_{13}$ | $n-C_3H_7$ | |
| 916 | $n-C_6H_{13}$ | $n-C_4H_9$ | |
| 917 | $n-C_6H_{13}$ | $n-C_5H_{11}$ | |
| 918 | $n-C_6H_{13}$ | $n-C_6H_{13}$ | |
| 919 | $n-C_6H_{13}$ | $n-C_7H_{15}$ | |
| 920 | $n-C_7H_{15}$ | $CH_3$ | |
| 921 | $n-C_7H_{15}$ | $C_2H_5$ | |
| 922 | $n-C_7H_{15}$ | $n-C_3H_7$ | |
| 923 | $n-C_7H_{15}$ | $n-C_4H_9$ | |
| 924 | $n-C_7H_{15}$ | $n-C_5H_{11}$ | |
| 925 | $n-C_7H_{15}$ | $n-C_6H_{13}$ | |
| 926 | $n-C_7H_{15}$ | $n-C_7H_{15}$ | |
| 927 | $CH_2=CH$ | $CH_3$ | |
| 928 | $CH_2=CH$ | $C_2H_5$ | |
| 929 | $CH_2=CH$ | $n-C_3H_7$ | |
| 930 | $CH_2=CH$ | $n-C_4H_9$ | |
| 931 | $CH_2=CH$ | $n-C_5H_{11}$ | |
| 932 | $CH_2=CH$ | $n-C_6H_{13}$ | |
| 933 | $CH_2=CH$ | $n-C_7H_{15}$ | |
| 934 | $CH_3-CH=CH$ | $CH_3$ | |
| 935 | $CH_3-CH=CH$ | $C_2H_5$ | |
| 936 | $CH_3-CH=CH$ | $n-C_3H_7$ | |
| 937 | $CH_3-CH=CH$ | $n-C_4H_9$ | |
| 938 | $CH_3-CH=CH$ | $n-C_5H_{11}$ | |
| 939 | $CH_3-CH=CH$ | $n-C_6H_{13}$ | |
| 940 | $CH_3-CH=CH$ | $n-C_7H_{15}$ | |

Note:
* values extrapolated from 10% solution in ZLI-4792 or ZLI-2857 ($\Delta\epsilon$).

Examples 941 to 996

The following are prepared from 31 analogously to Examples 1, 3 and 9:

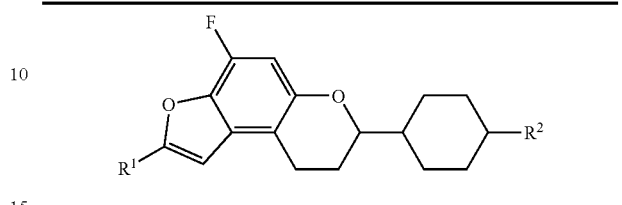

| No. | $R^1$ | $R^2$ | Phase sequence T/° C. |
|---|---|---|---|
| 941 | $C_2H_5$ | $CH_3$ | |
| 942 | $C_2H_5$ | $C_2H_5$ | |
| 943 | $C_2H_5$ | $n-C_3H_7$ | |
| 944 | $C_2H_5$ | $n-C_4H_9$ | |
| 945 | $C_2H_5$ | $n-C_5H_{11}$ | |
| 946 | $C_2H_5$ | $n-C_6H_{13}$ | |
| 947 | $C_2H_5$ | $n-C_7H_{15}$ | |
| 948 | $n-C_3H_7$ | $CH_3$ | |
| 949 | $n-C_3H_7$ | $C_2H_5$ | |
| 950 | $n-C_3H_7$ | $n-C_3H_7$ | |
| 951 | $n-C_3H_7$ | $n-C_4H_9$ | |
| 952 | $n-C_3H_7$ | $n-C_5H_{11}$ | |
| 953 | $n-C_3H_7$ | $n-C_6H_{13}$ | |
| 954 | $n-C_3H_7$ | $n-C_7H_{15}$ | |
| 955 | $n-C_4H_9$ | $CH_3$ | |
| 956 | $n-C_4H_9$ | $C_2H_5$ | |
| 957 | $n-C_4H_9$ | $n-C_3H_7$ | |
| 958 | $n-C_4H_9$ | $n-C_4H_9$ | |
| 959 | $n-C_4H_9$ | $n-C_5H_{11}$ | |
| 960 | $n-C_4H_9$ | $n-C_6H_{13}$ | |
| 961 | $n-C_4H_9$ | $n-C_7H_{15}$ | |
| 962 | $n-C_5H_{11}$ | $CH_3$ | |
| 963 | $n-C_5H_{11}$ | $C_2H_5$ | |
| 964 | $n-C_5H_{11}$ | $n-C_3H_7$ | |
| 965 | $n-C_5H_{11}$ | $n-C_4H_9$ | |
| 966 | $n-C_5H_{11}$ | $n-C_5H_{11}$ | |
| 967 | $n-C_5H_{11}$ | $n-C_6H_{13}$ | |
| 968 | $n-C_5H_{11}$ | $n-C_7H_{15}$ | |
| 969 | $n-C_6H_{13}$ | $CH_3$ | |
| 970 | $n-C_6H_{13}$ | $C_2H_5$ | |
| 971 | $n-C_6H_{13}$ | $n-C_3H_7$ | |
| 972 | $n-C_6H_{13}$ | $n-C_4H_9$ | |
| 973 | $n-C_6H_{13}$ | $n-C_5H_{11}$ | |
| 974 | $n-C_6H_{13}$ | $n-C_6H_{13}$ | |
| 975 | $n-C_6H_{13}$ | $n-C_7H_{15}$ | |
| 976 | $n-C_7H_{15}$ | $CH_3$ | |
| 977 | $n-C_7H_{15}$ | $C_2H_5$ | |
| 978 | $n-C_7H_{15}$ | $n-C_3H_7$ | |
| 979 | $n-C_7H_{15}$ | $n-C_4H_9$ | |
| 980 | $n-C_7H_{15}$ | $n-C_5H_{11}$ | |
| 981 | $n-C_7H_{15}$ | $n-C_6H_{13}$ | |
| 982 | $n-C_7H_{15}$ | $n-C_7H_{15}$ | |
| 983 | $CH_2=CH$ | $CH_3$ | |
| 984 | $CH_2=CH$ | $C_2H_5$ | |
| 985 | $CH_2=CH$ | $n-C_3H_7$ | |
| 986 | $CH_2=CH$ | $n-C_4H_9$ | |
| 987 | $CH_2=CH$ | $n-C_5H_{11}$ | |
| 988 | $CH_2=CH$ | $n-C_6H_{13}$ | |
| 989 | $CH_2=CH$ | $n-C_7H_{15}$ | |
| 990 | $CH_3-CH=CH$ | $CH_3$ | |
| 991 | $CH_3-CH=CH$ | $C_2H_5$ | |
| 992 | $CH_3-CH=CH$ | $n-C_3H_7$ | |
| 993 | $CH_3-CH=CH$ | $n-C_4H_9$ | |
| 994 | $CH_3-CH=CH$ | $n-C_5H_{11}$ | |
| 995 | $CH_3-CH=CH$ | $n-C_6H_{13}$ | |
| 996 | $CH_3-CH=CH$ | $n-C_7H_{15}$ | |

Note:
* values extrapolated from 10% solution in ZLI-4792 or ZLI-2857 ($\Delta\epsilon$).

Examples 997 to 1059

The following are prepared from 36 analogously to Examples 1, 3 and 9:

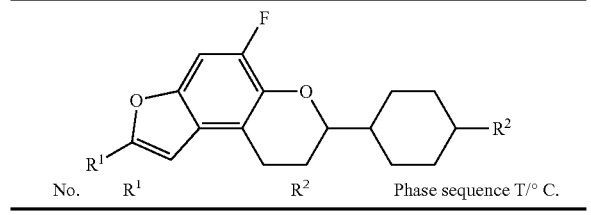

| No. | R¹ | R² | Phase sequence T/° C. |
|---|---|---|---|
| 997 | CH$_3$ | CH$_3$ | |
| 998 | CH$_3$ | C$_2$H$_5$ | |
| 999 | CH$_3$ | n-C$_3$H$_7$ | |
| 1000 | CH$_3$ | n-C$_4$H$_9$ | |
| 1001 | CH$_3$ | n-C$_5$H$_{11}$ | |
| 1002 | CH$_3$ | n-C$_6$H$_{13}$ | |
| 1003 | CH$_3$ | n-C$_7$H$_{15}$ | |
| 1004 | C$_2$H$_5$ | CH$_3$ | |
| 1005 | C$_2$H$_5$ | C$_2$H$_5$ | |
| 1006 | C$_2$H$_5$ | n-C$_3$H$_7$ | |
| 1007 | C$_2$H$_5$ | n-C$_9$H$_9$ | |
| 1008 | C$_2$H$_5$ | n-C$_5$H$_{11}$ | |
| 1009 | C$_2$H$_5$ | n-C$_6$H$_{13}$ | |
| 1010 | C$_2$H$_5$ | n-C$_7$H$_{15}$ | |
| 1011 | n-C$_3$H$_7$ | CH$_3$ | |
| 1012 | n-C$_3$H$_7$ | C$_2$H$_5$ | |
| 1013 | n-C$_3$H$_7$ | n-C$_3$H$_7$ | |
| 1014 | n-C$_3$H$_7$ | n-C$_4$H$_9$ | |
| 1015 | n-C$_3$H$_7$ | n-C$_5$H$_{11}$ | |
| 1016 | n-C$_3$H$_7$ | n-C$_6$H$_{13}$ | |
| 1017 | n-C$_3$H$_7$ | n-C$_7$H$_{15}$ | |
| 1018 | n-C$_4$H$_9$ | CH$_3$ | |
| 1019 | n-C$_4$H$_9$ | C$_2$H$_5$ | |
| 1020 | n-C$_4$H$_9$ | n-C$_3$H$_7$ | |
| 1021 | n-C$_4$H$_9$ | n-C$_4$H$_9$ | |
| 1022 | n-C$_4$H$_9$ | n-C$_5$H$_{11}$ | |
| 1023 | n-C$_4$H$_9$ | n-C$_6$H$_{13}$ | |
| 1024 | n-C$_4$H$_9$ | n-C$_7$H$_{15}$ | |
| 1025 | n-C$_5$H$_{11}$ | CH$_3$ | |
| 1026 | n-C$_5$H$_{11}$ | C$_2$H$_5$ | |
| 1027 | n-C$_5$H$_{11}$ | n-C$_3$H$_7$ | |
| 1028 | n-C$_5$H$_{11}$ | n-C$_4$H$_9$ | |
| 1029 | n-C$_5$H$_{11}$ | n-C$_5$H$_{11}$ | |
| 1030 | n-C$_5$H$_{11}$ | n-C$_6$H$_{13}$ | |
| 1031 | n-C$_5$H$_{11}$ | n-C$_7$H$_{15}$ | |
| 1032 | n-C$_6$H$_{13}$ | CH$_3$ | |
| 1033 | n-C$_6$H$_{13}$ | C$_2$H$_5$ | |
| 1034 | n-C$_6$H$_{13}$ | n-C$_3$H$_7$ | |
| 1035 | n-C$_6$H$_{13}$ | n-C$_4$H$_9$ | |
| 1036 | n-C$_6$H$_{13}$ | n-C$_5$H$_{11}$ | |
| 1037 | n-C$_6$H$_{13}$ | n-C$_6$H$_{13}$ | |
| 1038 | n-C$_6$H$_{13}$ | n-C$_7$H$_{15}$ | |
| 1039 | n-C$_7$H$_{15}$ | CH$_3$ | |
| 1040 | n-C$_7$H$_{15}$ | C$_2$H$_5$ | |
| 1041 | n-C$_7$H$_{15}$ | n-C$_3$H$_7$ | |
| 1042 | n-C$_7$H$_{15}$ | n-C$_4$H$_9$ | |
| 1043 | n-C$_7$H$_{15}$ | n-C$_5$H$_{11}$ | |
| 1044 | n-C$_7$H$_{15}$ | n-C$_6$H$_{13}$ | |
| 1045 | n-C$_7$H$_{15}$ | n-C$_7$H$_{15}$ | |
| 1046 | CH$_2$=CH | CH$_3$ | |
| 1047 | CH$_2$=CH | C$_2$H$_5$ | |
| 1048 | CH$_2$=CH | n-C$_3$H$_7$ | |
| 1049 | CH$_2$=CH | n-C$_4$H$_9$ | |
| 1050 | CH$_2$=CH | n-C$_5$H$_{11}$ | |
| 1051 | CH$_2$=CH | n-C$_6$H$_{13}$ | |
| 1052 | CH$_2$=CH | n-C$_7$H$_{15}$ | |
| 1053 | CH$_3$—CH=CH | CH$_3$ | |
| 1054 | CH$_3$—CH=CH | C$_2$H$_5$ | |
| 1055 | CH$_3$—CH=CH | n-C$_3$H$_7$ | |
| 1056 | CH$_3$—CH=CH | n-C$_4$H$_9$ | |
| 1057 | CH$_3$—CH=CH | n-C$_5$H$_{11}$ | |
| 1058 | CH$_3$—CH=CH | n-C$_6$H$_{13}$ | |
| 1059 | CH$_3$—CH=CH | n-C$_7$H$_{15}$ | |

Note:
* values extrapolated from 10% solution in ZLI-4792 or ZLI-2857 (Δε).

Examples 1060 to 1122

The following are prepared from 31 analogously to Example 9:

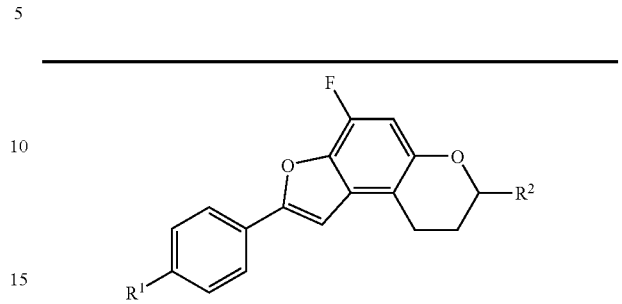

| No. | R¹ | R² | Phase sequence T/° C. |
|---|---|---|---|
| 1060 | CH$_3$ | CH$_3$ | |
| 1061 | CH$_3$ | C$_2$H$_5$ | |
| 1062 | CH$_3$ | n-C$_3$H$_7$ | |
| 1063 | CH$_3$ | n-C$_4$H$_9$ | |
| 1064 | CH$_3$ | n-C$_5$H$_{11}$ | |
| 1065 | CH$_3$ | n-C$_6$H$_{13}$ | |
| 1066 | CH$_3$ | n-C$_7$H$_{15}$ | |
| 1067 | C$_2$H$_5$ | CH$_3$ | |
| 1068 | C$_2$H$_5$ | C$_2$H$_5$ | |
| 1069 | C$_2$H$_5$ | n-C$_3$H$_7$ | |
| 1070 | C$_2$H$_5$ | n-C$_4$H$_9$ | |
| 1071 | C$_2$H$_5$ | n-C$_5$H$_{11}$ | |
| 1072 | C$_2$H$_5$ | n-C$_6$H$_{13}$ | |
| 1073 | C$_2$H$_5$ | n-C$_7$H$_{15}$ | |
| 1074 | n-C$_3$H$_7$ | CH$_3$ | |
| 1075 | n-C$_3$H$_7$ | C$_2$H$_5$ | |
| 1076 | n-C$_3$H$_7$ | n-C$_3$H$_7$ | |
| 1077 | n-C$_3$H$_7$ | n-C$_4$H$_9$ | |
| 1078 | n-C$_3$H$_7$ | n-C$_5$H$_{11}$ | |
| 1079 | n-C$_3$H$_7$ | n-C$_6$H$_{13}$ | |
| 1080 | n-C$_3$H$_7$ | n-C$_7$H$_{15}$ | |
| 1081 | n-C$_4$H$_9$ | CH$_3$ | |
| 1082 | n-C$_4$H$_9$ | C$_2$H$_5$ | |
| 1083 | n-C$_4$H$_9$ | n-C$_3$H$_7$ | |
| 1084 | n-C$_4$H$_9$ | n-C$_4$H$_9$ | |
| 1085 | n-C$_4$H$_9$ | n-C$_5$H$_{11}$ | |
| 1086 | n-C$_4$H$_9$ | n-C$_6$H$_{13}$ | |
| 1087 | n-C$_4$H$_9$ | n-C$_7$H$_{15}$ | |
| 1088 | n-C$_5$H$_{11}$ | CH$_3$ | |
| 1089 | n-C$_5$H$_{11}$ | C$_2$H$_5$ | |
| 1090 | n-C$_5$H$_{11}$ | n-C$_3$H$_7$ | |
| 1091 | n-C$_5$H$_{11}$ | n-C$_4$H$_9$ | |
| 1092 | n-C$_5$H$_{11}$ | n-C$_5$H$_{11}$ | |
| 1093 | n-C$_5$H$_{11}$ | n-C$_6$H$_{13}$ | |
| 1094 | n-C$_5$H$_{11}$ | n-C$_7$H$_{15}$ | |
| 1095 | n-C$_6$H$_{13}$ | CH$_3$ | |
| 1096 | n-C$_6$H$_{13}$ | C$_2$H$_5$ | |
| 1097 | n-C$_6$H$_{13}$ | n-C$_3$H$_7$ | |
| 1098 | n-C$_6$H$_{13}$ | n-C$_4$H$_9$ | |
| 1099 | n-C$_6$H$_{13}$ | n-C$_5$H$_{11}$ | |
| 1100 | n-C$_6$H$_{13}$ | n-C$_6$H$_{13}$ | |
| 1101 | n-C$_6$H$_{13}$ | n-C$_7$H$_{15}$ | |
| 1102 | n-C$_7$H$_{15}$ | CH$_3$ | |
| 1103 | n-C$_7$H$_{15}$ | C$_2$H$_5$ | |
| 1104 | n-C$_7$H$_{15}$ | n-C$_3$H$_7$ | |
| 1105 | n-C$_7$H$_{15}$ | n-C$_4$H$_9$ | |
| 1106 | n-C$_7$H$_{15}$ | n-C$_5$H$_{11}$ | |
| 1107 | n-C$_7$H$_{15}$ | n-C$_6$H$_{13}$ | |
| 1108 | n-C$_7$H$_{15}$ | n-C$_7$H$_{15}$ | |
| 1109 | CH$_3$O | CH$_3$ | |
| 1110 | CH$_3$O | C$_2$H$_5$ | |
| 1111 | CH$_3$O | n-C$_3$H$_7$ | |
| 1112 | CH$_3$O | n-C$_4$H$_9$ | |
| 1113 | CH$_3$O | n-C$_5$H$_{11}$ | |
| 1114 | CH$_3$O | n-C$_6$H$_{13}$ | |
| 1115 | CH$_3$O | n-C$_7$H$_{15}$ | |
| 1116 | C$_2$H$_5$O | CH$_3$ | |
| 1117 | C$_2$H$_5$O | C$_2$H$_5$ | |
| 1118 | C$_2$H$_5$O | n-C$_3$H$_7$ | |
| 1119 | C$_2$H$_5$O | n-C$_4$H$_9$ | |

-continued

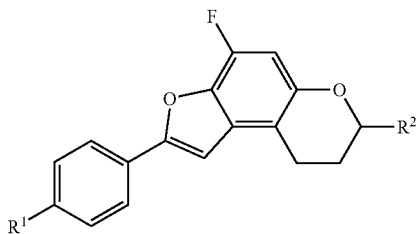

| No. | R¹ | R² | Phase sequence T/° C. |
|---|---|---|---|
| 1120 | $C_2H_5O$ | $n\text{-}C_5H_{11}$ | |
| 1121 | $C_2H_5O$ | $n\text{-}C_6H_{13}$ | |
| 1122 | $C_2H_5O$ | $n\text{-}C_7H_{15}$ | |

Note:
* values extrapolated from 10% solution in ZLI-4792 or ZLI-2857 (Δε).

Examples 1123 to 1185

The following are prepared from 36 analogously to Example 9:

| No. | R¹ | R² | Phase sequence T/° C. |
|---|---|---|---|
| 1123 | $CH_3$ | $CH_3$ | |
| 1124 | $CH_3$ | $C_2H_5$ | |
| 1125 | $CH_3$ | $n\text{-}C_3H_7$ | |
| 1126 | $CH_3$ | $n\text{-}C_4H_9$ | |
| 1127 | $CH_3$ | $n\text{-}C_5H_{11}$ | |
| 1128 | $CH_3$ | $n\text{-}C_6H_{13}$ | |
| 1129 | $CH_3$ | $n\text{-}C_7H_{15}$ | |
| 1130 | $C_2H_5$ | $CH_3$ | |
| 1131 | $C_2H_5$ | $C_2H_5$ | |
| 1132 | $C_2H_5$ | $n\text{-}C_3H_7$ | |
| 1133 | $C_2H_5$ | $n\text{-}C_4H_9$ | |
| 1134 | $C_2H_5$ | $n\text{-}C_5H_{11}$ | |
| 1135 | $C_2H_5$ | $n\text{-}C_6H_{13}$ | |
| 1136 | $C_2H_5$ | $n\text{-}C_7H_{15}$ | |
| 1137 | $n\text{-}C_3H_7$ | $CH_3$ | |
| 1138 | $n\text{-}C_3H_7$ | $C_2H_5$ | |
| 1139 | $n\text{-}C_3H_7$ | $n\text{-}C_3H_7$ | |
| 1140 | $n\text{-}C_3H_7$ | $n\text{-}C_4H_9$ | |
| 1141 | $n\text{-}C_3H_7$ | $n\text{-}C_5H_{11}$ | |
| 1142 | $n\text{-}C_3H_7$ | $n\text{-}C_6H_{13}$ | |
| 1143 | $n\text{-}C_3H_7$ | $n\text{-}C_7H_{15}$ | |
| 1144 | $n\text{-}C_4H_9$ | $CH_3$ | |
| 1145 | $n\text{-}C_4H_9$ | $C_2H_5$ | |
| 1146 | $n\text{-}C_4H_9$ | $n\text{-}C_3H_7$ | |
| 1147 | $n\text{-}C_4H_9$ | $n\text{-}C_4H_9$ | |
| 1144 | $n\text{-}C_4H_9$ | $n\text{-}C_5H_{11}$ | |
| 1149 | $n\text{-}C_4H_9$ | $n\text{-}C_6H_{13}$ | |
| 1150 | $n\text{-}C_4H_9$ | $n\text{-}C_7H_{15}$ | |
| 1151 | $n\text{-}C_5H_{11}$ | $CH_3$ | |
| 1152 | $n\text{-}C_5H_{11}$ | $C_2H_5$ | |
| 1153 | $n\text{-}C_5H_{11}$ | $n\text{-}C_3H_7$ | |
| 1154 | $n\text{-}C_5H_{11}$ | $n\text{-}C_4H_9$ | |
| 1155 | $n\text{-}C_5H_{11}$ | $n\text{-}C_5H_{11}$ | |
| 1156 | $n\text{-}C_5H_{11}$ | $n\text{-}C_6H_{13}$ | |
| 1157 | $n\text{-}C_5H_{11}$ | $n\text{-}C_7H_{15}$ | |
| 1158 | $n\text{-}C_6H_{13}$ | $CH_3$ | |
| 1159 | $n\text{-}C_6H_{13}$ | $C_2H_5$ | |
| 1160 | $n\text{-}C_6H_{13}$ | $n\text{-}C_3H_7$ | |
| 1161 | $n\text{-}C_6H_{13}$ | $n\text{-}C_4H_9$ | |
| 1162 | $n\text{-}C_6H_{13}$ | $n\text{-}C_5H_{11}$ | |
| 1163 | $n\text{-}C_6H_{13}$ | $n\text{-}C_6H_{13}$ | |
| 1164 | $n\text{-}C_6H_{13}$ | $n\text{-}C_7H_{15}$ | |
| 1165 | $n\text{-}C_7H_{15}$ | $CH_3$ | |
| 1166 | $n\text{-}C_7H_{15}$ | $C_2H_5$ | |
| 1167 | $n\text{-}C_7H_{15}$ | $n\text{-}C_3H_7$ | |
| 1168 | $n\text{-}C_7H_{15}$ | $n\text{-}C_4H_9$ | |
| 1169 | $n\text{-}C_7H_{15}$ | $n\text{-}C_5H_{11}$ | |
| 1170 | $n\text{-}C_7H_{15}$ | $n\text{-}C_6H_{13}$ | |
| 1171 | $n\text{-}C_7H_{15}$ | $n\text{-}C_7H_{15}$ | |
| 1172 | $CH_3O$ | $CH_3$ | |
| 1173 | $CH_3O$ | $C_2H_5$ | |
| 1174 | $CH_3O$ | $n\text{-}C_3H_7$ | |
| 1175 | $CH_3O$ | $n\text{-}C_4H_9$ | |
| 1176 | $CH_3O$ | $n\text{-}C_5H_{11}$ | |
| 1177 | $CH_3O$ | $n\text{-}C_6H_{13}$ | |
| 1178 | $CH_3O$ | $n\text{-}C_7H_{15}$ | |
| 1179 | $C_2H_5O$ | $CH_3$ | |
| 1180 | $C_2H_5O$ | $C_2H_5$ | |
| 1181 | $C_2H_5O$ | $n\text{-}C_3H_7$ | |
| 1182 | $C_2H_5O$ | $n\text{-}C_4H_9$ | |
| 1183 | $C_2H_5O$ | $n\text{-}C_5H_{11}$ | |
| 1184 | $C_2H_5O$ | $n\text{-}C_6H_{13}$ | |
| 1185 | $C_2H_5O$ | $n\text{-}C_7H_{15}$ | |

Note:
* values extrapolated from 10% solution in ZLI-4792 or ZLI-2857 (Δε).

Without further elaboration, it is believed that one skilled in the art can, using the preceding description, utilize the present invention to its fullest extent. The preceding preferred specific embodiments are, therefore, to be construed merely illustrative, and not limitative of the remainder of the disclosure in any way whatsoever.

The entire disclosure[s] of all applications, patents and publications, cited herein and of corresponding EP Patent Application No. 06025029.7, filed on Dec. 4, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula I

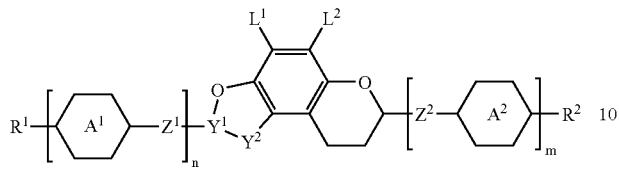

in which
R¹ and R² each, independently of one another, denote H, halogen, —CN, —SCN, —SF$_5$, —CF$_3$, —CHF$_2$, —CH$_2$F, —OCF$_3$, —OCHF$_2$ or an alkyl group having 1 to 15 C atoms, which is optionally monosubstituted by CN or CF$_3$ or at least monosubstituted by halogen and in which optionally one or more CH$_2$ groups, in each case independently of one another, are replaced by —O—, —S—, —CH=CH—, —CF=CF—, —CF=CH—, —CH=CF—,

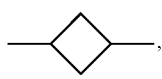, ,

—CO—, —CO—O—, —O—CO— or —O—CO—O— in such a way that neither O nor S atoms are linked directly to one another,
>Y¹—Y²— denotes >C=CH— or >CH—CH$_2$—,
L¹ and L² are both F,

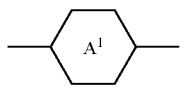 and 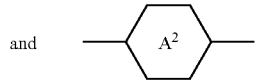

each, independently of one another, and, if present more than once, these also independently of one another, denote
(a) a trans-1,4-cyclohexylene radical, in which one or two non-adjacent CH$_2$ groups are optionally replaced by —O— and/or —S—,
(b) a 1,4-cyclohexenylene radical,
(c) a 1,4-phenylene radical, in which one or two non-adjacent CH groups are optionally replaced by N,
(d) naphthalene-2,6-diyl, decahydronaphthalene-2,6-diyl or 1,2,3,4-tetrahydronaphthalene-2,6-diyl, or
(e) 1,4-bicyclo[2.2.2]octylene, 1,3-bicyclo[1.1.1]pentylene or spiro[3.3]heptane-2,6-diyl,
wherein in
(a) and (b), one or more —CH$_2$— groups, independently of one another, are optionally replaced by a —CHF— or a —CF$_2$— group, and in (c) and (d), one or more —CH= groups, independently of one another, are optionally replaced by —CF=, —CCl=, —CBr=, —C(CN)=, —C(CH$_3$)=, —C(CH$_2$F)=, —C(CHF$_2$)=, —C(OCH$_3$)=, —C(OCHF$_2$)= or —C(OCF$_3$)=,
Z¹ and Z² each, independently of one another, and, if present more than once, these also independently of one another, denote a single bond, —CH$_2$—CH$_2$—, —CF$_2$—CH$_2$—, —CH$_2$—CF$_2$—, —CF$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, or —OCF$_2$—, or a combination of two of these groups, where no two O atoms are bonded to one another, and
n and m each independently denote 0, 1, 2 or 3, where (n+m) denotes 0, 1, 2 or 3.

2. A compound according to claim 1, which is of formula 1A

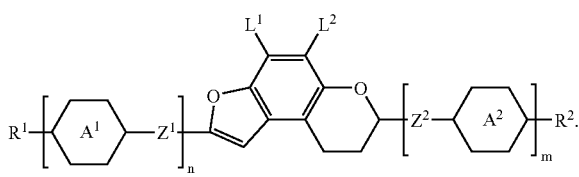

3. A compound according to claim 1, which is of formula 1B

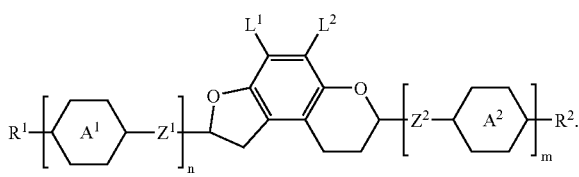

4. A compound according to claim 1, wherein Z¹ and Z² denote a single bond.

5. A compound according to claim 1, wherein (m+n) denotes 0 or 1.

6. A compound according to claim 1, wherein (m+n) denotes 0.

7. A liquid-crystal medium, comprising a compound according to claim 1.

8. A liquid-crystal medium according to claim 7, which has a nematic phase.

9. A liquid-crystal medium according to claim 7, which comprises one or more dielectrically negative compounds of formula II

in which
R²¹ and R²² each, independently of one another, denote H, halogen, —CN, —SCN, —SF$_5$, —CF$_3$, —CHF$_2$, —CH$_2$F, —OCF$_3$, —OCHF$_2$ or an alkyl group having 1 to 15 C atoms, which is optionally monosubstituted by CN or CF$_3$ or at least monosubstituted by halogen and in which optionally one or more CH$_2$ groups, in each case independently of one another, are replaced by —O—, —S—, —CH=CH—, —CF=CF—, —CF=CH—, —CH=CF—,

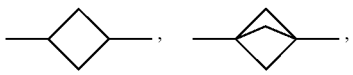

—CO—, —CO—O—, —O—CO— or —O—CO—O— in such a way that neither O nor S atoms are linked directly to one another, $Z^{21}$ and $Z^{22}$ each, independently of one another, and, if present more than once, these also independently of one another, denote a single bond, —CH$_2$—CH$_2$—, —CF$_2$—CH$_2$—, —CH$_2$—CF$_2$—, —CF$_2$—CF$_2$—, —CH=CH—, —CF=CF—, —CF=CH—, —CH=CF—, —C≡C—, —COO—, —OCO—, —CH$_2$O—, —OCH$_2$—, —CF$_2$O—, or —OCF$_2$—, or a combination of two of these groups, where no two O atoms are bonded to one another, and

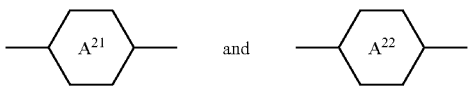

each, independently of one another, denote

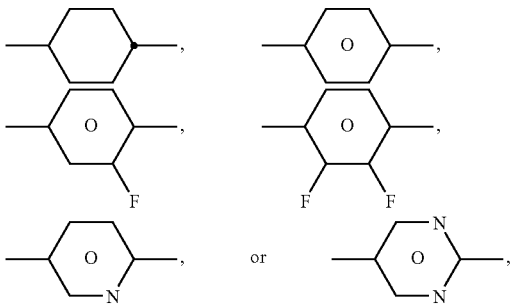

$L^{21}$ and $L^{22}$ both denote C—F or one of the two denotes N and the other denotes C—F, and l denotes 0 or 1.

10. A liquid-crystal medium according to claim 9, which comprises one or more compounds of formula II-1

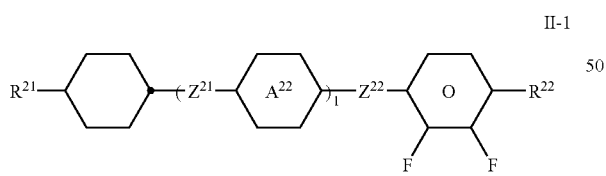

II-1 in which $R^{21}$, $R^{22}$, $Z^{12}$, $Z^{22}$

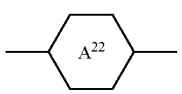

and l have the meanings given for compounds of formula II.

11. An electro-optical display, containing a liquid-crystal medium according to claim 7.

12. A display according to claim 11, which is a vertically aligned nematic liquid-crystal display.

13. A process for preparing a liquid-crystal medium according to claim 7, comprising mixing one or more compounds of formula I with one or more further compounds.

14. A process for preparing an electro-optical display, comprising introducing a liquid-crystal medium according to claim 7 between two substrates.

15. A compound, which is one of the following compounds

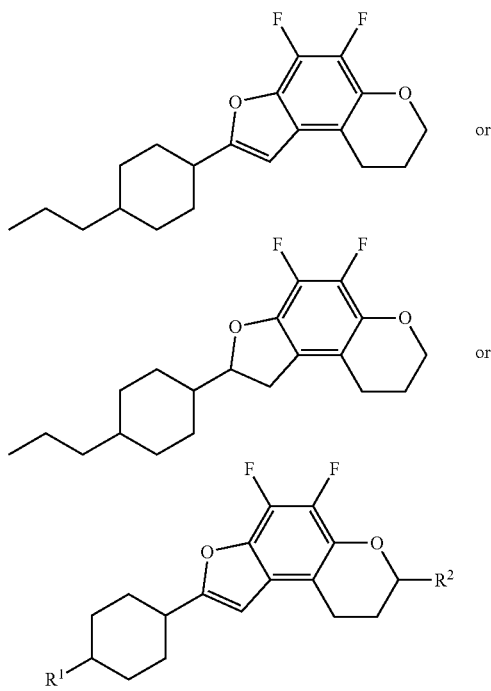

wherein

| $R^1$ | $R^2$ |
|---|---|
| CH$_3$ | CH$_3$ |
| CH$_3$ | C$_2$H$_5$ |
| CH$_3$ | n-C$_3$H$_7$ |
| CH$_3$ | n-C$_4$H$_9$ |
| CH$_3$ | n-C$_5$H$_{11}$ |
| CH$_3$ | n-C$_6$H$_{13}$ |
| CH$_3$ | n-C$_7$H$_{15}$ |
| C$_2$H$_5$ | CH$_3$ |
| C$_2$H$_5$ | C$_2$H$_5$ |
| C$_2$H$_5$ | n-C$_3$H$_7$ |
| C$_2$H$_5$ | n-C$_4$H$_9$ |
| C$_2$H$_5$ | n-C$_5$H$_{11}$ |
| C$_2$H$_5$ | n-C$_6$H$_{13}$ |
| C$_2$H$_5$ | n-C$_7$H$_{15}$ |
| n-C$_3$H$_7$ | CH$_3$ |
| n-C$_3$H$_7$ | C$_2$H$_5$ |
| n-C$_3$H$_7$ | n-C$_3$H$_7$ |
| n-C$_3$H$_7$ | n-C$_4$H$_9$ |
| n-C$_3$H$_7$ | n-C$_5$H$_{11}$ |
| n-C$_3$H$_7$ | n-C$_6$H$_{13}$ |
| n-C$_3$H$_7$ | n-C$_7$H$_{15}$ |
| n-C$_4$H$_9$ | CH$_3$ |
| n-C$_4$H$_9$ | C$_2$H$_5$ |
| n-C$_4$H$_9$ | n-C$_3$H$_7$ |
| n-C$_4$H$_9$ | n-C$_4$H$_9$ |
| n-C$_4$H$_9$ | n-C$_5$H$_{11}$ |
| n-C$_4$H$_9$ | n-C$_6$H$_{13}$ |
| n-C$_4$H$_9$ | n-C$_7$H$_{15}$ |

-continued

| R¹ | R² |
|---|---|
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₃O | CH₃ |
| CH₃O | C₂H₅ |
| CH₃O | n-C₃H₇ |
| CH₃O | n-C₄H₉ |
| CH₃O | n-C₅H₁₁ |
| CH₃O | n-C₆H₁₃ |
| CH₃O | n-C₇H₁₅ |
| C₂H₅O | CH₃ |
| C₂H₅O | C₂H₅ |
| C₂H₅O | n-C₃H₇ |
| C₂H₅O | n-C₄H₉ |
| C₂H₅O | n-C₅H₁₁ |
| C₂H₅O | n-C₆H₁₃ |
| C₂H₅O | n-C₇H₁₅ |
| CH₂=CH | CH₃ |
| CH₂=CH | C₂H₅ |
| CH₂=CH | n-C₃H₇ |
| CH₂=CH | n-C₄H₉ |
| CH₂=CH | n-C₅H₁₁ |
| CH₂=CH | n-C₆H₁₃ |
| CH₂=CH | n-C₇H₁₅ |
| CH₃—CH=CH | CH₃ |
| CH₃—CH=CH | C₂H₅ |
| CH₃—CH=CH | n-C₃H₇ |
| CH₃—CH=CH | n-C₄H₉ |
| CH₃—CH=CH | n-C₅H₁₁ |
| CH₃—CH=CH | n-C₆H₁₃ |
| CH₃—CH=CH | n-C₇H₁₅ | or

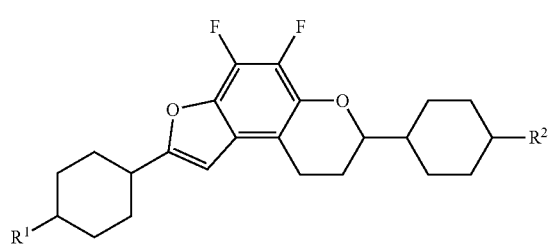

wherein

| R¹ | R² |
|---|---|
| CH₃ | CH₃ |
| CH₃ | C₂H₅ |
| CH₃ | n-C₃H₇ |
| CH₃ | n-C₄H₉ |
| CH₃ | n-C₅H₁₁ |
| CH₃ | n-C₆H₁₃ |
| CH₃ | n-C₇H₁₅ |
| C₂H₅ | CH₃ |
| C₂H₅ | C₂H₅ |
| C₂H₅ | n-C₃H₇ |
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₃O | CH₃ |
| CH₃O | C₂H₅ |
| CH₃O | n-C₃H₇ |
| CH₃O | n-C₄H₉ |
| CH₃O | n-C₅H₁₁ |
| CH₃O | n-C₆H₁₃ |
| CH₃O | n-C₇H₁₅ |
| C₂H₅O | CH₃ |
| C₂H₅O | C₂H₅ |
| C₂H₅O | n-C₃H₇ |
| C₂H₅O | n-C₄H₉ |
| C₂H₅O | n-C₅H₁₁ |
| C₂H₅O | n-C₆H₁₃ |
| C₂H₅O | n-C₇H₁₅ |
| CH₂=CH | CH₃ |
| CH₂=CH | C₂H₅ |
| CH₂=CH | n-C₃H₇ |
| CH₂=CH | n-C₄H₉ |
| CH₂=CH | n-C₅H₁₁ |
| CH₂=CH | n-C₆H₁₃ |
| CH₂=CH | n-C₇H₁₅ |
| CH₃—CH=CH | CH₃ |
| CH₃—CH=CH | C₂H₅ |
| CH₃—CH=CH | n-C₃H₇ |
| CH₃—CH=CH | n-C₄H₉ |
| CH₃—CH=CH | n-C₅H₁₁ |
| CH₃—CH=CH | n-C₆H₁₃ |
| CH₃—CH=CH | n-C₇H₁₅ | or

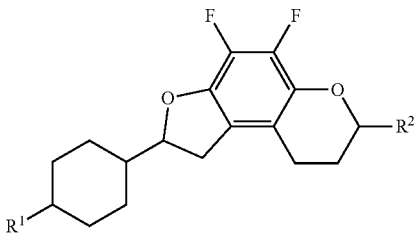

wherein

| R¹ | R² |
|---|---|
| CH₃ | CH₃ |
| CH₃ | C₂H₅ |
| CH₃ | n-C₃H₇ |
| CH₃ | n-C₄H₉ |
| CH₃ | n-C₅H₁₁ |
| CH₃ | n-C₆H₁₃ |
| CH₃ | n-C₇H₁₅ |
| C₂H₅ | CH₃ |
| C₂H₅ | C₂H₅ |
| C₂H₅ | n-C₃H₇ |
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₃O | CH₃ |
| CH₃O | C₂H₅ |
| CH₃O | n-C₃H₇ |
| CH₃O | n-C₄H₉ |
| CH₃O | n-C₅H₁₁ |
| CH₃O | n-C₆H₁₃ |
| CH₃O | n-C₇H₁₅ |
| C₂H₅O | CH₃ |
| C₂H₅O | C₂H₅ |
| C₂H₅O | n-C₃H₇ |

-continued

| R¹ | R² |
|---|---|
| C₂H₅O | n-C₄H₉ |
| C₂H₅O | n-C₅H₁₁ |
| C₂H₅O | n-C₆H₁₃ |
| C₂H₅O | n-C₇H₁₅ | or

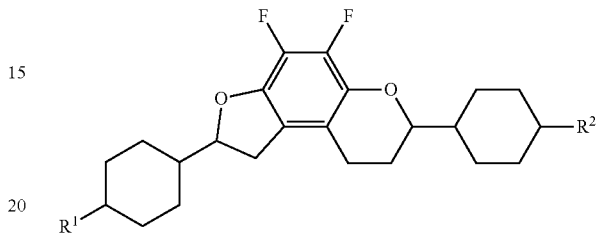

wherein

| R¹ | R² |
|---|---|
| CH₃ | CH₃ |
| CH₃ | C₂H₅ |
| CH₃ | n-C₃H₇ |
| CH₃ | n-C₄H₉ |
| CH₃ | n-C₅H₁₁ |
| CH₃ | n-C₆H₁₃ |
| CH₃ | n-C₇H₁₅ |
| C₂H₅ | CH₃ |
| C₂H₅ | C₂H₅ |
| C₂H₅ | n-C₃H₇ |
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |

-continued

| R¹ | R² |
|---|---|
| n-C₇H₁₅ | n-C₇H₁₅ |
| CH₃O | CH₃ |
| CH₃O | C₂H₅ |
| CH₃O | n-C₃H₇ |
| CH₃O | n-C₄H₉ |
| CH₃O | n-C₅H₁₁ |
| CH₃O | n-C₆H₁₃ |
| CH₃O | n-C₇H₁₅ |
| C₂H₅O | CH₃ |
| C₂H₅O | C₂H₅ |
| C₂H₅O | n-C₃H₇ |
| C₂H₅O | n-C₄H₉ |
| C₂H₅O | n-C₅H₁₁ |
| C₂H₅O | n-C₆H₁₃ |
| C₂H₅O | n-C₇H₁₅ | or

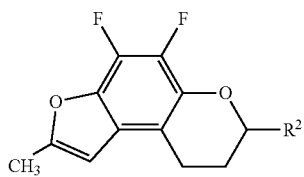

wherein

| R² |
|---|
| CH₃ |
| C₂H₅ |
| n-C₃H₇ |
| n-C₄H₉ |
| n-C₅H₁₁ |
| n-C₆H₁₃ |
| n-C₇H₁₅ | or

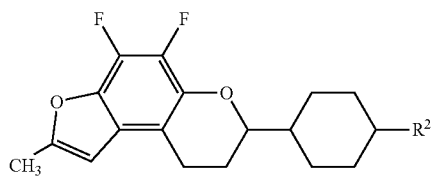

wherein

| R² |
|---|
| CH₃ |
| C₂H₅ |
| n-C₃H₇ |
| n-C₄H₉ |
| n-C₅H₁₁ |
| n-C₆H₁₃ |
| n-C₇H₁₅ | or

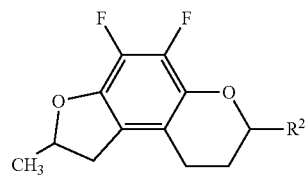

wherein

| R² |
|---|
| CH₃ |
| C₂H₅ |
| n-C₃H₇ |
| n-C₄H₉ |
| n-C₅H₁₁ |
| n-C₆H₁₃ |
| n-C₇H₁₅ | or

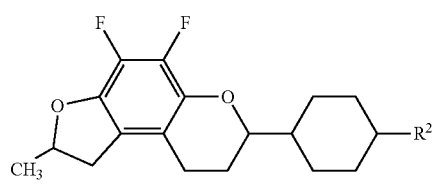

wherein

| R² |
|---|
| CH₃ |
| C₂H₅ |
| n-C₃H₇ |
| n-C₄H₉ |
| n-C₅H₁₁ |
| n-C₆H₁₃ |
| n-C₇H₁₅ | or

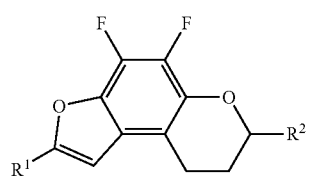

wherein

| R¹ | R² |
|---|---|
| C₂H₅ | CH₃ |
| C₂H₅ | C₂H₅ |
| C₂H₅ | n-C₃H₇ |
| C₂H₅ | n-C₄H₉ |

-continued

| R¹ | R² |
|---|---|
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₂=CH | CH₃ |
| CH₂=CH | C₂H₅ |
| CH₂=CH | n-C₃H₇ |
| CH₂=CH | n-C₄H₉ |
| CH₂=CH | n-C₅H₁₁ |
| CH₂=CH | n-C₆H₁₃ |
| CH₂=CH | n-C₇H₁₅ |
| CH₃—CH=CH | CH₃ |
| CH₃—CH=CH | C₂H₅ |
| CH₃—CH=CH | n-C₃H₇ |
| CH₃—CH=CH | n-C₄H₉ |
| CH₃—CH=CH | n-C₅H₁₁ |
| CH₃—CH=CH | n-C₆H₁₃ |
| CH₃—CH=CH | n-C₇H₁₅ | or

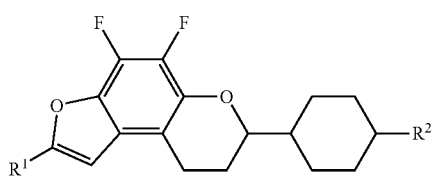

wherein

| R¹ | R² |
|---|---|
| C₂H₅ | CH₃ |
| C₂H₅ | C₂H₅ |
| C₂H₅ | n-C₃H₇ |

-continued

| R¹ | R² |
|---|---|
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₂=CH | CH₃ |
| CH₂=CH | C₂H₅ |
| CH₂=CH | n-C₃H₇ |
| CH₂=CH | n-C₄H₉ |
| CH₂=CH | n-C₅H₁₁ |
| CH₂=CH | n-C₆H₁₃ |
| CH₂=CH | n-C₇H₁₅ |
| CH₃—CH=CH | CH₃ |
| CH₃—CH=CH | C₂H₅ |
| CH₃—CH=CH | n-C₃H₇ |
| CH₃—CH=CH | n-C₄H₉ |
| CH₃—CH=CH | n-C₅H₁₁ |
| CH₃—CH=CH | n-C₆H₁₃ |
| CH₃—CH=CH | n-C₇H₁₅ | or

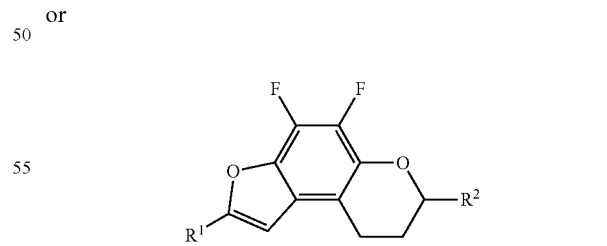

wherein

| R¹ | R² |
|---|---|
| CH₃ | n-C₇H₁₅ |
| C₂H₅ | CH₃ |

-continued

| R¹ | R² |
|---|---|
| C₂H₅ | C₂H₅ |
| C₂H₅ | n-C₃H₇ |
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ | or

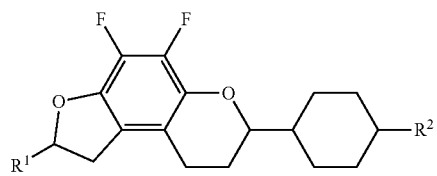

wherein

| R¹ | R² |
|---|---|
| CH₃ | n-C₇H₁₅ |
| C₂H₅ | CH₃ |
| C₂H₅ | C₂H₅ |
| C₂H₅ | n-C₃H₇ |
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |

-continued

| R¹ | R² |
|---|---|
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ | or

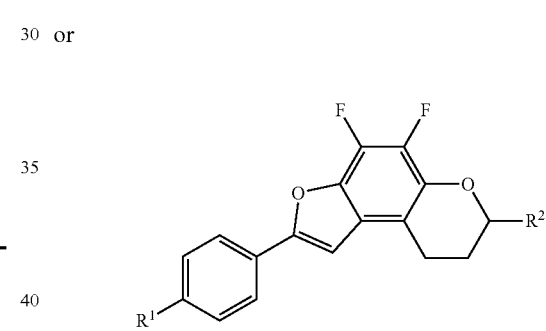

wherein

| R¹ | R² |
|---|---|
| CH₃ | CH₃ |
| CH₃ | C₂H₅ |
| CH₃ | n-C₃H₇ |
| CH₃ | n-C₄H₉ |
| CH₃ | n-C₅H₁₁ |
| CH₃ | n-C₆H₁₃ |
| CH₃ | n-C₇H₁₅ |
| C₂H₅ | CH₃ |
| C₂H₅ | C₂H₅ |
| C₂H₅ | n-C₃H₇ |
| C₂H₅ | n-C₄H₉ |
| C₂H₅ | n-C₅H₁₁ |
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |

-continued

| R¹ | R² |
|---|---|
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₃O | CH₃ |
| CH₃O | C₂H₅ |
| CH₃O | n-C₃H₇ |
| CH₃O | n-C₄H₉ |
| CH₃O | n-C₅H₁₁ |
| CH₃O | n-C₆H₁₃ |
| CH₃O | n-C₇H₁₅ |
| C₂H₅O | CH₃ |
| C₂H₅O | C₂H₅ |
| C₂H₅O | n-C₃H₇ |
| C₂H₅O | n-C₄H₉ |
| C₂H₅O | n-C₅H₁₁ |
| C₂H₅O | n-C₆H₁₃ |
| C₂H₅O | n-C₇H₁₅ | or wherein

| R¹ | R² |
|---|---|
| CH₃ | CH₃ |
| CH₃ | C₂H₅ |
| CH₃ | n-C₃H₇ |
| CH₃ | n-C₄H₉ |
| CH₃ | n-C₅H₁₁ |
| CH₃ | n-C₆H₁₃ |
| CH₃ | n-C₇H₁₅ |
| C₂H₅ | CH₃ |
| C₂H₅ | C₂H₅ |
| C₂H₅ | n-C₃H₇ |
| C₂H₅ | n-C₄H₉ |
| C₂H₅ | n-C₅H₁₁ |

-continued

| R¹ | R² |
|---|---|
| C₂H₅ | n-C₆H₁₃ |
| C₂H₅ | n-C₇H₁₅ |
| n-C₃H₇ | CH₃ |
| n-C₃H₇ | C₂H₅ |
| n-C₃H₇ | n-C₃H₇ |
| n-C₃H₇ | n-C₄H₉ |
| n-C₃H₇ | n-C₅H₁₁ |
| n-C₃H₇ | n-C₆H₁₃ |
| n-C₃H₇ | n-C₇H₁₅ |
| n-C₄H₉ | CH₃ |
| n-C₄H₉ | C₂H₅ |
| n-C₄H₉ | n-C₃H₇ |
| n-C₄H₉ | n-C₄H₉ |
| n-C₄H₉ | n-C₅H₁₁ |
| n-C₄H₉ | n-C₆H₁₃ |
| n-C₄H₉ | n-C₇H₁₅ |
| n-C₅H₁₁ | CH₃ |
| n-C₅H₁₁ | C₂H₅ |
| n-C₅H₁₁ | n-C₃H₇ |
| n-C₅H₁₁ | n-C₄H₉ |
| n-C₅H₁₁ | n-C₅H₁₁ |
| n-C₅H₁₁ | n-C₆H₁₃ |
| n-C₅H₁₁ | n-C₇H₁₅ |
| n-C₆H₁₃ | CH₃ |
| n-C₆H₁₃ | C₂H₅ |
| n-C₆H₁₃ | n-C₃H₇ |
| n-C₆H₁₃ | n-C₄H₉ |
| n-C₆H₁₃ | n-C₅H₁₁ |
| n-C₆H₁₃ | n-C₆H₁₃ |
| n-C₆H₁₃ | n-C₇H₁₅ |
| n-C₇H₁₅ | CH₃ |
| n-C₇H₁₅ | C₂H₅ |
| n-C₇H₁₅ | n-C₃H₇ |
| n-C₇H₁₅ | n-C₄H₉ |
| n-C₇H₁₅ | n-C₅H₁₁ |
| n-C₇H₁₅ | n-C₆H₁₃ |
| n-C₇H₁₅ | n-C₇H₁₅ |
| CH₃O | CH₃ |
| CH₃O | C₂H₅ |
| CH₃O | n-C₃H₇ |
| CH₃O | n-C₄H₉ |
| CH₃O | n-C₅H₁₁ |
| CH₃O | n-C₆H₁₃ |
| CH₃O | n-C₇H₁₅ |
| C₂H₅O | CH₃ |
| C₂H₅O | C₂H₅ |
| C₂H₅O | n-C₃H₇ |
| C₂H₅O | n-C₄H₉ |
| C₂H₅O | n-C₅H₁₁ |
| C₂H₅O | n-C₆H₁₃ or |
| C₂H₅O | n-C₇H₁₅. |

16. A liquid-crystal medium, comprising a compound according to claim 15.

17. A liquid-crystal medium according to claim 16, which has a nematic phase.

18. A liquid-crystal medium according to claim 16, which comprises one or more dielectrically negative compounds of formula II in which $R^{21}$ and $R^{22}$ each, independently of one another, denote H, halogen, —CN, —SCN, —SF₅, —CF₃, —CHF₂, —CH₂F, —OCF₃, —OCHF₂ or an alkyl group having 1 to 15 C atoms, which is optionally monosubstituted by CN or $CF_3$ or at least monosubstituted by halogen and in which optionally one or more $CH_2$ groups, in each case independently of one another, are replaced by —O—, —S—, —CH=CH—, —CF=CF—, —CF=CH—, —CH=CF—,

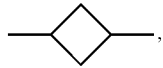 , 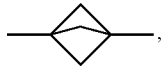 ,

—CO—, —CO—O—, —O—CO— or —O—CO—O— in such a way that neither O nor S atoms are linked directly to one another, $Z^{21}$ and $Z^{22}$ each, independently of one another, and, if present more than once, these also independently of one another, denote a single bond, —$CH_2$—$CH_2$—, —$CF_2$—$CH_2$—, —$CH_2$—$CF_2$—, —$CF_2$—$CF_2$—, —CH=CH—, —CF=CF—, —CF=CH—, —CH=CF—, —C≡C—, —COO—, —OCO—, —$CH_2$O—, —$OCH_2$—, —$CF_2$O—, or —$OCF_2$—, or a combination of two of these groups, where no two O atoms are bonded to one another, and

 and 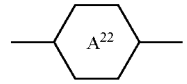

each, independently of one another, denote

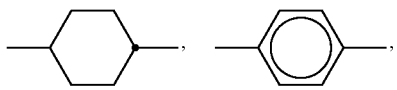

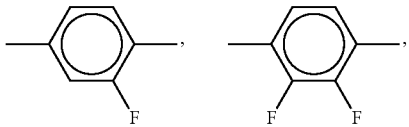

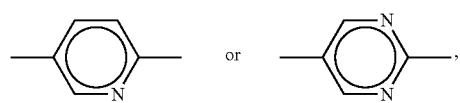

$L^{21}$ and $L^{22}$ both denote C—F or one of the two denotes N and the other denotes C—F, and l denotes 0 or 1.

19. An electro-optical display, containing a liquid-crystal medium according to claim 16.

20. A display according to claim 19, which is a vertically aligned nematic liquid-crystal display.

* * * * *